US010498941B2

(12) United States Patent
Rhoads et al.

(10) Patent No.: US 10,498,941 B2
(45) Date of Patent: *Dec. 3, 2019

(54) SENSOR-SYNCHRONIZED SPECTRALLY-STRUCTURED-LIGHT IMAGING

(71) Applicant: Digimarc Corporation, Beaverton, OR (US)

(72) Inventors: Geoffrey B. Rhoads, West Linn, OR (US); Hugh L. Brunk, Portland, OR (US); John D. Lord, West Linn, OR (US)

(73) Assignee: Digimarc Corporation, Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/036,651

(22) Filed: Jul. 16, 2018

(65) Prior Publication Data

US 2019/0014245 A1    Jan. 10, 2019

Related U.S. Application Data

(63) Continuation of application No. 15/456,300, filed on Mar. 10, 2017, now Pat. No. 10,027,868, which is a
(Continued)

(51) Int. Cl.
*H04N 5/225* (2006.01)
*H04N 9/04* (2006.01)
(Continued)

(52) U.S. Cl.
CPC ......... *H04N 5/2256* (2013.01); *A61B 5/0075* (2013.01); *A61B 5/6898* (2013.01);
(Continued)

(58) Field of Classification Search
CPC ...... H04N 5/2256; H04N 5/2354; H04N 9/73; H04N 5/2254; H04N 9/69; H04N 9/045;
(Continued)

(56) References Cited

U.S. PATENT DOCUMENTS 6,069,696 A    5/2000  McQueen
6,363,366 B1   3/2002  Henty
(Continued)

FOREIGN PATENT DOCUMENTS

FR    2905185 A1     2/2008
WO    2008152922 A1  12/2008
(Continued)

OTHER PUBLICATIONS

Gat, Imaging spectroscopy using tunable filters—a review, AeroSense 2000, International Society for Optics and Photonics, Proc. SPIE vol. 4056, p. 50-64.
(Continued)

*Primary Examiner* — Shahbaz Nazrul
(74) *Attorney, Agent, or Firm* — Digimarc Corporation

(57) ABSTRACT

A spectral imaging device is configured to capture color images synchronized with controlled illumination from different color light emitting diodes. A processor in the device applies a coupling factor to sampled color images to convert sampled pixels into spectral channels corresponding to LED color and color filter. Multi-spectral spectricity vectors produced at pixel locations are used along with spatial information to classify objects, such as produce items.

20 Claims, 68 Drawing Sheets
(43 of 68 Drawing Sheet(s) Filed in Color)

Related U.S. Application Data continuation of application No. 14/201,852, filed on Mar. 8, 2014, now Pat. No. 9,593,982, which is a continuation-in-part of application No. 13/840,451, filed on Mar. 15, 2013, now Pat. No. 9,060,113.

(60) Provisional application No. 61/706,982, filed on Sep. 28, 2012, provisional application No. 61/688,722, filed on May 21, 2012, provisional application No. 61/907,362, filed on Nov. 21, 2013, provisional application No. 61/906,886, filed on Nov. 20, 2013.

(51) Int. Cl.
| | |
|---|---|
| *G01J 3/28* | (2006.01) |
| *H04N 5/235* | (2006.01) |
| *H04N 9/69* | (2006.01) |
| *G01J 3/51* | (2006.01) |
| *A61B 5/00* | (2006.01) |
| *G01J 3/36* | (2006.01) |
| *G01J 3/447* | (2006.01) |
| *G01J 3/02* | (2006.01) |
| *H04N 9/73* | (2006.01) |
| *G01J 3/10* | (2006.01) |
| *G06K 9/46* | (2006.01) |
| *G06K 9/48* | (2006.01) |
| *G06K 9/62* | (2006.01) |

(52) U.S. Cl.
CPC ........... *G01J 3/0229* (2013.01); *G01J 3/0272* (2013.01); *G01J 3/10* (2013.01); *G01J 3/2823* (2013.01); *G01J 3/36* (2013.01); *G01J 3/447* (2013.01); *G01J 3/51* (2013.01); *G01J 3/513* (2013.01); *G06K 9/4652* (2013.01); *G06K 9/481* (2013.01); *G06K 9/628* (2013.01); *G06K 9/6256* (2013.01); *H04N 5/2254* (2013.01); *H04N 5/2354* (2013.01); *H04N 9/045* (2013.01); *H04N 9/69* (2013.01); *H04N 9/73* (2013.01)

(58) Field of Classification Search
CPC ...... G06K 9/481; G06K 9/628; G06K 9/6256; G06K 9/4652; G01J 3/0229; G01J 3/36; G01J 3/51; G01J 3/447; G01J 3/0272; G01J 3/2823; G01J 3/10; G01J 3/513; A61B 5/0075; A61B 5/6898
See application file for complete search history.

(56) References Cited

U.S. PATENT DOCUMENTS

| | | | |
|---|---|---|---|
| 6,466,961 B1 | 10/2002 | Miller | |
| 7,068,446 B2 | 6/2006 | Jacobson | |
| 7,319,990 B1 | 1/2008 | Henty | |
| 7,393,119 B2 | 7/2008 | Lebens | |
| 7,420,663 B2 | 9/2008 | Wang | |
| 7,667,766 B2 | 2/2010 | Lee | |
| 7,922,209 B1 | 4/2011 | Beretta | |
| 7,938,331 B2 | 5/2011 | Brock | |
| 7,995,911 B2 | 8/2011 | Butterworth | |
| 8,224,018 B2 | 7/2012 | Rhoads | |
| 8,284,279 B2 | 10/2012 | Park | |
| 8,358,089 B2 | 1/2013 | Hsia | |
| 8,364,031 B2 | 1/2013 | Geffert | |
| 8,385,971 B2 | 2/2013 | Rhoads | |
| 8,888,207 B2 | 11/2014 | Furness | |
| 9,060,113 B2 | 6/2015 | Rhoads | |
| 9,087,376 B2 | 7/2015 | Rodriguez | |
| 9,621,760 B2 | 4/2017 | Rhoads | |
| 2002/0001080 A1 | 1/2002 | Miller | |
| 2004/0197816 A1 | 10/2004 | Empedocles | |
| 2004/0263911 A1 | 12/2004 | Rodriguez | |
| 2005/0030416 A1 | 2/2005 | Kametani | |
| 2005/0030533 A1 | 2/2005 | Treado | |
| 2005/0111694 A1 | 5/2005 | Loce | |
| 2005/0254709 A1 | 11/2005 | Geshwind | |
| 2006/0115110 A1 | 6/2006 | Rodriguez | |
| 2006/0133061 A1 | 6/2006 | Maeda | |
| 2006/0161788 A1 | 7/2006 | Turpin | |
| 2006/0198551 A1 | 9/2006 | Abe | |
| 2006/0202028 A1 | 9/2006 | Rowe | |
| 2006/0245631 A1 | 11/2006 | Levenson | |
| 2007/0143232 A1 | 6/2007 | Auslander | |
| 2007/0217689 A1 | 9/2007 | Yang | |
| 2008/0101657 A1 | 5/2008 | Durkin | |
| 2008/0112596 A1 | 5/2008 | Rhoads | |
| 2008/0133389 A1 | 6/2008 | Schowengerdt | |
| 2008/0177185 A1 | 7/2008 | Nakao | |
| 2008/0297644 A1 | 12/2008 | Farchtchian | |
| 2009/0067695 A1 | 3/2009 | Komiya | |
| 2009/0112101 A1 | 4/2009 | Furness | |
| 2009/0243493 A1 | 10/2009 | Bergquist | |
| 2010/0042004 A1 | 2/2010 | Dhawan | |
| 2010/0048242 A1 | 2/2010 | Rhoads | |
| 2010/0073504 A1 | 3/2010 | Park | |
| 2010/0093015 A1 | 4/2010 | Panza | |
| 2010/0142003 A1 | 6/2010 | Braun | |
| 2010/0150396 A1 | 6/2010 | Reed | |
| 2010/0150434 A1 | 6/2010 | Reed | |
| 2010/0208240 A1 | 8/2010 | Schowengerdt | |
| 2011/0007935 A1 | 1/2011 | Reed | |
| 2011/0037873 A1 | 2/2011 | Hu | |
| 2011/0052888 A1 | 3/2011 | Eschbach | |
| 2011/0069443 A1 | 3/2011 | Williams | |
| 2011/0090485 A1 | 4/2011 | Cronin | |
| 2011/0098029 A1 | 4/2011 | Rhoads | |
| 2011/0123185 A1 | 5/2011 | Clark | |
| 2011/0157178 A1 | 6/2011 | Tuzel | |
| 2011/0176029 A1 | 7/2011 | Boydston | |
| 2011/0182477 A1 | 7/2011 | Tamrakar | |
| 2011/0212717 A1 | 9/2011 | Rhoads | |
| 2011/0249911 A1 | 10/2011 | Determan | |
| 2011/0280561 A1 | 11/2011 | Geffert | |
| 2011/0293184 A1 | 12/2011 | Silverbrook | |
| 2011/0304705 A1 | 12/2011 | Kantor | |
| 2012/0008133 A1 | 1/2012 | Silny | |
| 2012/0201436 A1 | 8/2012 | Oakley | |
| 2012/0207404 A1 | 8/2012 | Robles-Kelly | |
| 2012/0224042 A1 | 9/2012 | Saijo | |
| 2012/0243009 A1 | 9/2012 | Chapman | |
| 2012/0281072 A1 | 11/2012 | Georgiev | |
| 2012/0307081 A1 | 12/2012 | Dewald | |
| 2012/0307137 A1 | 12/2012 | Chuang | |
| 2012/0321759 A1 | 12/2012 | Marinkovich | |
| 2013/0016415 A1 | 1/2013 | Kurtz | |
| 2013/0034266 A1 | 2/2013 | Shamir | |
| 2013/0054153 A1 | 2/2013 | Motl | |
| 2013/0063624 A1 | 3/2013 | Lin | |
| 2013/0088499 A1 | 4/2013 | Sato | |
| 2013/0172048 A1 | 7/2013 | Rodriguez | |
| 2013/0195273 A1 | 8/2013 | Lord | |
| 2013/0215168 A1 | 8/2013 | Furness | |
| 2013/0215596 A1 | 8/2013 | Holman | |
| 2013/0259320 A1 | 10/2013 | Gotanda | |
| 2013/0329006 A1 | 12/2013 | Boles | |
| 2013/0332367 A1 | 12/2013 | Quigley | |
| 2014/0063239 A1 | 3/2014 | Furness | |
| 2014/0072209 A1 | 3/2014 | Brumby | |
| 2014/0085534 A1 | 3/2014 | Bergquist | |
| 2014/0233015 A1 | 8/2014 | Mander | |
| 2015/0016711 A1 | 1/2015 | Tin | |

FOREIGN PATENT DOCUMENTS

| | | |
|---|---|---|
| WO | 2011017550 A2 | 2/2011 |
| WO | 2012002787 A1 | 1/2012 |
| WO | 2012020381 A1 | 2/2012 |
| WO | 2012047340 A1 | 4/2012 |

(56) References Cited

FOREIGN PATENT DOCUMENTS

| WO | 2013098708 A2 | 7/2013 |
|---|---|---|
| WO | 2013109934 A1 | 7/2013 |
| WO | 2013176900 A1 | 11/2013 |

OTHER PUBLICATIONS

Hayes, Next-generation cell phone cameras, Optics and Photonics News 23.2 (2012), pp. 16-21.

Karlen, et al, Design challenges for camera oximetry on a mobile phone, 2012 Annual Int'l Conference of IEEE Engineering in Medicine and Biology Society.

Park, et al, "Multispectral Imaging Using Multiplexed Illumination," in Computer Vision, 2007. ICCV 2007. IEEE 11th International Conference on , vol., no., pp. 1-8.

Tominaga, et al, Spectral imaging by synchronizing capture and illumination, JOSA A 29.9 (2012), pp. 1764-1775.

Bolle, et al., 'VeggieVision: A Produce Recognition System', Proceedings of the Third IEEE Workshop on 30 Applications of Computer Vision, pp. 224-251, 1996.

Chi, et al, Multi-spectral imaging by optimized wide band illumination, International Journal of Computer Vision 86.2-3 (2010), pp. 140-151.

Everdell, et al, Multispectral imaging of the ocular fundus using LED illumination, European Conference on Biomedical Optics, Optical Society of America, 2009.

Han, et al Fast Spectral Reflectance Recovery Using DLP Projector, Computer Vision—ACCV, pp. 323-335, 2010.

Kawakami, et al, High-Resolution Hyperspectral Imaging via Matrix Factorization, IEEE Conf. on Computer Vision and Pattern Recognition (CVPR) 2011.

Lee et al, Fast Model-Based Multi-Spectral Imaging Using Non-negative Principal Component Analysis, Optics Letters, vol. 37, No. 11, Jun. 1, 2012, pp. 1937-1939.

Nieves, et al., Multispectral synthesis of daylight using a commercial digital CCD camera Aoolied Ootics 44.27 (2005V 5696-5703.

PCT International Search Report of the International Searching Authority, PCT/US2013/040392 (published as WO2013176900), dated Nov. 28, 2013.

Richards, et al, Low-cost laser speckle contrast imaging of blood flow using a webcam, Biomedical Optics Express 4.10 (2013), pp. 2269-2283.

Schockling, et al, Visualization of hyperspectral images, SPIE Defense, Security, and Sensing, 2009.

Shrestha, et al, LED Based Multispectral Film Scanner for Accurate Color Imaging, IEEE Eighth International Conference on Signal Image Technology and Internet Based Systems, 2012. c.

Solovchenko, et al, Non-destructive estimation pigment content ripening quality and damage in apple fruit with spectral reflectance in the visible range, Global Science Books, 2010.

Nature's Color Identifier, The ChromaID Story, Visualant, Jan. 24, 2013.

Office Action dated Mar. 6, 2015, in U.S. Appl. No. 13/969,422.

International Search Report and Written Opinion dated Oct. 24, 2014 from PCT/US2014/041417.

International Search Report and Written Opinion dated Nov. 4, 2014 from PCT/US2014/050573.

Willis et al., 'InfraStructs: Fabricating Information Inside Physical Objects for Imaging in the Terahertz Region', ACM Transactions on Graphics, vol. 32, No. 4, Jul. 1, 2013.

Final Office Action in U.S. Appl. No. 13/840,451 dated Jan. 7, 2015.

Silverbrook Research U.S. Appl. No. 61/350,013, filed May 31, 2010.

Office Action dated Jul. 17, 2013, in U.S. Appl. No. 13/444,521.

U.S. Appl. No. 13/840,451, filed Mar. 15, 2013.

U.S. Appl. No. 13/888,939, filed May 7, 2013.

PCT Written Opinion of the International Searching Authority, PCT/US2013/040392 (published as WO2013176900), dated Nov. 21, 2014.

U.S. Appl. No. 14/836,878, filed Aug. 26, 2015.

Rocha, Hauagge, Wainer, Goldenstein. "Automatic fruit and vegetable classification from images", Computers and 15 Electronics in Agriculture, 70, 96-104, 2010.

Pandey et al., 'Image Processing and Machine Learning for Automated Fruit Grading System: A Technical Review', International Journal of Computer Applications (0975-8887), vol. 81—No. 16, Nov. 2013.

Zhang and Wu, "Classification of Fruits Using Computer Vision and a Multiclass Support Vector Machine", Sensors, pp. 12489-12505, 2012.

International Search Report and Written Opinion dated Apr. 8, 2015 in PCT/US14/66689.

Srinivasan, Shobha. "Statistical Texture Analysis", Proceedings of World Academy of Science, Engineering and Technology, pp. 1264-1269, 2008.

Arivazhagan, Shebiah, Nidhyanandhan, Ganesan."Fruit Recognition using Color and Texture Features", Journal of Emerging Trends in Computing and Information Sciences, pp. 90-94, 2010.

First Action Interview Pilot Program Pre-Interview Communication in U.S. Appl. No. 14/836,878.

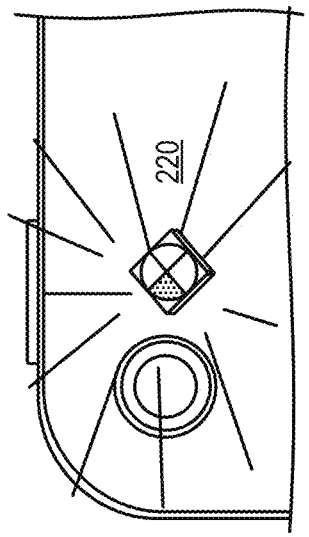
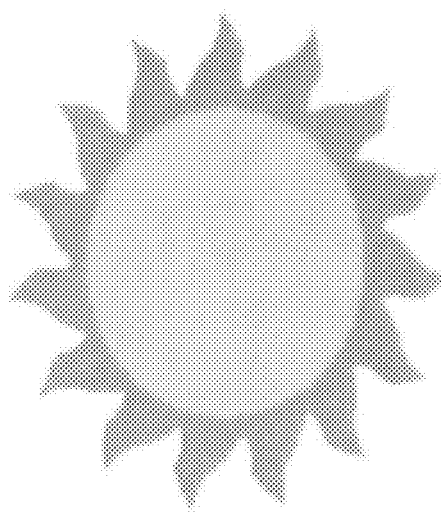
FIG. 26

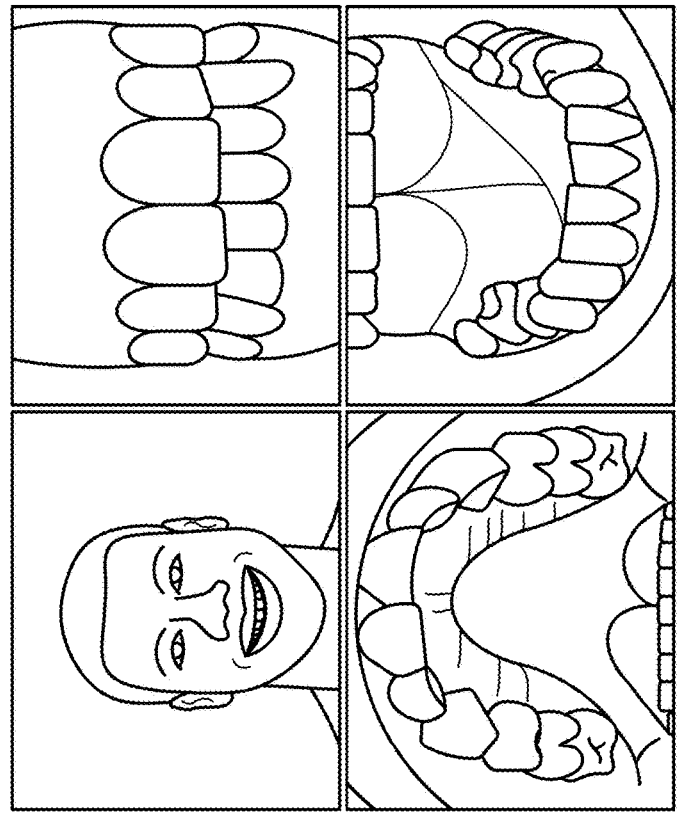
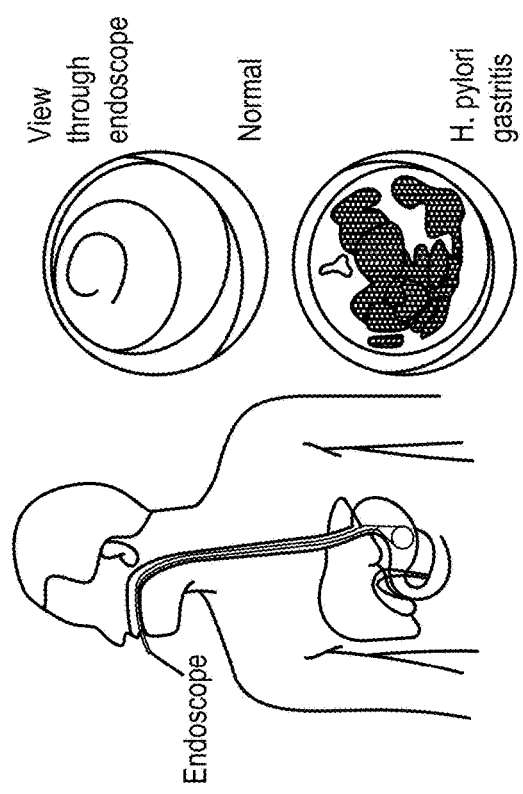
FIG. 27

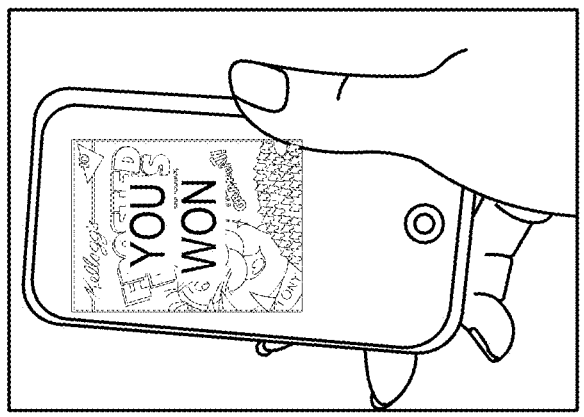
CMYK/other 'Revealed' Hidden Graphics
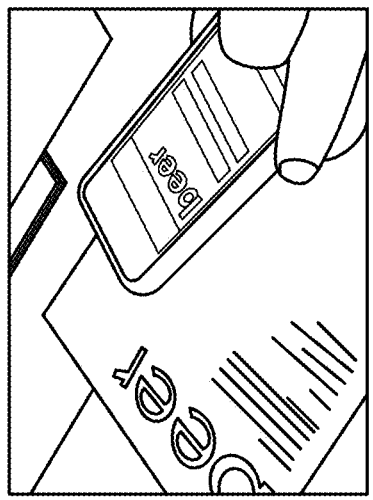
Advanced Chroma Digital Watermarking
FIG. 29

Ambient Light

Ambient Light Spectrum
$\sum_{i}^{n} A_i O_i$  310

LED Lighting
$\sum_{i}^{n} L_i O_i$  320

Three Sensor Types of the Bayer Pattern $\sum_{i}^{n} Red_i O_i$
$\sum_{i}^{n} Green_i O_i$   330
$\sum_{i}^{n} Blue_i O_i$ Illumination is now $(A_i + L_i/\text{dist-squared})$ And detected by three different sensor types $\sum_{i}^{n} R_i O_i$  300
Surface Reflection Spectral Curve Reflective Object

FIGURE 37

$$\Delta d_{red} = \sum_{i}^{n} Red_i(A_i + L1_i)R_i - \sum_{i}^{n} Red_i A_i R_i = \sum_{i}^{n} Red_i L1_i R_i$$

$$\Delta d_{green} = \sum_{i}^{n} Green_i(A_i + L1_i)R_i - \sum_{i}^{n} Green_i A_i R_i = \sum_{i}^{n} Green_i L1_i R_i$$

$$\Delta d_{blue} = \sum_{i}^{n} Blue_i(A_i + L1_i)R_i - \sum_{i}^{n} Blue_i A_i R_i = \sum_{i}^{n} Blue_i L1_i R_i$$

N-Dimensional Spectricity Vector Space

Powerful Classifier
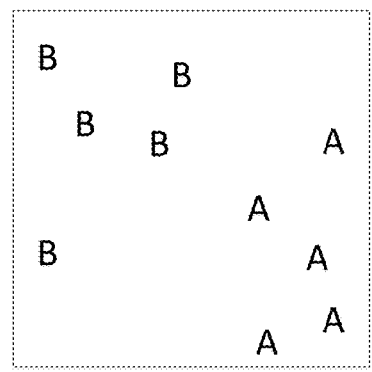
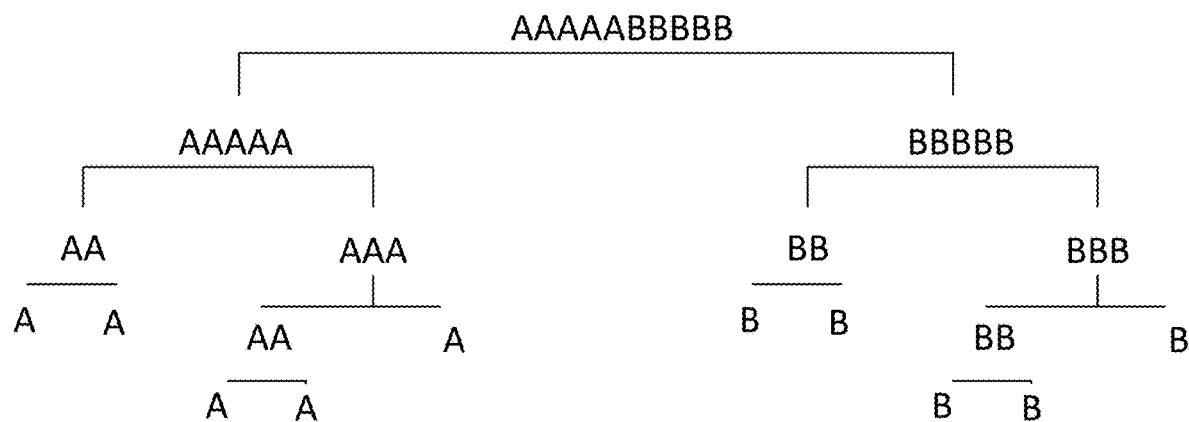
Fig. 61

Poor Classifier
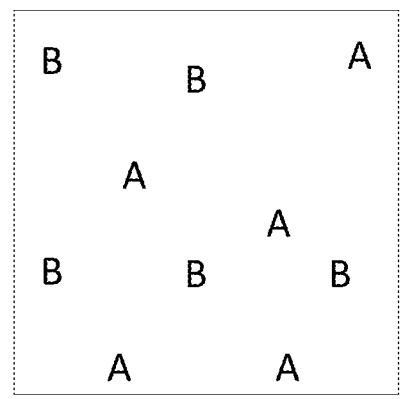
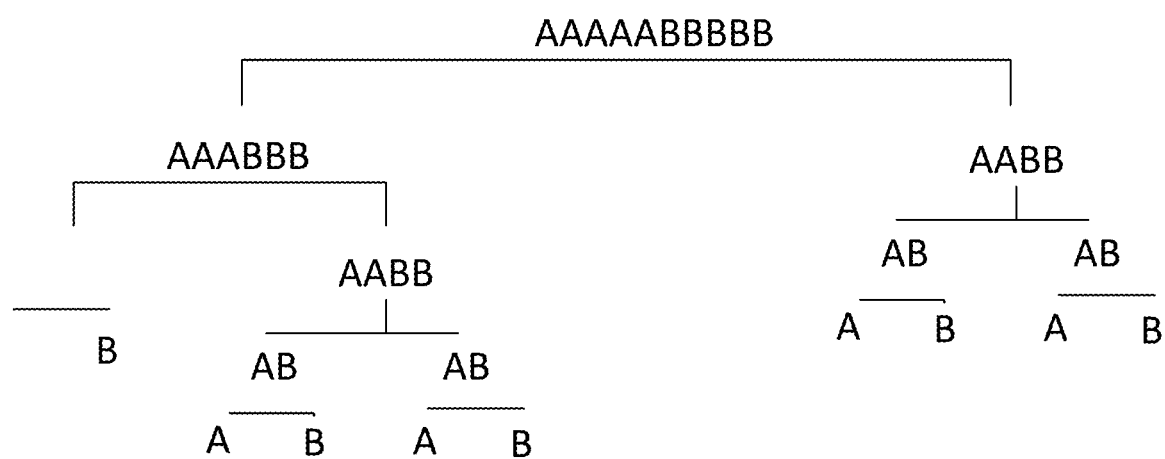
Fig. 62

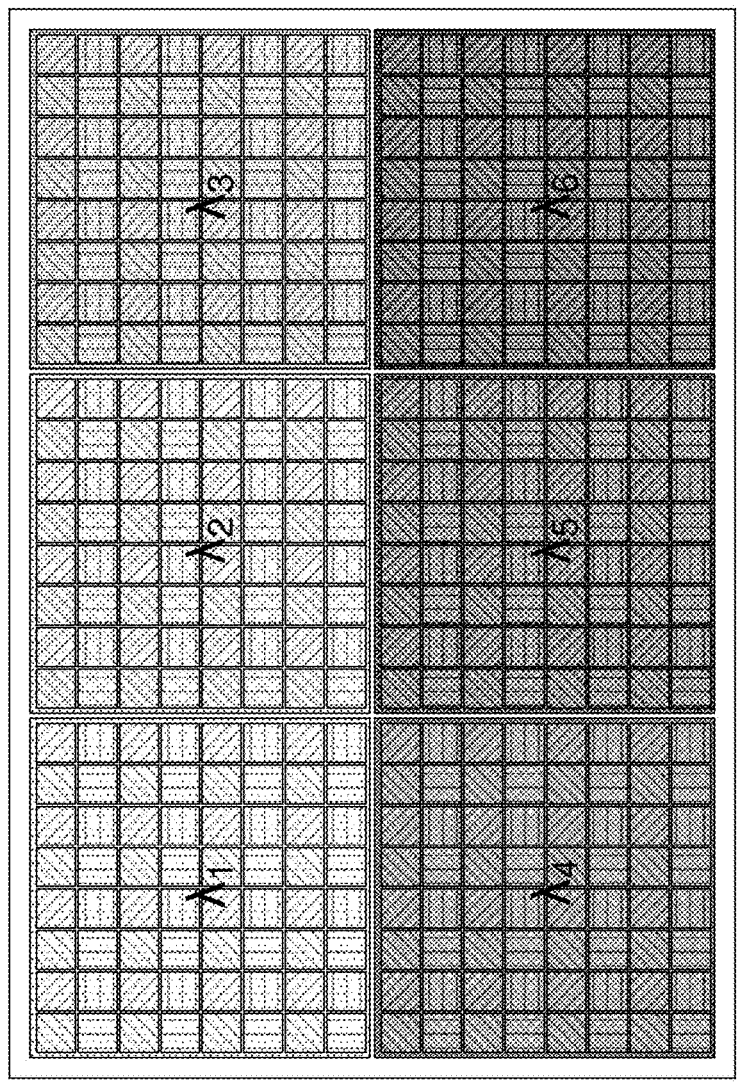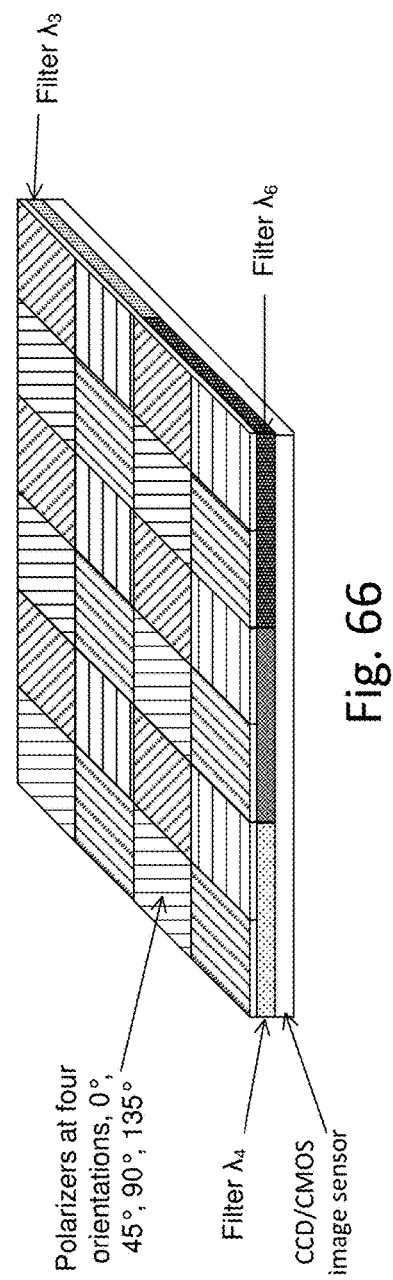
Fig. 66

SENSOR-SYNCHRONIZED SPECTRALLY-STRUCTURED-LIGHT IMAGING

RELATED APPLICATION DATA

This application is a continuation of Ser. No. 15/456,300, filed Mar. 10, 2017 (now patent Ser. No. 10/027,868), which is a continuation of Ser. No. 14/201,852, filed Mar. 8, 2014 (now U.S. Pat. No. 9,593,982), which is a continuation-in-part of Ser. No. 13/840,451, filed Mar. 15, 2013 (now U.S. Pat. No. 9,060,113), which is a non-provisional of provisional applications 61/688,722, filed May 21, 2012, and 61/706,982, filed Sep. 28, 2012. Application Ser. No. 14/201,852 also claims priority to provisional application 61/906,886, filed Nov. 20, 2013, and provisional application 61/907,362, filed Nov. 21, 2013, both with same title. These patents and applications are hereby incorporated by reference into this specification.

REFERENCE TO COMPUTER PROGRAM LISTING APPENDIX

This application includes a computer program listing appendix including the following Matlab computer program files: Spectricityv11_multiday_set2-code_appendix.txt (created on Nov. 19, 2013, file size of 33069 bytes), SpectraImg-code_appendix.txt (created on Nov. 18, 2013, file size of 9425 bytes) and spectraId-code_appendix.txt (created on Nov. 18, 2013, file size of 9233 bytes), configParser-code_appendix.txt (created on Nov. 18, 2013, file size of 1370 bytes), ClassifierTSVQ_appendix.txt (created on Mar. 7, 2014, file size of 7442 bytes), basicClassify_appendix.txt (created on Mar. 7, 2014, file size of 4386 bytes), and VQ_appendix.txt (created on Mar. 7, 2014, file size of 3759 bytes), all incorporated into this specification.

TECHNICAL FIELD

The present technology concerns, e.g., imaging spectrometry.

BACKGROUND AND INTRODUCTION OF THE TECHNOLOGY

Both natural light ('ambient') photography and flash-assisted (read broadly: 'human assisted light supplementation') photography have been around since the Daguerreotype. The present technology concerns how primarily the latter form of lighting, call it 'flash' for conciseness, can be so designed and implemented as to effectively qualify it within the general art of 'imaging spectrometry' or 'hyper-spectral imaging.'

In a nutshell, by illuminating a scene with several different brief (frame-synchronized) 'spectrally structured' light sources, even a common Bayer pattern CMOS camera can effectively become an imaging spectrometer with 'N bands,' N in very early days being practically on the order of 5 to 10 bands, but with fine prospects of going higher, especially as design principles behind Bayer patterns (and RGBW, e.g., from Sony) are reconsidered in light of this technology.

An introduction of the technology must make note of multi-chip LEDs (see e.g. Edison's 2012-era Federal FM series, depicted in FIG. 7) as being at least a seed for just what the doctor ordered regarding 'spectrally structured light.' A core idea—and current preferred embodiment—is to synchronize pulsing of different LED light sources with individual frames of a CMOS sensor, thereby creating the informational basis for N-band imaging. Light sources other than LEDs can certainly be considered but by 2012 standards, multi-chip and/or 'dual' LEDs are leading candidates to realize this technology.

A particularly intriguing choice of 'bands' is the 3 very well-known 1931 CIE color matching functions and/or their orthogonally transformed functions. With such choices, the stage is set for taking the beyond-religiously-fervent universe of color photography to its multiverse destiny: blandly referred to as 'direct chromaticity capture' in this disclosure.

The bulk of this disclosure zooms in on the design principles and physical realizations of turning virtually any electronic imaging sensor into an imaging spectrometer via specific coordination with some supplemental light source. With the core 'how' then elucidated, four essentially discrete applications will be presented and described, including A) the niche application of hyper-spectral imaging, B) the medical imaging potential of this technology, C) the previously alluded-to culturally-volatile topic of radically improved color photography for both 'digital cameras' and smart phones (as 2012 still draws pretty sharp lines between the two), and D) uses of N-band imaging within the mature technology of digital watermarking and 'image fingerprinting.'

Subsequent to the initial disclosure, this disclosure has been expanded significantly in several areas, including:
methods and systems for classifying and recognizing various types of objects;
such systems employing various imaging configurations, with various options on spectral light sources, optical filters, polarimetric sensing, sensing of these spectral and polarimetric pixel samples at 3 spatial dimensions (including plenoptic sensing and Kinect 3D structure sensing), scanning techniques, and synchronizing controlled capture under various lighting and sensing states;
training and applying classifiers for particular fields, including produce identification, produce ripening;
advances in illumination, sensing and post processing to address various environmental effects, including specular reflections, product package layers (e.g., plastic packaging or bags that hamper object identification); and
advances in sensing and post processing, prior to training and applying a classifier to obtain vectors per pixel, that combine spectral, polarimetric, and spatial relationships among pixel elements.

Many more system configurations, lighting and sensing devices, and pixel post processing techniques and device configurations are detailed further below. A myriad of inventive combinations of these and other aspects of the disclosure are contemplated and not limited to the particular example embodiments. We provide source code samples as examples. It is contemplated that the various signal processing described may be implemented as software instructions for execution on general purpose computing devices or special purpose processors, including devices with DSPs, GPUs, etc. These software instructions may be ported into processor device specific firmware versions, ASICs, FPGAs, etc. in various combinations, as well as leverage cloud computing services for execution (particular for training, classifying and recognition services).

The foregoing and other features and advantages of the present technology will be more readily apparent from the following Detailed Description, which proceeds with reference to the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 26 delves further into ambient illumination combined with the LED illumination.

FIG. 27 illustrates uses of the technology in medical applications.

FIG. 29 illustrates use of the technology in digital watermarking and related applications.

FIG. 37 details how unknown ambient lighting spectral coefficients can be removed from aggregate mathematical equations.

FIG. 46 depicts green LED differential lighting of some white paper sheets.

FIG. 47 depicts the same scene as FIG. 46, but now differentially lit by a blue LED one frame in a video sequence later, where the pulsing of the LEDs are coordinated with the framing of a camera—a Bayer-pixel color camera in this case.

FIG. 48 depicts an iso-spectricity overlay image of the white sheets of paper, each separately illuminated by the 5 LEDs.

FIG. 55 is an image obtained from the same ambient lit scene as FIG. 54 but now with the 'differential tweak' of the blue LED turned on.

FIG. 56 is an image obtained from the same ambient lit scene as FIG. 54 but now with the 'differential tweak' of the green LED turned on.

FIG. 61 illustrates an example of a strong classifier.

FIG. 62 illustrates an example of a weak classifier.

FIG. 66 is a diagram illustrating top and perspective views of an image sensor with a polarizer per pixel element, and optical band pass filter per 2D block of pixel elements.

Figure 1:
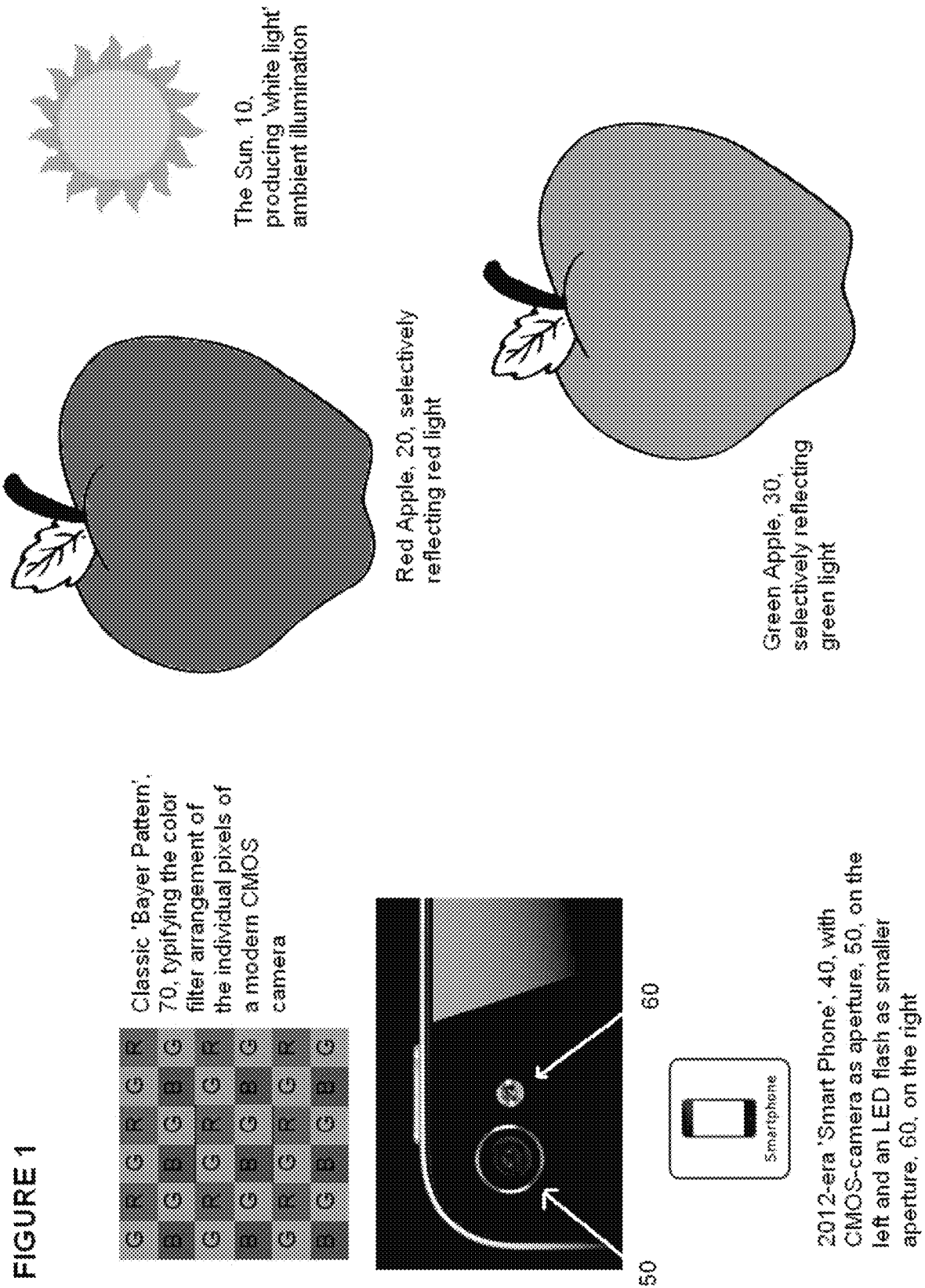
FIG. 1 illustrates how most modern cameras distinguish red apples from green apples.

The following provides additional descriptions of selected figures:

FIG. 1 shows, at 70, a classic "Bayer Pattern," typifying the color filter arrangements of the individual pixels of a modern CMOS camera. Below is shown part of a 2012-era smartphone 40, with a CMOS camera aperture 50, and an LED flash aperture 60. Also shown are two apples, a red apple 20 and a green apple 30, respectively reflecting red and green light from the sun 10 (which produces "white light" ambient illumination).

Figure 3:
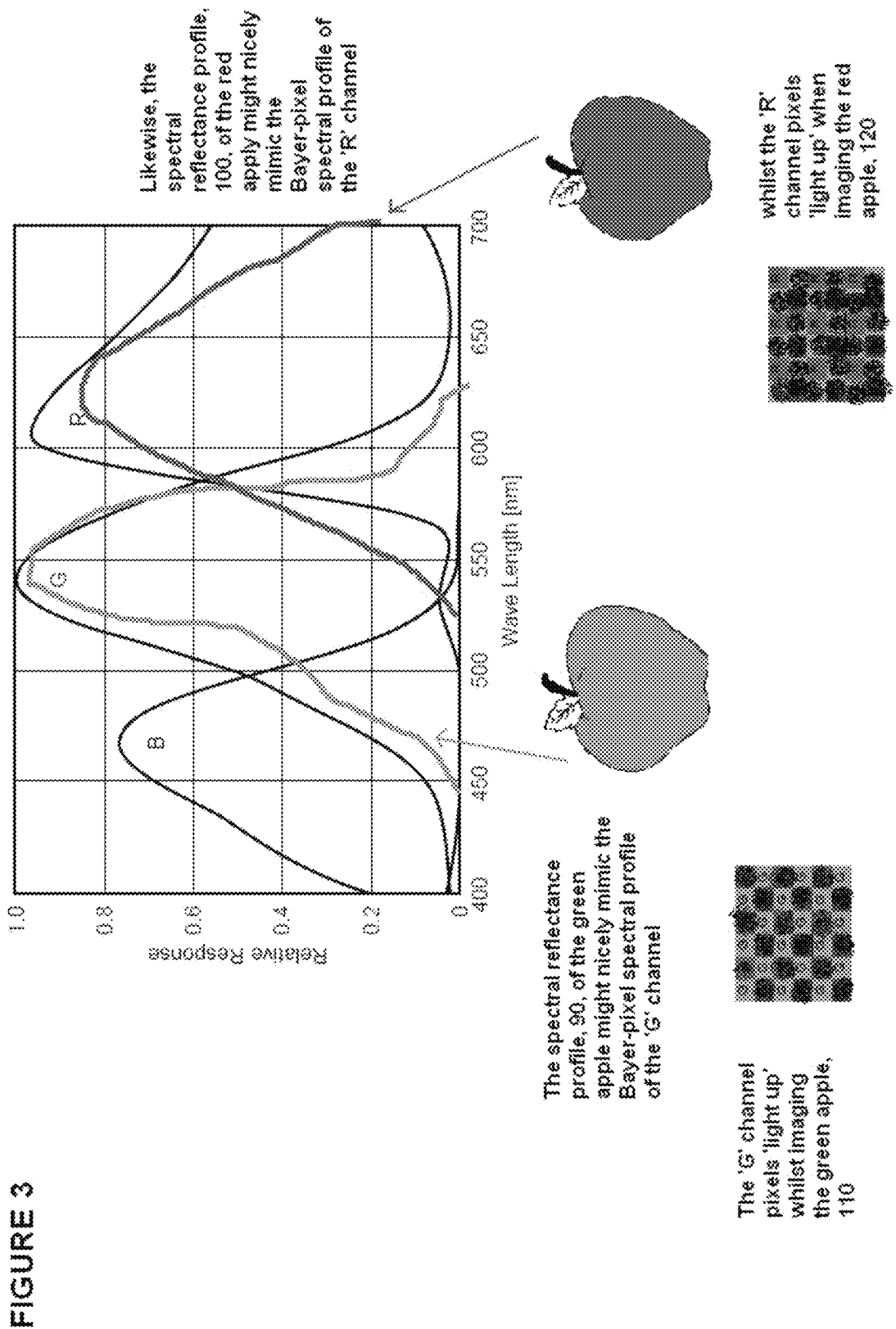
FIG. 3 is similar to FIG. 1 but includes information about an idealized spectral reflectance profile of a green apple, and of a red apple.

FIG. 3 shows how the spectral reflectance profile, 90, of the green apple might nicely mimic the Bayer-pixel spectral profile of the "G" channel. In the lower left, the "G" channel pixels "light up" whilst imaging the green apple 110. Likewise, the spectral reflectance profile 100 of the red apple might nicely mimic the Bayer-pixel spectral profile of the "R" channel. In the lower right, the "R" channel pixels "light up" when imaging the red apple 120.

Figure 4:
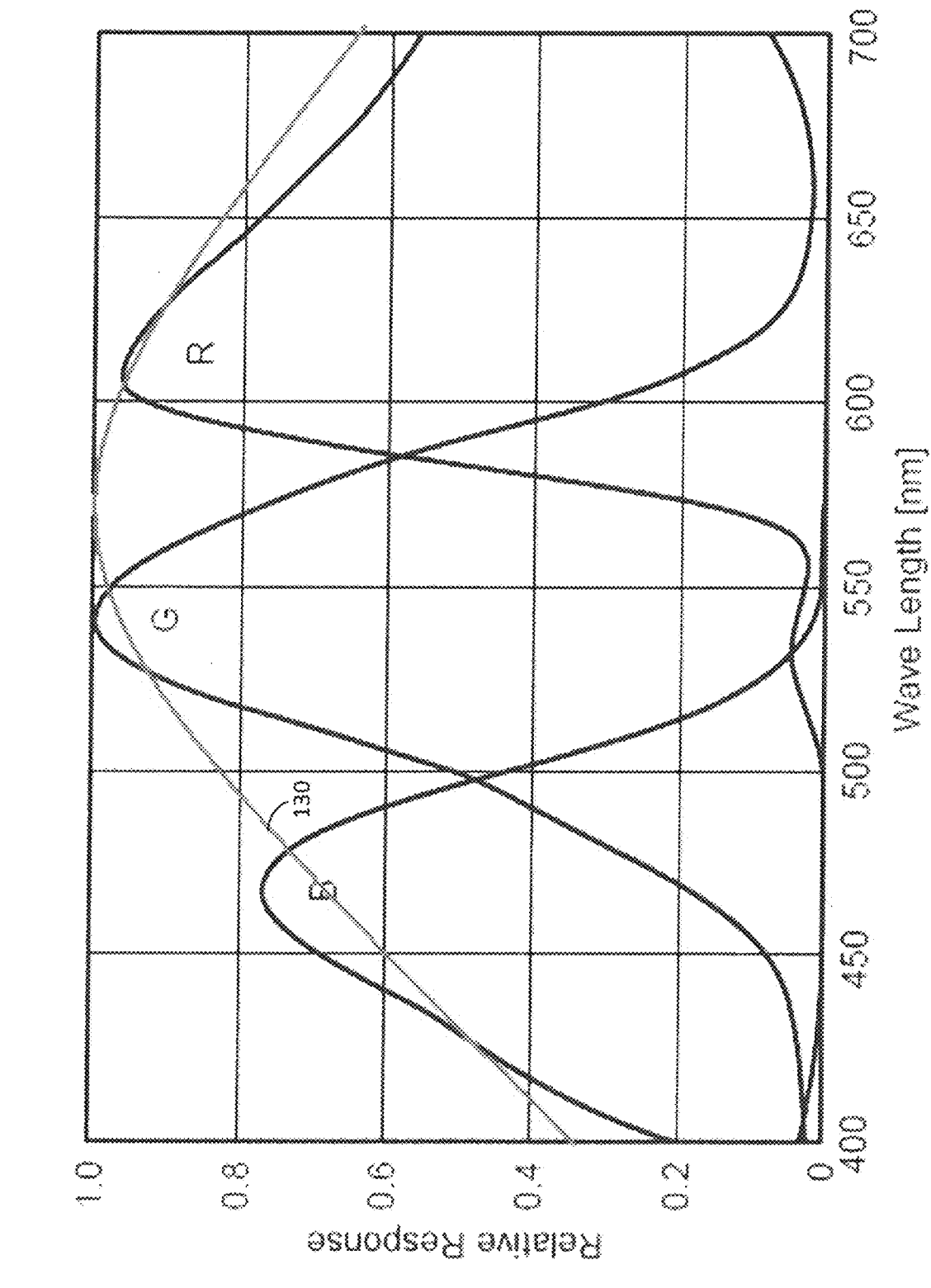
FIG. 4 introduces an idealized ambient lighting source spectral curve.

FIG. 4 concerns the fact that a scene is effectively never illuminated with strictly "white light." There is always a "structure" to the light spectral curve—illustrated in very simple fashion in this figure. In particular, curve 130 shows the "actual" but largely "unknown" ambient lighting spectral profile of a scene (the apples).

Figure 5:
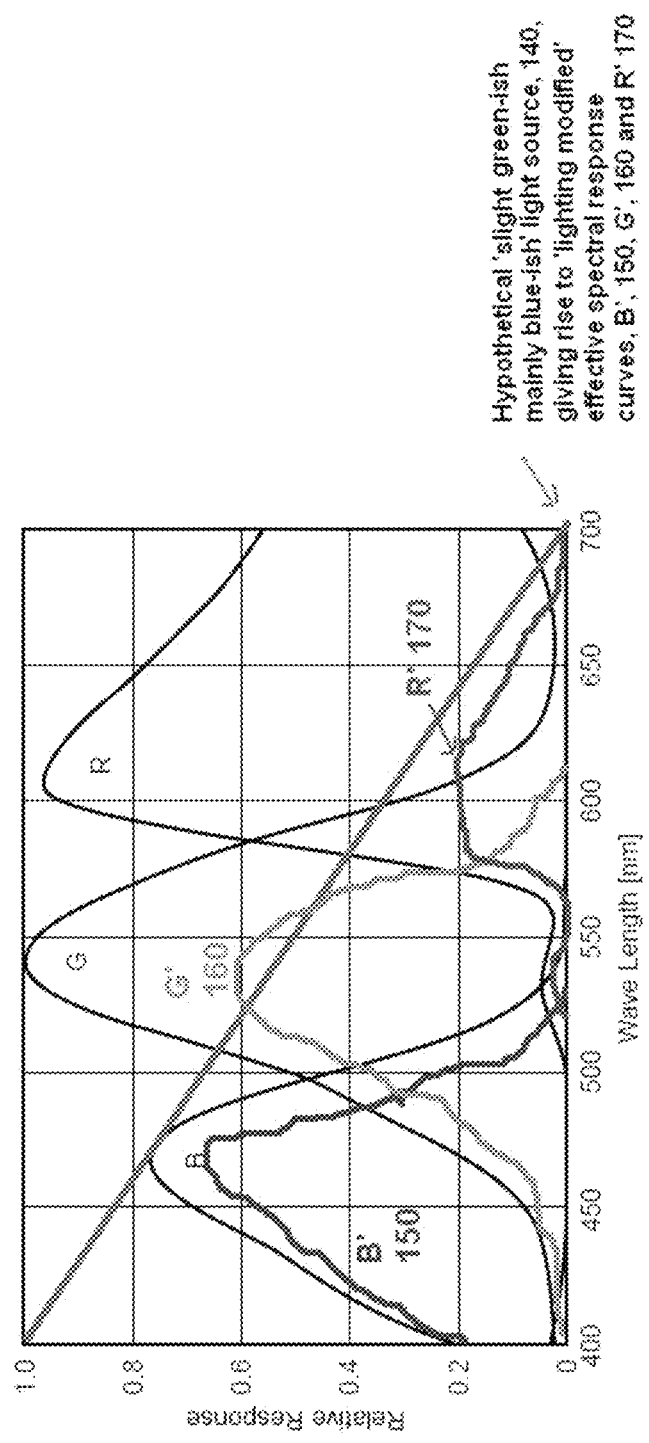
FIG. 5 presents a case involving slight green-ish, mainly blue-ish illumination.

FIG. 5 illustrates a hypothetical "slight green-ish, mainly blue-ish" light source, 140, giving rise to "lighting modified" effective spectral response curves B', 140, G', 160 and R' 170.

Figure 6:
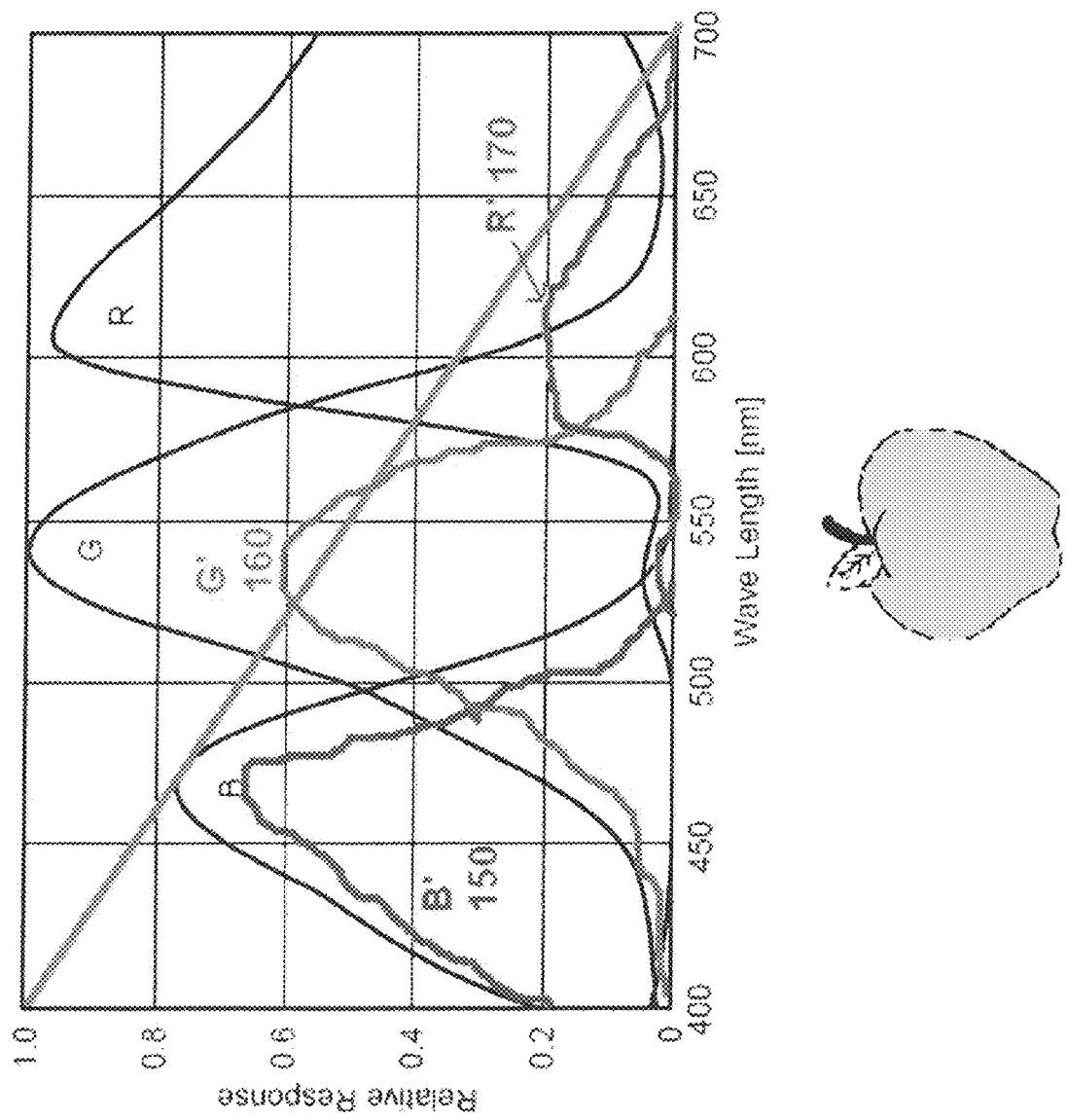
FIG. 6 shows how an apple may be mis-colored when rendered on a screen, due to illumination.

FIG. 6 shows how the red apple will "look" yellowish, 180—a pretty even combination of green and red—under the lighting conditions of the previous figure, all because of the different lighting and nothing to do with the sensors. The "effective" profiles B', G' and R' all get shaped by the knowable characteristics of the lighting.

Figure 7:
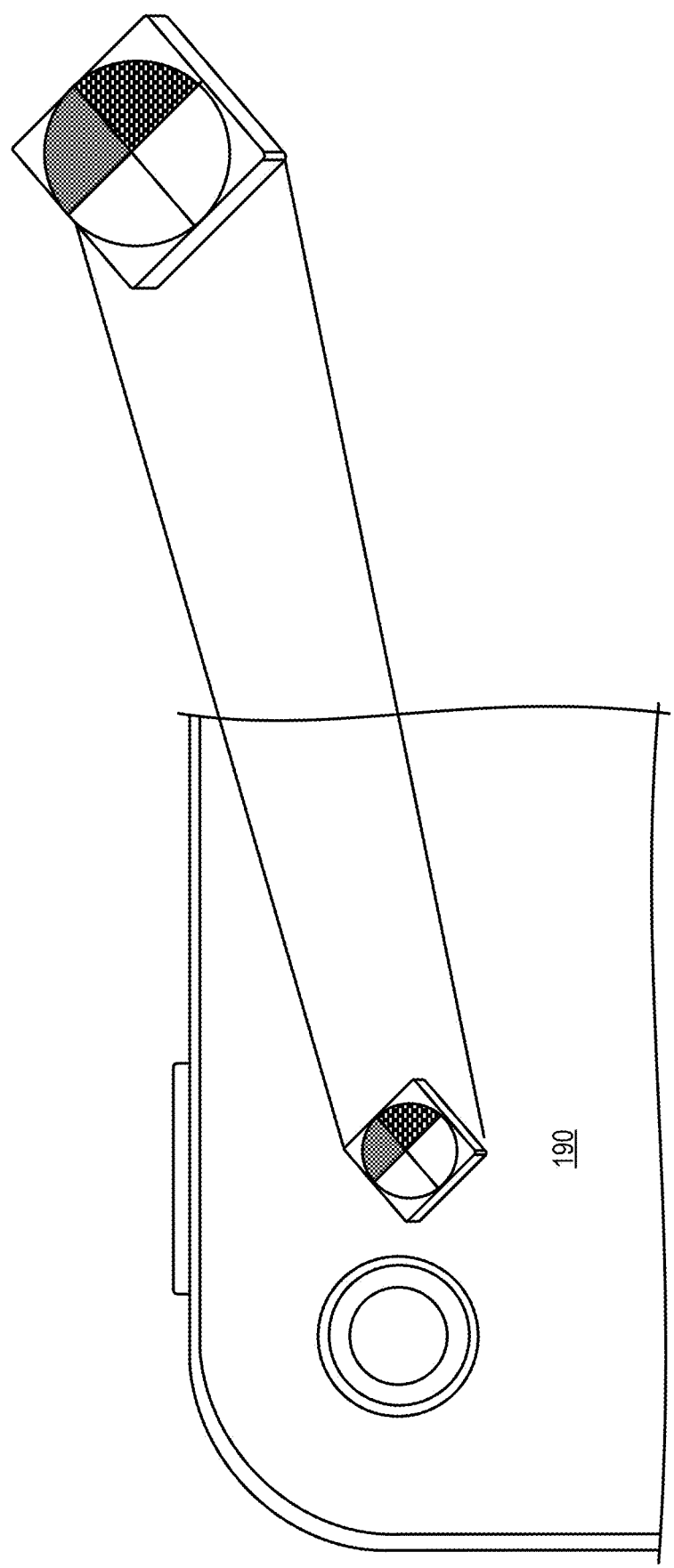
FIGS. 7 and 8 introduce the notion of multi-colored flash.

FIG. 7 shows that the "standard white" LEDs found in existing camera phone flashes can be replaced with so-called "Multichip LEDs," with the Edison Corporation Federal FM series model here depicted (190).

Figure 8:
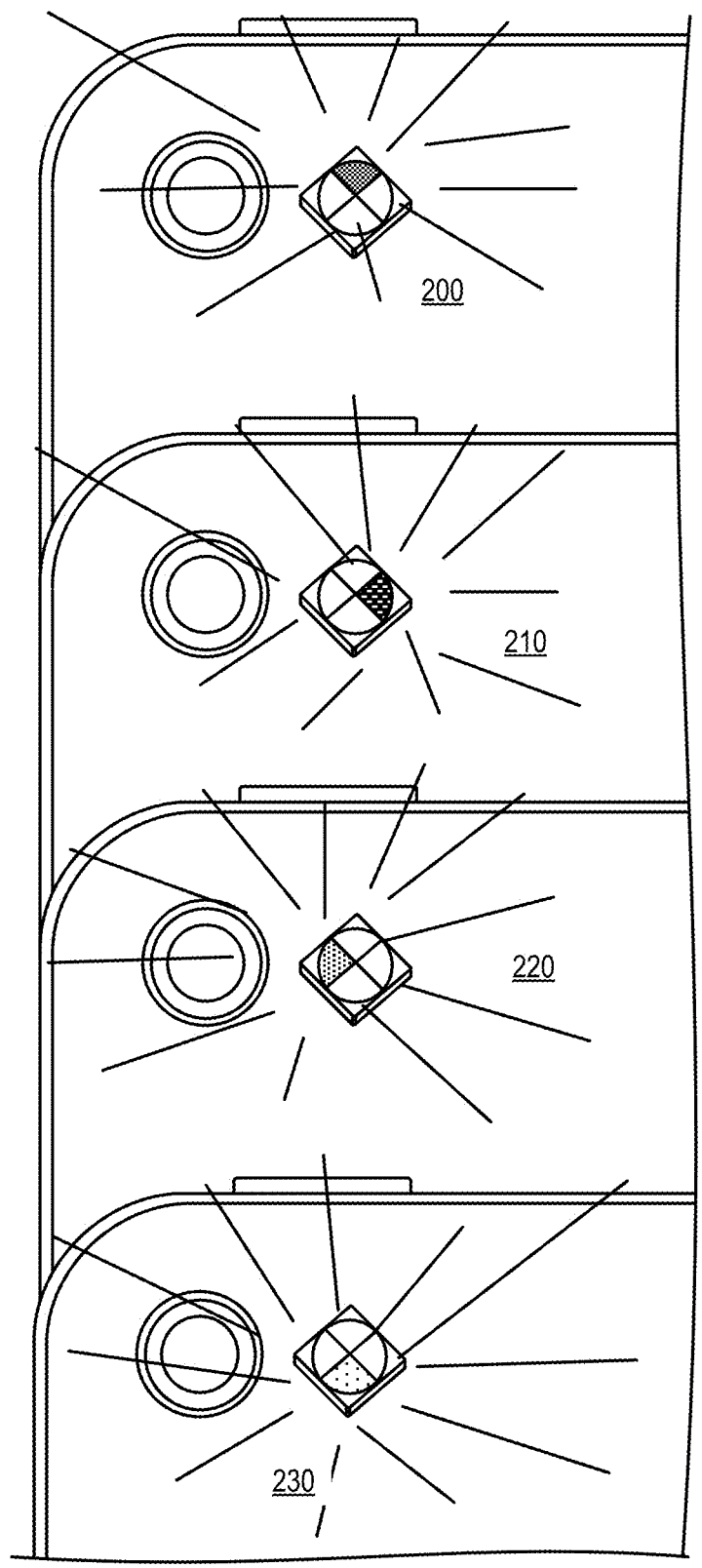

FIG. 8 shows how all of this, to the human eye, looks like a pseudo-strobe kind of white light illumination since it is cycling so quickly. In particular, starting with the top, coordinated with frame 4*n (n continuously increasing), one of the LED flashes for typically 1/30th of a second, 200, for example with a yellow-ish light, yet well known spectrally.

Below, sensor frame 4*n+1 then coordinates with another LED flashing for 1/30th of a second, 210, this time with a red-ish looking light, again with well known spectral characteristics. Then below, frame 4*n+2 witnesses a purplish LED flash, 220, tending more toward the bluish and green side of the spectrum. Finally, at the bottom, frame 4*n+3 has a mauvish LED flash with its exposure time of 1/30th of a second, completing the flash cycle and then incrementing "n" to go back to the top for movies, or stop for a single "image" capture (i.e., n=1 and only 1 for a single image).

Figure 11:
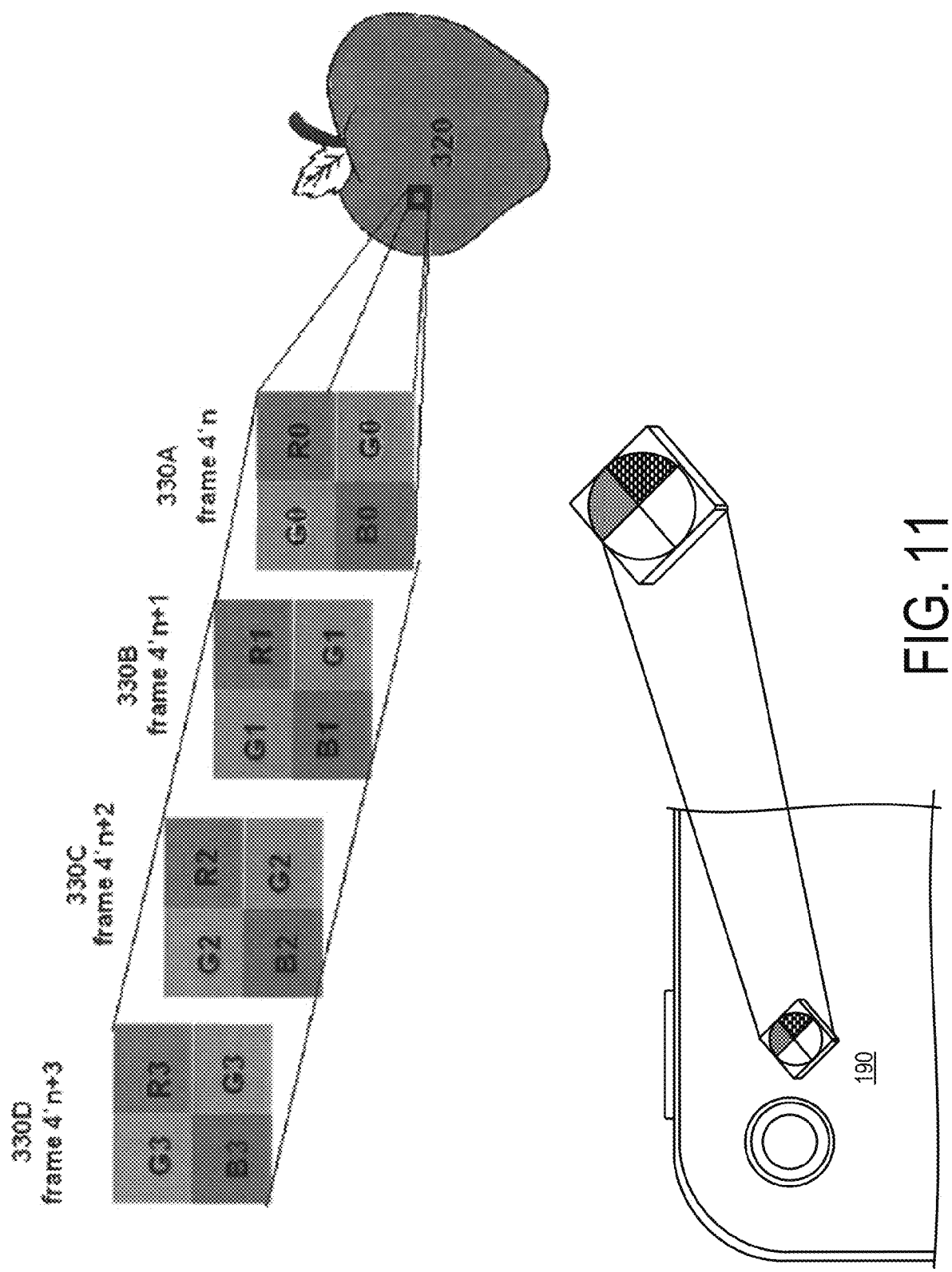
FIG. 11 illustrates different spectral samplings of an apple.

FIG. 11 illustrates how some small patch on the red apple, 320, corresponding to a Bayer cell, 330A-D, thus has effectively 12 different "spectral samplings" measured over four frames of image data, corresponding to B0, B1, B2, B3, G0, G1, G2, G3, R0, R1, R2 and R3. The Bayer cell is the same physical cell for all four frames, but with different lighting they have different effective spectral sampling profiles.

Figure 12:
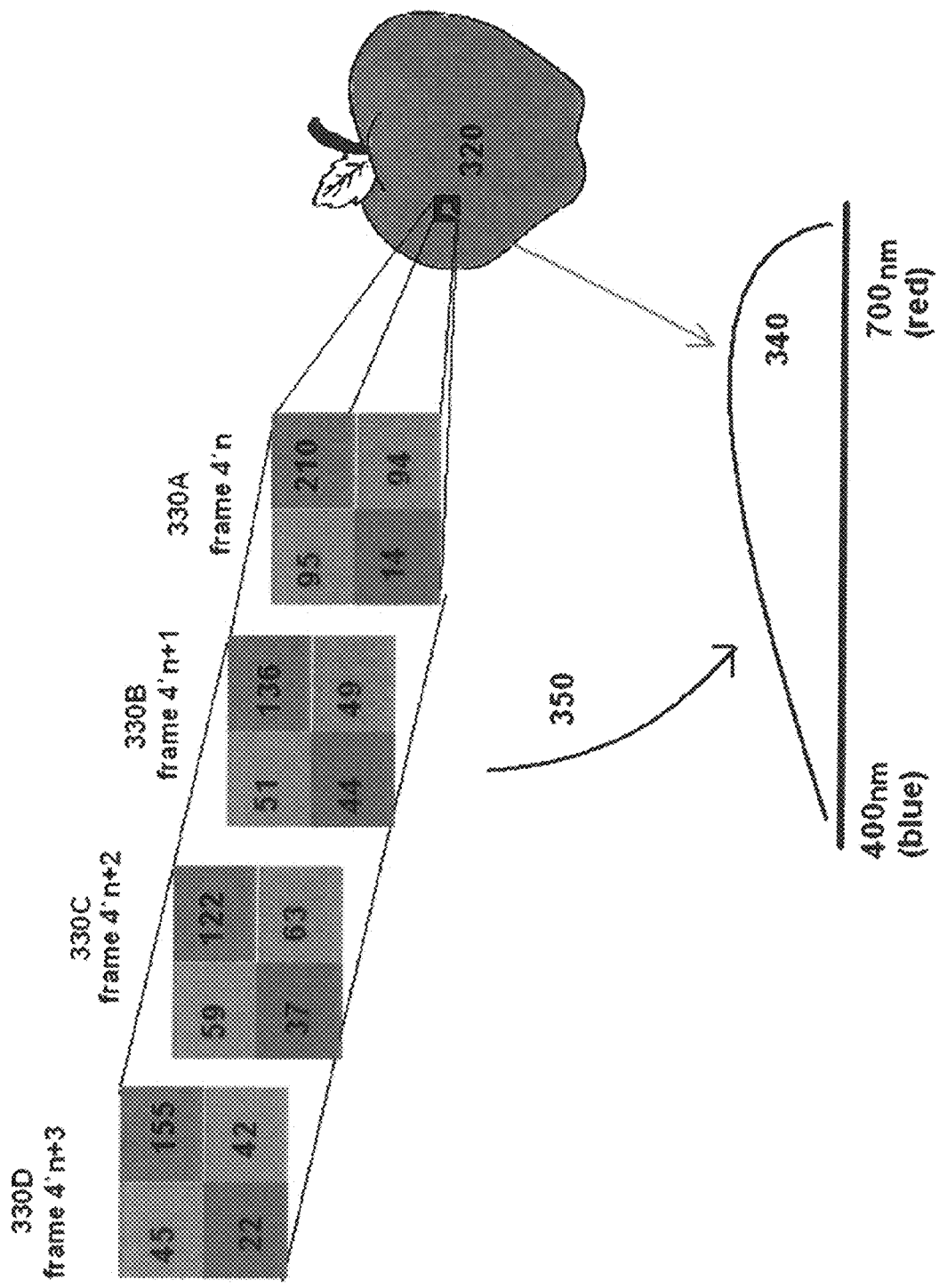
FIG. 12 illustrates how data gathered in FIG. 11 can be used to produce spectral information for the apple.

FIG. 12 examines how this sequence of digitized pixel values lets us try to measure the "unknown" spectral reflection function of the patch of apple being imaged, including a hypothetical "actual" spectral reflectance function 340 of the patch of apple 320.

Figure 13:
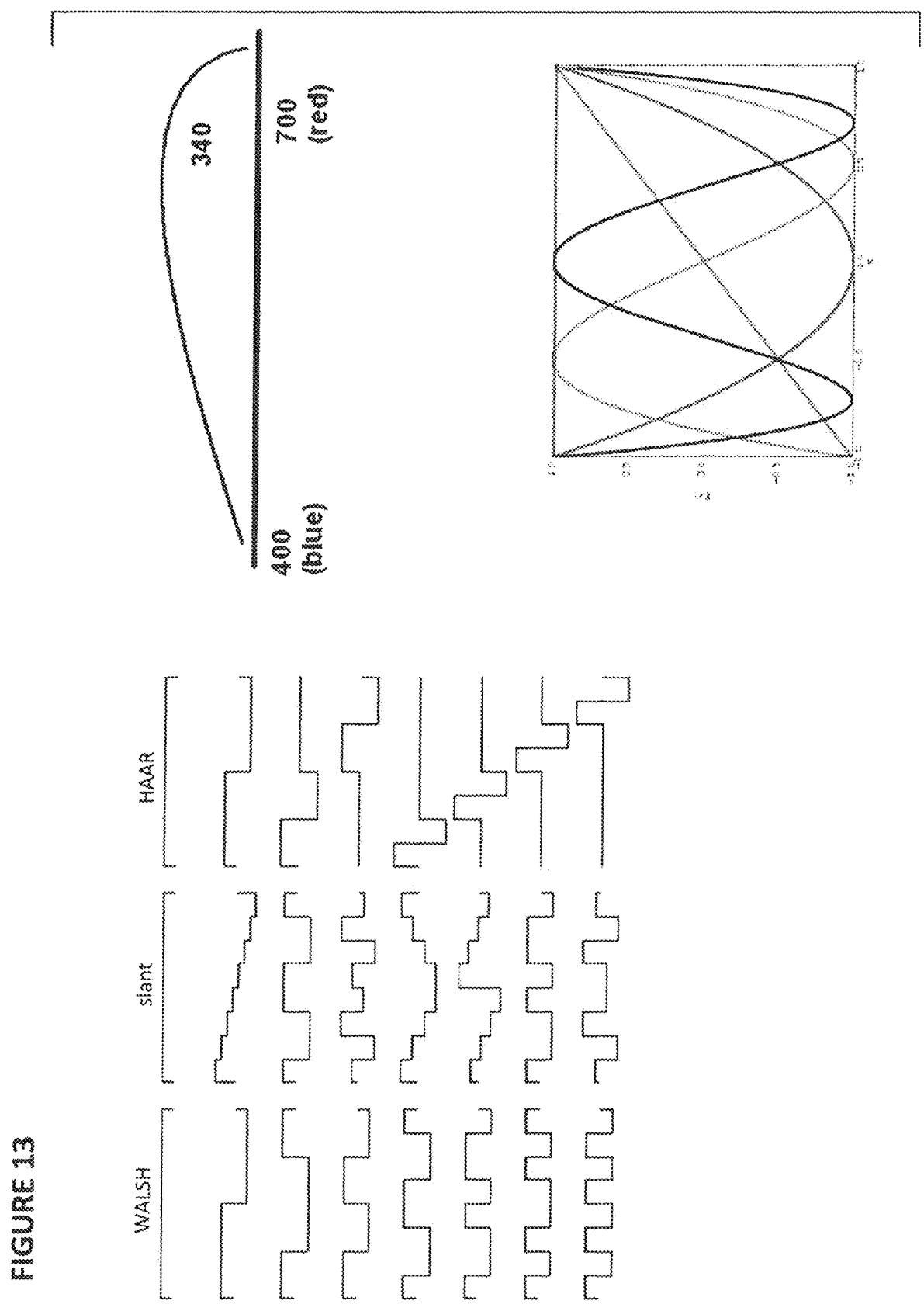
FIG. 13 shows a linear function estimation arrangement that can be used with the spectral information of FIG. 12.

FIG. 13 concerns generic linear functional estimation. The left side shows typical examples of orthogonal discrete functions often used to parameterize (fit) unknown distributions (the apple's true reflectance spectrum 340 in our example). The lower right shows that "smooth" functions can similarly be used, a la Chebyschev Polynomials.

Figure 14:
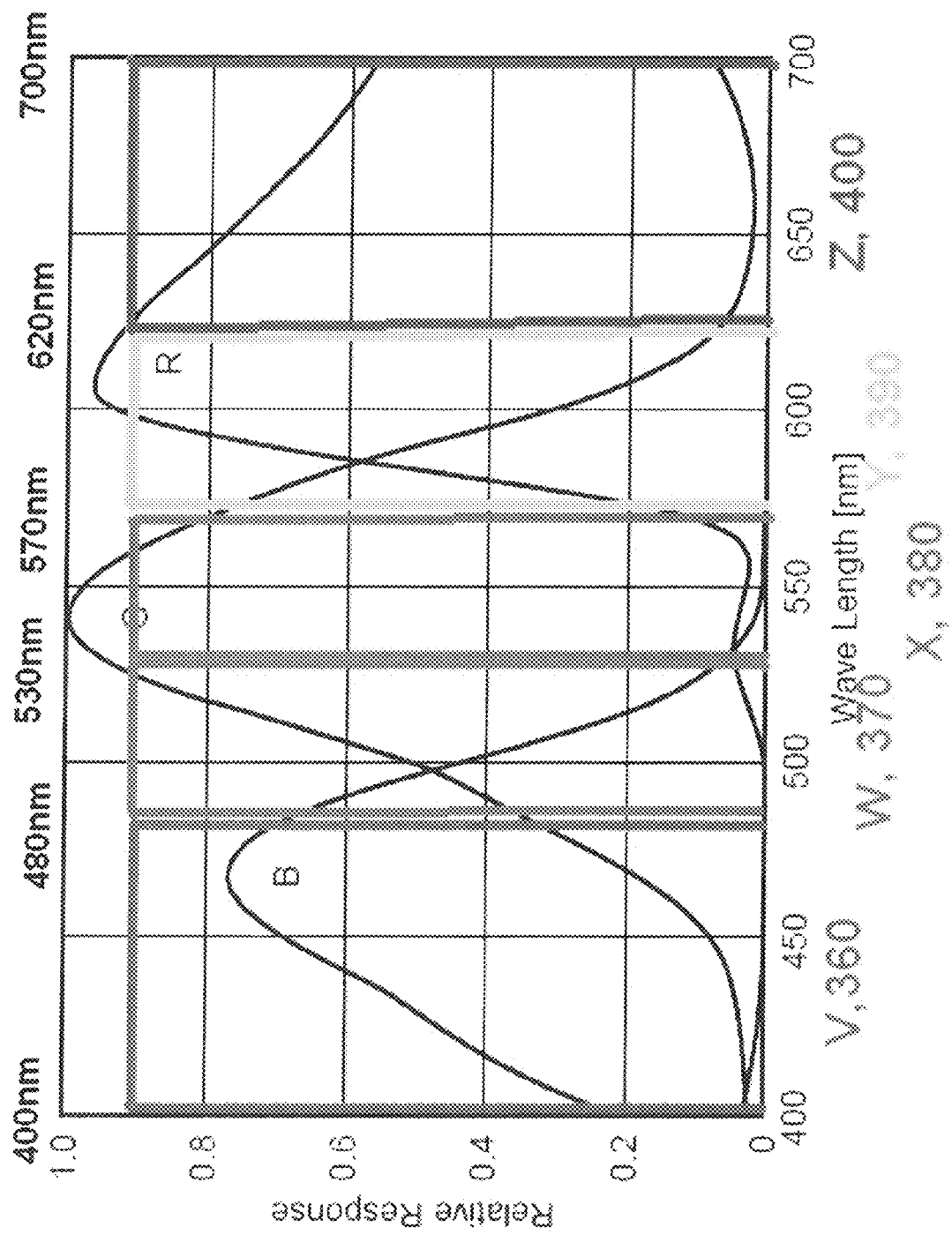
FIGS. 14-17 show the evolution from a five-band rectangular solution set to a linear algebra representation of the spectral data.

FIG. 14 shows a decent "5-rectangular band" Bayer-tuned Solution Set, with 80 nm, 50 nm, 40 nm, 50 nm and 80 nm bandwidths, respectively.

Figure 15:
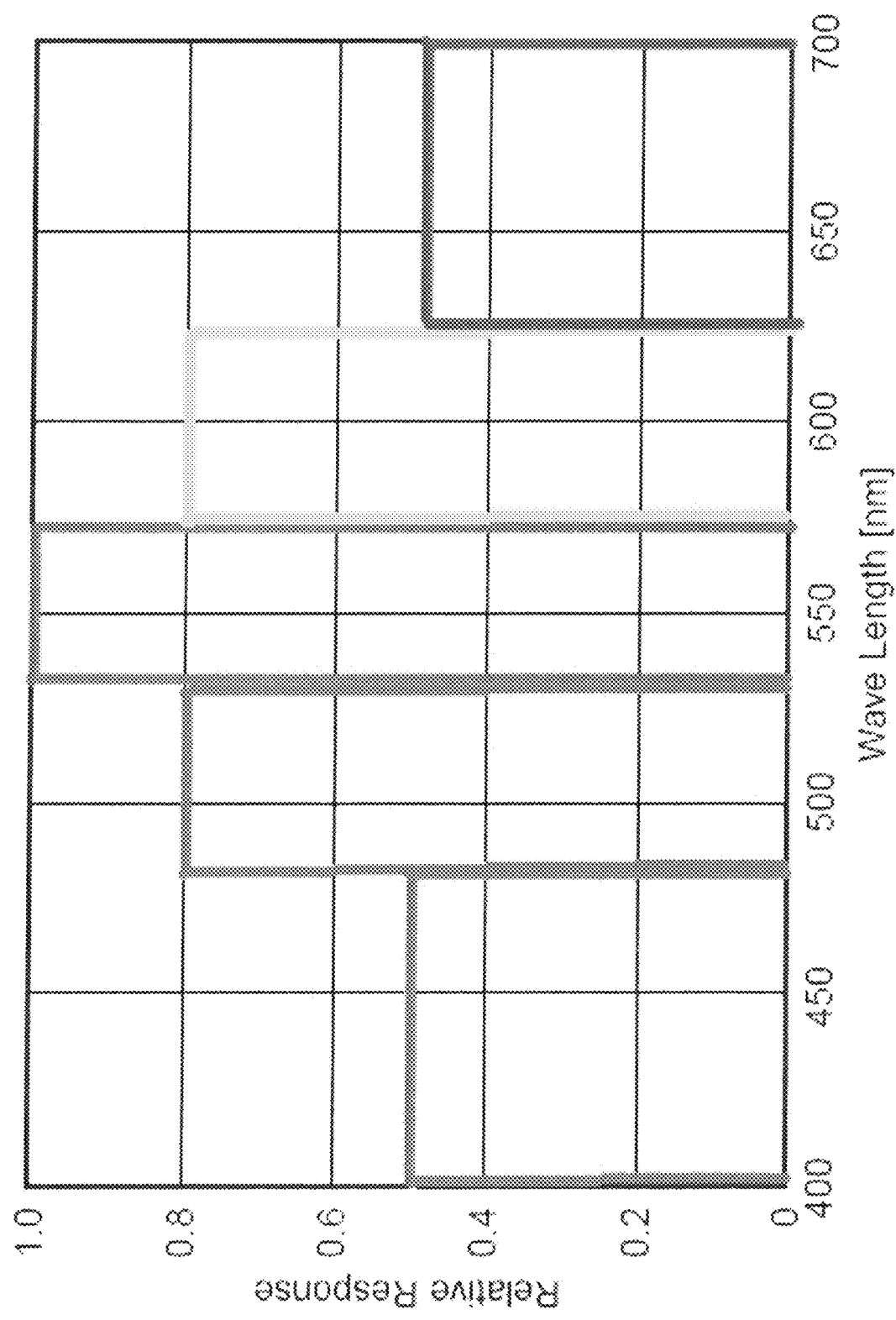

FIG. 15 shows a 5-band "Orthonormal" set of imaging spectroscopy bands, weighted for direct multiplication with the lighting-modified effective spectral response curves associated with B0-B3, G0-G3 and R0-R3.

Figure 16:
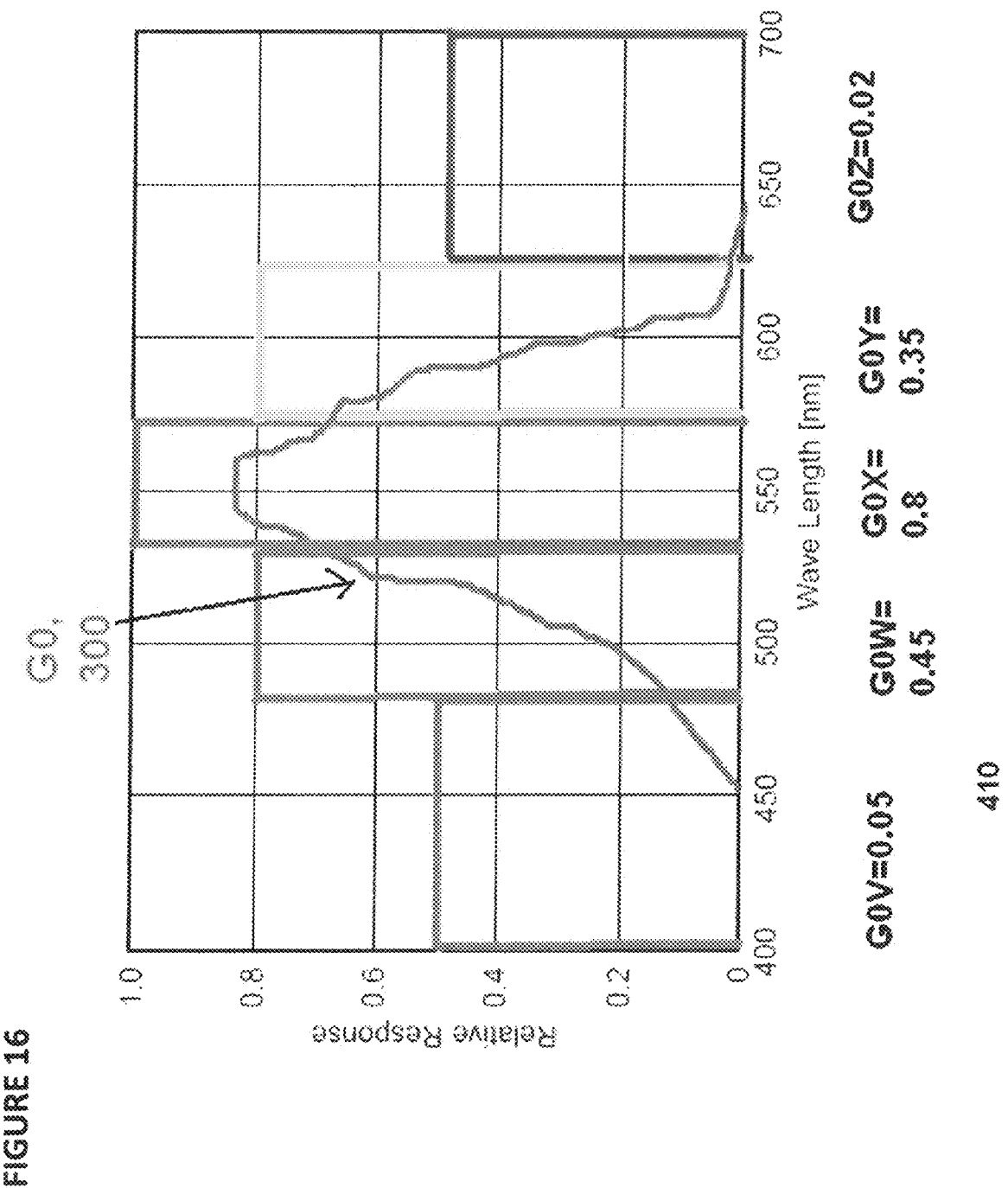

FIG. 16 shows largely empirical coupling value between effective spectral response G0 and all five chosen bands.

Figure 17:
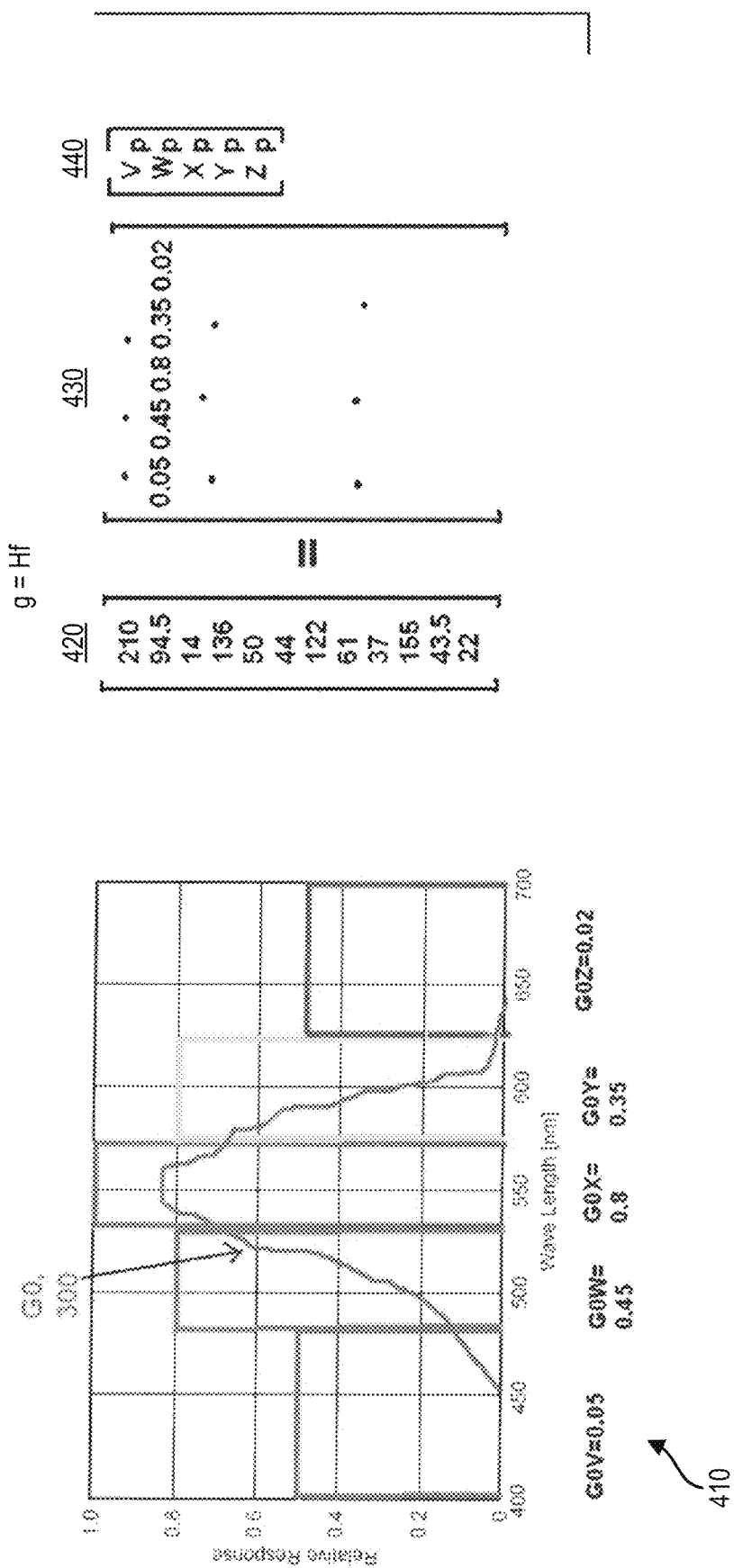

Referring to the left of FIG. 17, the "G0" row of the H matrix is calculated via simple area multiplications between an empirical light-source-modified sensor profiles and chosen solution bands (in the case V-Z). On the right, 'g' is the twelve pixel value vector (with the redundant green values averaged); H is the coupling matrix, and F is the sought solution. The G0 row vector is explicitly displayed, while the other 11 rows are implicitly filled-in by multiplying their effective response curves by the five orthonormal bands, as per FIG. 16. (The noted sub-script "p" indicates we are solving for our small apple patch.)

Figure 22:
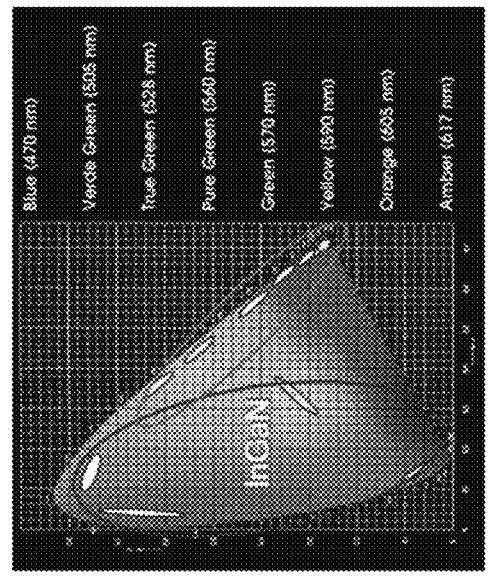

FIG. 22 shows various examples of LED spectral characteristics as plotted on the 1931 CIE spectral diagram.

Figure 24:
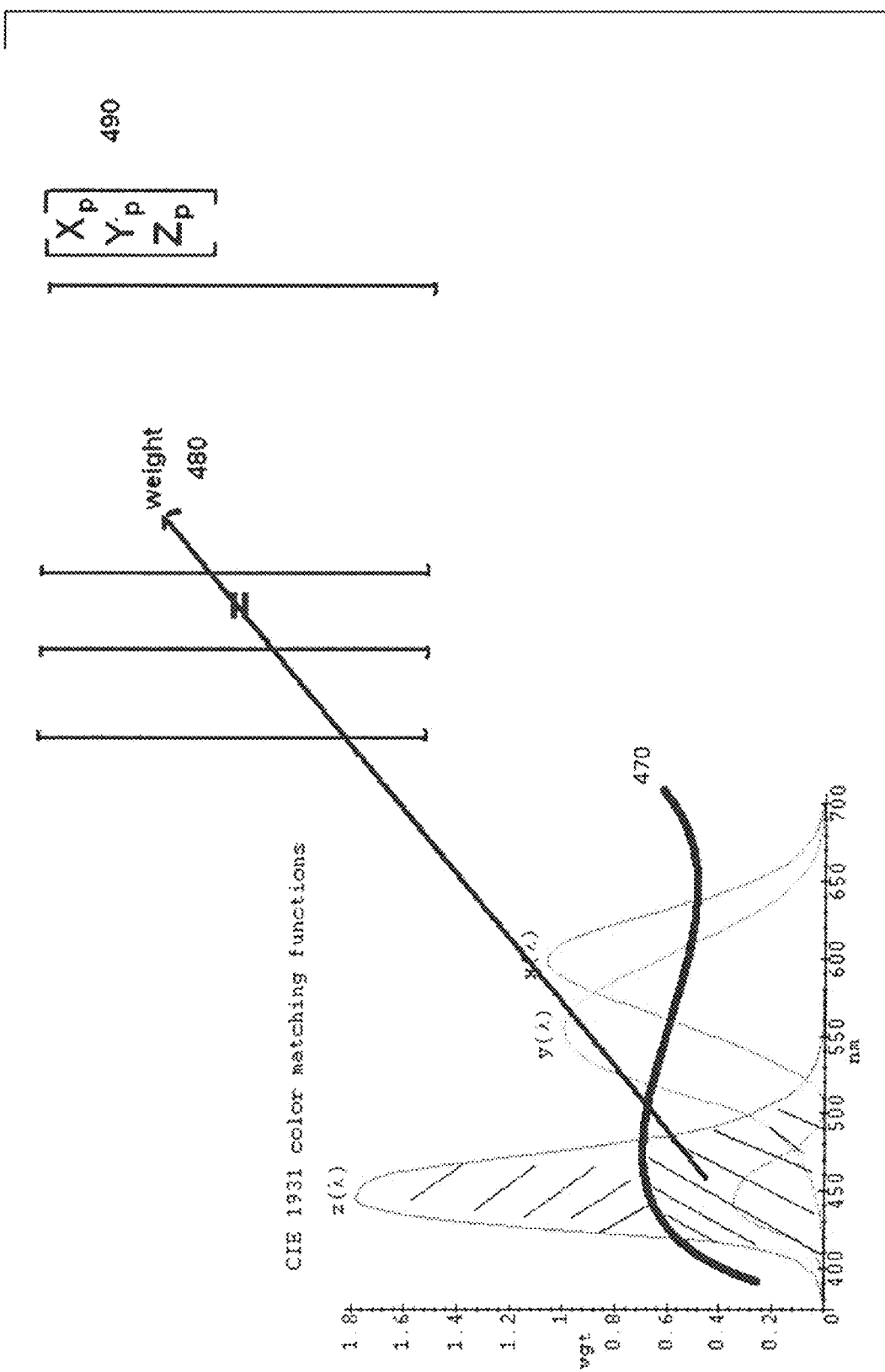
FIG. 24 details use of a CIE matrix to generate chromaticity coordinates.

FIG. 24 illustrates that solution bases functions can be many choices and not necessarily "orthogonal" or "orthonormal." Flash-modified pixel sensitivity functions also need not be Bayer/RGB/etc., as well. Here depicted is how explicit "CIE" solutions can be constructed from "arbitrary" flash-sensor profiles, where multiplication produces row values in our H matrix. Curve 470 shows an arbitrary flash-sensor profile to be multiplied by any chosen solution functions, here depicting "classic" 1931 CIE functions. (The subscript "p" again indicates we are solving for our small apple patch.)

Figure 25:
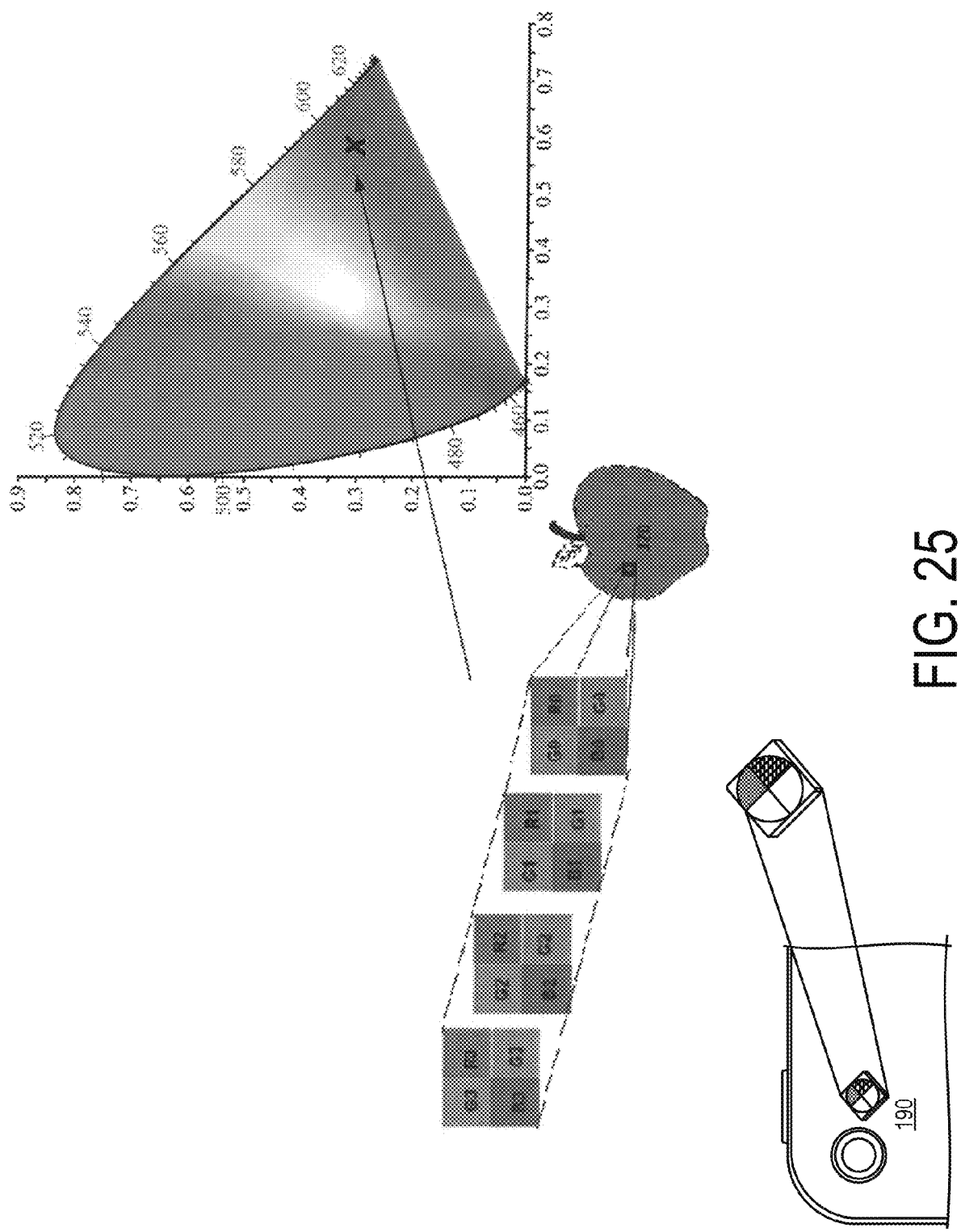
FIG. 25 shows how the present technology resolves an apple's color to particular coordinates on a chromaticity diagram.

FIG. 25 shows that "Direct Chromaticity Capture" becomes a natural consequence where (a) sensor profiles, (b) LED profiles, (c) "ambient light" treatment, and (d) the raw number of independent flashes . . . can all combine to approach near-full-gamut capture, and ever-tightening error bars on the capture.

FIG. 26 contemplates that there are many ways to deal with "generally unknown" but often very typical kinds of ambient light additions to the pure flash, e.g.:

1) add an estimated ambient profile to ALL weight values in the H matrix;

2) strobe the flash so quickly, with synchronized strobing of the pixel exposure time, that ambient becomes negligible;

3) EXPLOIT IT! Use a pure ambient capture as part of the frame sequencing, giving N-5 in our 4-LED scenario;

4) Use common photographic measuring instrumentation to gauge the color temperature of ambient, then use this in H matrix correction factors;

5) Use "Flash-Frame Intensity Modulation" to cycle the intensity of any/all flashes, measuring the digital number modulation of the resulting pixel values against a "known" lumen modulation applied to a scene;

6) Etc. . . .

Figure 28:
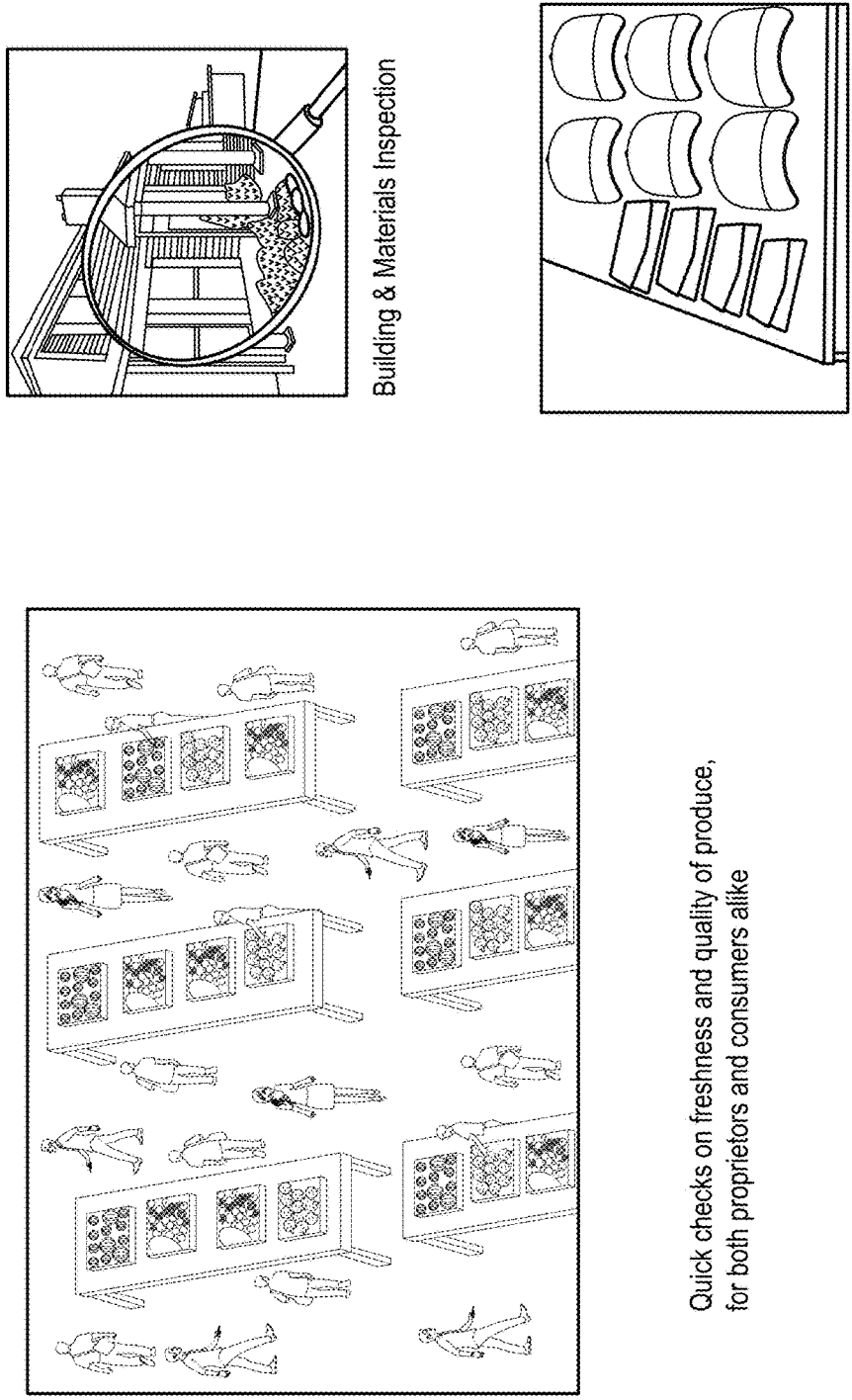
FIG. 28 introduces use of the technology in food safety, item inspection, and anti-counterfeiting applications.

FIG. 28 illustrates some of the commercial/consumer applications of the present technology, beyond "richest color" photography, e.g., quick checks on freshness and quality of produce, for both proprietors and consumers alike (281); building and materials inspection (282); and counterfeit products "quick checks" (283).

Figure 31:
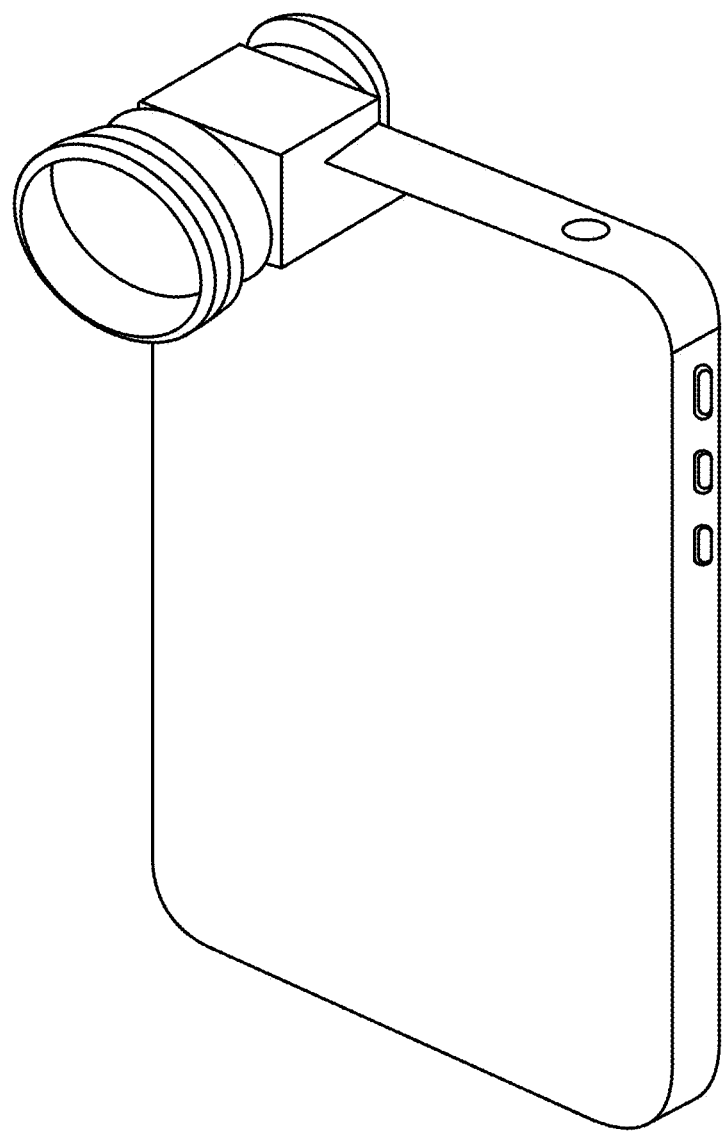
FIGS. 31 and 31A illustrate an implementation using a clip-on illumination accessory.

FIG. 31 illustrates how clip-on accessories are a viable short-cut to market as the long process of designing and integrating new LEDs directly into smart phones. (Depicted is a commercially available optic supplementation, but making this unit primarily a flash unit with either wired or wireless connection to the device is quite viable.)

Figure 32:
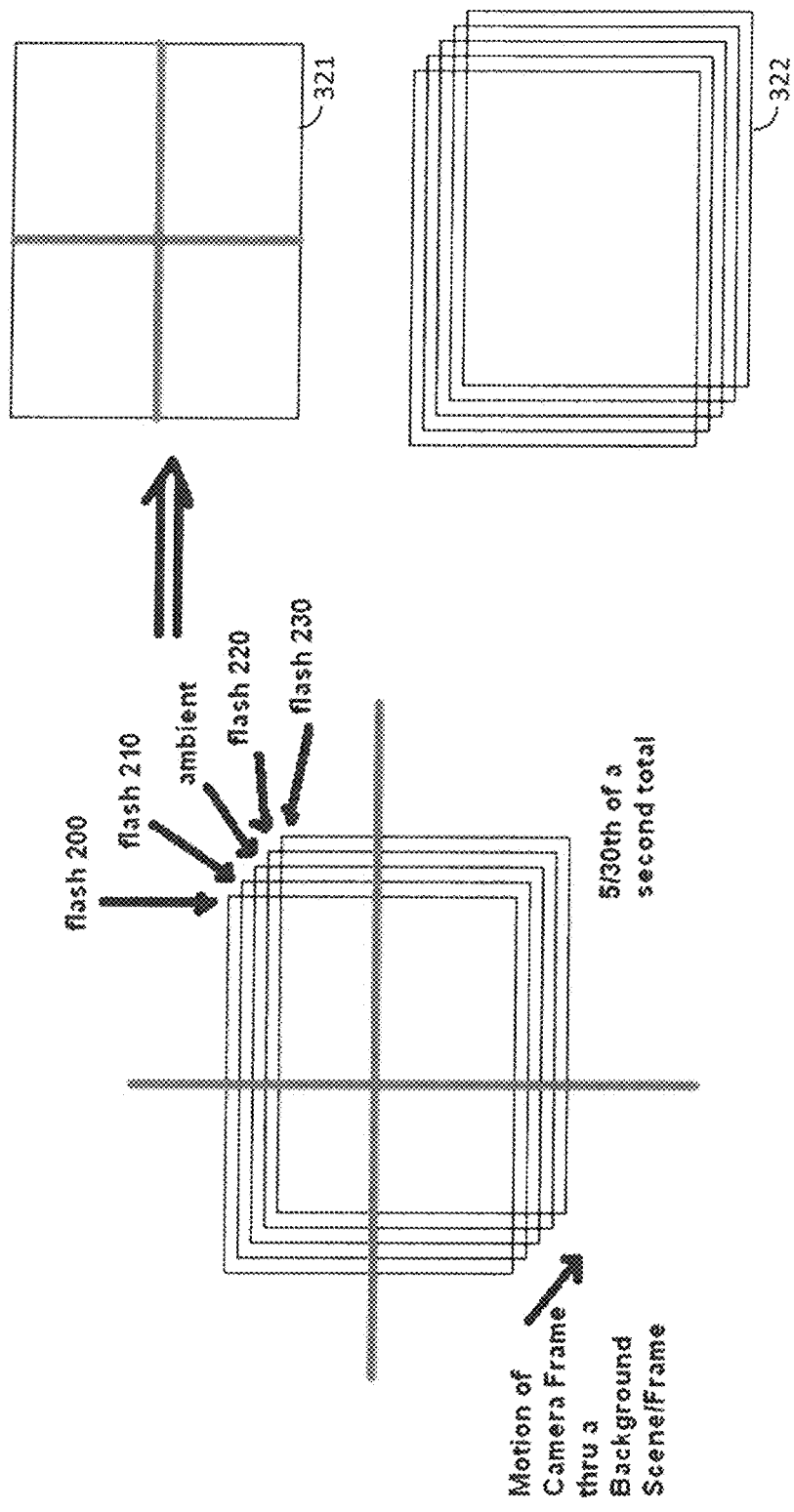
FIG. 32 addresses aspects of the technology concerning motion.

FIG. 32 illustrates an approach to deal with camera motion and motion photography (video; effectively motion deblurring in luminance, with the additional of chrominance "draping"). This involves dynamic linear luminance tracking (keying-in explicitly to time intervals between ⅕th and ¹/₁₀th of a second). At 321, "common" luminance-signal correlation can determine motion between frames, with subsequent re-projection of individual frames onto a shared frame—typically the middle frame. At 322, the same operation can be done on frames of a video; each individual frame can become a reference frame that the other four (in this example) re-project to.

Figure 35:
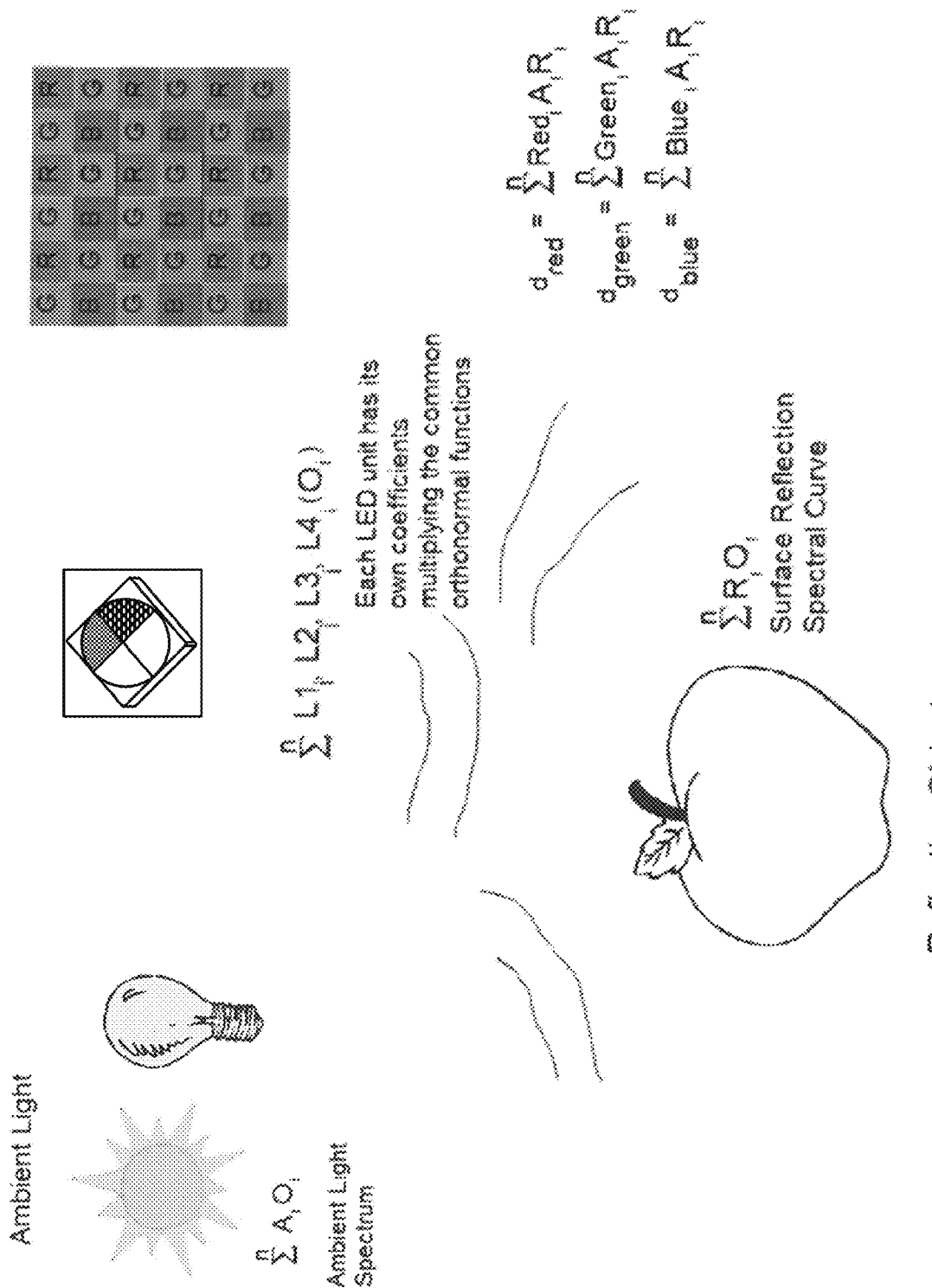

FIG. 35 posits that the LED units are not on, and a camera merely samples the ambient light, producing three datum per each cell of a Bayer sensor.

Figure 36:
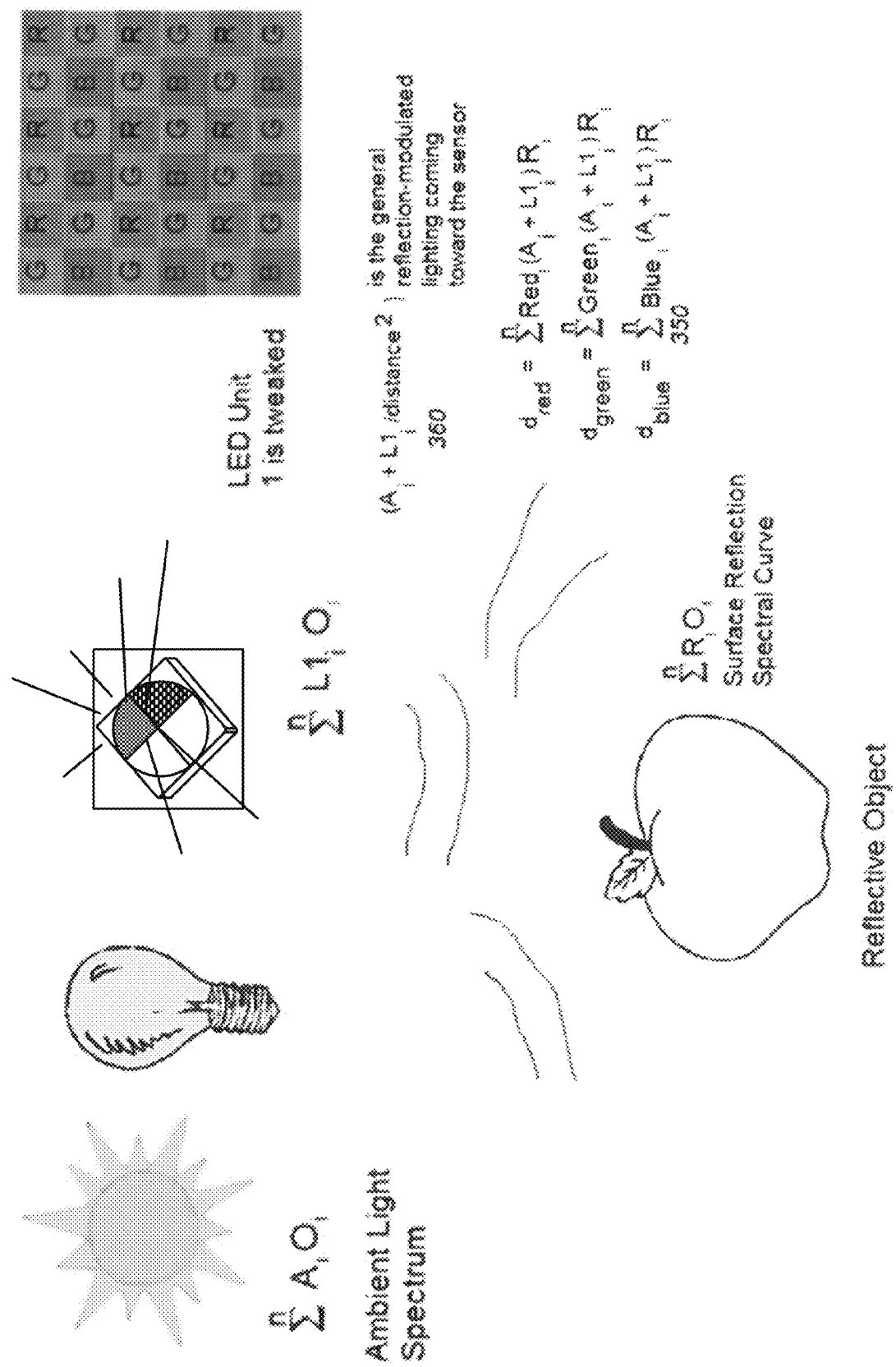

FIG. 36 is similar to FIG. 35, but here LED 1 is tweaked on and a distance-squared modified L1 term shows up in the collected samples from the Bayer sensor (distance-squared term not explicitly in equations).

FIG. 37 shows that individual LED tweaks can thus be isolated from ambient contributions. Here we see just one LED, number 1, and how we get three "g vector" measurement values that can roll up into matrix equations intending to solve the R coefficients (the unknowns). For surface "patches" involving thousands of pixels and allowing several LED tweak cycles, many otherwise noisy values can nevertheless produce superb patch spectral patch measurements.

DETAILED DESCRIPTION

FIG. 1 depicts how most modern cameras distinguish red apples from green apples.

An image of the upper-left-rearside 2012-era iPhone, 40, with camera aperture on the left, 50, and a small flash unit aperture on the right, 60, is shown, along with a simplified Bayer pattern representation of the camera's sensor, 70, depicted above the iPhone. With ten or fifteen minutes of discussion with Applicant's early grade school nieces and nephews, it does not take long to explain how the red apple, 20, lights up the little red-oriented sensors in the camera and the green apple, 30, tends to light up the green ones. [See FIG. 3, items 110 and 120 for explicit intuitive graphics for this only slightly oversimplified lesson].

The simplest point is that lighting does matter and any specific 'normal' camera sensor will have measurably different behavior in its digitized signal outputs as a function of the spectral characteristics of the light used to illuminate some otherwise 'fixed' scene. The related simple point better made right away rather than later is that, as always, 'range' or distance of an object from a flash source is a fundamental issue to this technology, just like it is with all flash photography. Virtually all commercial flash photography has a practical range of a few meters at best, maybe 5 or 10 for special types of photography. The same types of ranges will apply to this technology, generally considered, and this disclosure will attempt to at least touch upon how 'spectral fidelity' will often decrease as a function of range.

Concluding the initial discussion of FIG. 1 then, we find two common lighting sources for the apples, the sun, 10, and perhaps our smart phone flash unit 60, perhaps individually or perhaps in combination. Obviously there are many other forms of 'ambient' lighting beyond the sun as well, and likewise, digital cameras in general have taken the technology of 'the flash unit' to quite remarkable levels of sophistication and expense.

Figure 2:
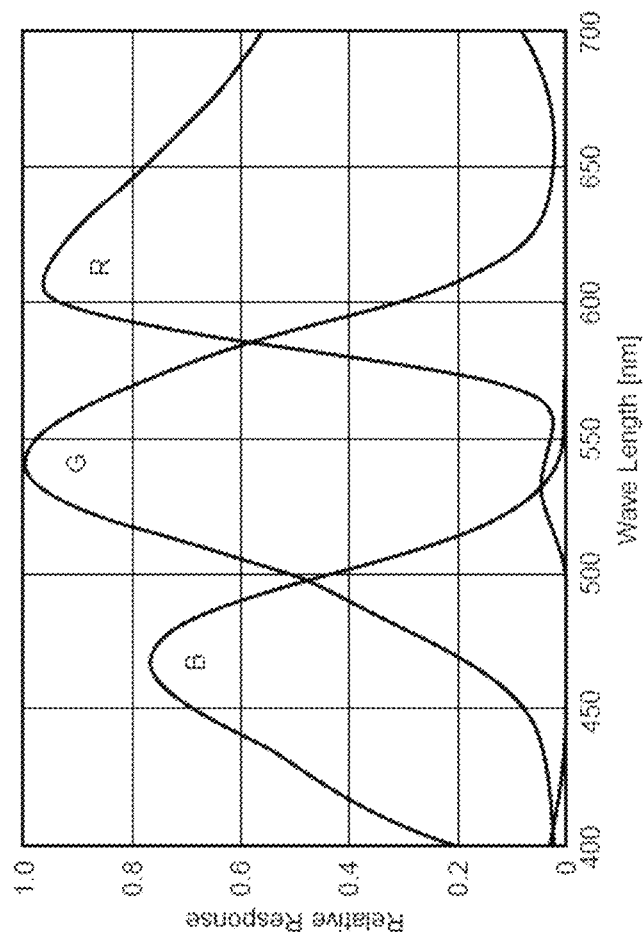
FIG. 2 presents a plot of three spectral detection profiles of an illustrative Bayer-pattern CMOS sensor.

FIG. 2 continues the 101-level summary of the technology by presenting a highly generic but also highly typical plot of the three spectral detection profiles, 80, of a Bayer-pattern CMOS sensor. The X-axis is the continuous rainbow blue (400 nanometer wavelength light) to red (700 nm). The Y-axis is labeled 'relative response' and for this summary can just mean how strongly light of a very specific wavelength can produce signals in a modern sensor (as manifested by digital values post A/D conversion). These curves are very familiar to designers of color cameras, sensor designers, etc. They are also generally familiar to more technically inclined photographers. Those familiar with such curves understand that there is great variability and subtlety in how and why these curves are the way they are, and manufacturers of cameras and sensors spend not inconsiderable time studying and re-designing how such curves manifest themselves. This technology adds new, potent variability into the fairly mature and 'stable' art of Bayer-pattern filtering in particular, as will be seen. Concluding the initial discussion of FIG. 2, however, it can be noted that by and large these filters have been and continue to be tuned in such a way that digital cameras can best 'match' or 'capture' natural colors as humans see such colors. Not surprisingly, these curves mimic what color scientists concisely refer to as the CIE color matching functions (and their many subtle variants).

FIG. 3 gets back to our red and green apples and a just-slightly oversimplified summary of how a camera can measure that a red apple is red and a green one green. We find a new green curve, pointed to by label 90, representing an idealized 'spectral reflectance' profile of a green apple, and likewise a red curve, pointed to by label 100, representing the same from a red apple. Color scientists understand that such curves never go to zero for any wavelengths and that the correspondence of the spectral shapes to the 'G' curve of a Bayer filter—and the 'R' curve—is pretty unlikely. But for this summary, that's just what these particular apples behave, how do you like them apples.

So, for intuition's sake, we can imagine close-ups of our Bayer-pattern sensor in a smart phone camera or a digital camera being 'lit up' in the green pixels, 110, when those pixels correspond to patches of the green apple, and likewise the red pixels 'light up,' 120, for patches of the sensor viewing the red apple. Imaging engineers, etc., all know this 'lighting up' is simply a nice correlation of innate spectral profile of an object with the spectral profile of a sensor, hence giving rise to much higher digital signal values in the pixel outputs. Indeed, this 'correlation' is generally accepted to be a multiplication of the quantified spectral light flux of a patch by the also-quantified spectral profile of the sensor. Said another way and described repeatedly in all books describing color science, this is an integral multiplication of two spectral curves, one weighted by light flux from an object, the other weighted by spectral quantum efficiency of a pixel, integrated from blue to red. The generally accepted result of such a multiplication are the well known digital number signal outputs from pixels, also taking into account commonly known issues of analog signal to digital count value factors as well. (all too much information for a summary, perhaps; after all . . . we're just showing that green apples tend to light up green-filtered pixels and red red!!).

FIG. 4 now introduces a highly idealized 'ambient' lighting source spectral curve, 130. The main point of this simple diagram is to highlight that all light sources will have a so-called spectral structure. Professional photographers learn this in diapers. A streetwise way to put it is: there ain't no such thing as white light.

The second point to FIG. 4 is that this generally unknown and generally ALWAYS DIFFERENT ambient white-ish illumination will produce slightly different output values to our R, G and B pixels of the Bayer (or other) types of filtered pixels. Again, this is all exceedingly well known to engineers and photographers, with the detailed point of FIG. 4 giving a first indication of how in this one example, the B pixels will be just a tad lower in their resultant digital values IF some object is lit with this particular type of illumination, RELATIVE TO, the G pixels. The effect in this displayed example might be on the order of 20% to 30% less signal showing up in the B pixels than might otherwise show up with purely 'white' signal or equal energy across the spectrum.

FIG. 5 continues the main line of summary from FIG. 4, now presenting an equally idealized but nevertheless instructive case of illumination here called 'slight green-ish mainly blue-ish,' 140, represented by a perfectly straight line from the upper left to the lower right of the coordinate background. The deepest point to this figure is that the spectral profile of light can be actively structured! (as every lighting engineer well knows). Depending on the type of lighting source, one's ability to structure illumination spectrally will often be highly constrained due to the raw physics of the light source one is using. For example, this perfect line from 400 nanometers full-on to 700 nanometers full-off is theoretically achievable (within, say, 5 to 10% in a 100% scale) using normal tungsten bulbs and some sequence of 5 or 10 well-chosen optical filters, but by and large it is not an easy matter to cudgel the spectrum of tungsten to do exactly what you want it to do, it has innate physics thank you very much and that's the palette we are given. Later sections will zoom in much more particularly on modern LEDs and the many choices of how to manipulate their 'raw physics' into, importantly, economical and practical spectral shapes.

But back to FIG. 5, we now find three new curves depicted labeled B,' 150, G,' 160 and R,' 170, representing the here-called 'lighting modified' effective spectral response functions of the Bayer pixels. The physics of the Bayer pixels will of course not change, but one can now 'know' how their actual response functions will behave IF one knows that a particular kind of spectral light will be illuminating an object/scene. The English-phrase way to put this might be: "OK Mr. Apple, I know that in purely white light my Bayer-pattern pixels will read out the signals and colors just like they ought to, but in this new light where I know the modification of the illumination profile, I also know that my raw pixel output signals will be more like the 'effective' profiles of 150, 160 and 170. So once again, FIG. 5 uses the common convention of putting a prime ' symbol on the three earlier curves B, G and R of FIG. 2."

FIG. 6 further continues this summary line by depicting our red apple, where if we don't tell our Bayer camera that we're using funky light to illuminate the apple, it will dutifully display the apple as yellow on a smart phone screen or some digital camera captured display! The yellow is mainly due to the notion that while the actual reflective spectrum of the apple has not changed from curve 100, FIG. 3, its 'coupling' or multiplicative integration with the new spectrally-shaped response curves G' and R' of FIG. 5 is now more even between the digital response of the G' channel and the R' channel. The R' channel goes down simply because the lighting has much less red in it. And the red apple spectral curve already had a little bit of coupling into the G channel in the first place (even though it is a 'red' apple), hence one might imagine that the resulting yellow will be a 'dark yellow' as a nit-picking matter. So, the point to FIG. 6, well known to virtually every professional photographer on the planet is: lighting makes a big difference to capturing 'true' color. FIG. 6 also foreshadows the important role of 'knowing' what the spectral characteristics of the illumination indeed are.

FIGS. 7 and 8 are probably as general a summary of certain aspects of the technology as one can muster. Plop a multiLED flash source in place of what in 2012 is either a single LED or a 'white' dual-LED, then synchronize its flashing to captured frames from the sensor, most often being a Bayer-sensor at least for smart phones.

As further disclosure and figures will elucidate, the individual properties (physics) of each LED within a singularly packaged multi-LED can be 'tuned' and/or optimized along a variety of design parameters, with 'cost' being the perennial Goliath parameter. The result, after processing to be discussed in detail, is that you've turned your smart phone or digital camera into a hyper-spectral imager. More importantly at a 'cultural' level, you've formed the groundwork for explicit 'true color' or what this disclosure call 'direct chromaticity capture' imaging. Arcane to many folks but not to color scientists, one now has the basis to have a normal Bayer/etc. camera directly produce 1931 chromaticity coordinate values, replete with highly testable error bars on those values. The physics of the LED choices, perhaps new choices on the details of the filter curves for the pixels themselves (see FIG. 2), all can combine for an analytic prescription for anticipated error bars on such pixel (or small patch of pixels) chromaticity output. One can immediately appreciate that once new sensors such as the announced Sony RGBW, and once LED spectral characteristics continue their inevitable advance, then direct chromaticity capture is simply a matter of engineering decreasing error bars on the values themselves, set against all the usual variables of distance from an object, glare, ambient light unknowns (to be discussed at length later), effective temperature of the flashing itself, motion, etc.

To the lay public, this technology will just be another chapter of 'weird stuff' that can happen when the flash is applied. Many camera and/or flash manufacturers have been playing games with flash for years and decades, so that's nothing new. 'Everybody knows' about pre-flashes, flashing flashes, etc. FIG. 8 just summarizes what is going on during a given 'flash session' if you will. Imagining that our CMOS sensor in the figure likes to expose and frame-out at 30 Hz, we get a glimpse of four sequential flashes, 200, 210, 220 and 230 of a current proto-example of a multi-LED, 190, FIG. 7. In this case, the four frames will be taken over a $2/15^{th}$'s of a second period. By 'proto-example,' above, it is meant that this particular 4-LED device manufactured by Edison corporation has not had the physics of it LED spectral emissions tuned or optimized for this particular technology, BUT, even with the innate spectral profiles of their current offerings (none is in figures because applicant has not located any), it is highly likely that even with this very specific 2012 model(s) of this device, many of the basic attributes of the technology should work.

FIG. 8 tries to generalize the 'four flash' scenario by using the '4*n+X' mathematics, where flash 200 gets X=0, 210 X=1, 220 X=2 and 230 X=3, thereby accommodating video sequences. A single photo, of course, can just be four flashes and be done. FIG. 8 also continues the somewhat idealized and generic summary line whereby the flash 'colors' are obviously different from each other as looked at by a human observer, but subsequent figures/disclosure will explore the spectral aspects of these flash sources. It should also be mentioned here that the smart phone itself (and iPhone in particular) is exemplified in the two figures, but the basic principles are quite applicable to traditional digital cameras, where the behind-the-scenes frame/flash synchronization will have slightly different physical realizations in digital cameras as opposed to smart phones. The latter are dripping with multi-functionality and wireless connectivity, and hence are tailor made for this technology. Digital cameras are more single-purpose typically and things such as frame/flash synchronization are already quite 'plumbed' as they say, but there will be more novelty involved in multi-frame synchronization surely.

Figure 9:
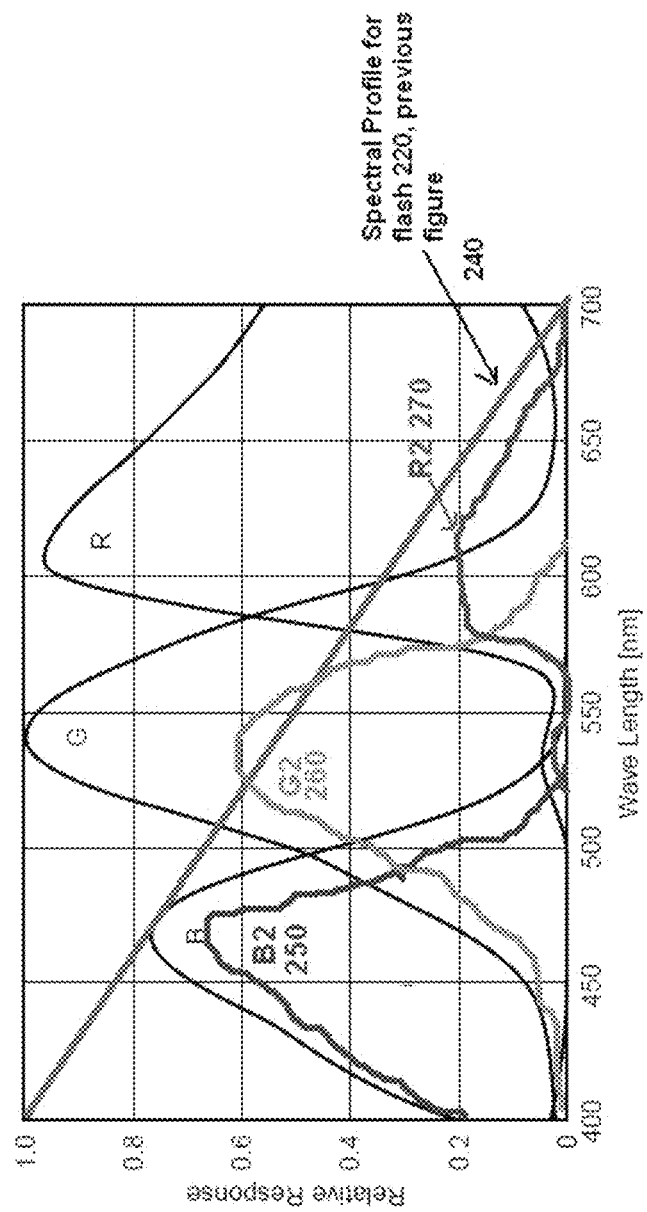
FIG. 9 is similar to FIG. 5 but incorporates insight from FIG. 8.

Continuing the summary line, FIG. 9 now blatantly copies FIG. 5 but re-enumerates some of the items to fit the example of FIG. 8. We can now fruitfully pretend that the particular purplish flash 220 of FIG. 8, derived from the left quadrant LED cell of multi-LED chip 190, FIG. 7, happens to spit out light with the spectral profile 240, our old friend the idealized straight line from FIG. 5. As later discussion will elucidate, both the physics of LEDs AND the desires of optimizing LEDs for this technology will probably dictate different results than these, BUT, this straight line still can nicely serve explaining how the technology works no matter what spectral profile one winds up with.

So FIG. 9 also presents another important but subtle change over FIG. 5, that is that we have now labeled the resultant effective spectral response profiles as B2, 250, G2, 260 and R2, 270. Why? These new numbers attached to B, G, and R represent the X=2 of FIG. 8, identifying which LED these curves correspond to.

Figure 10:
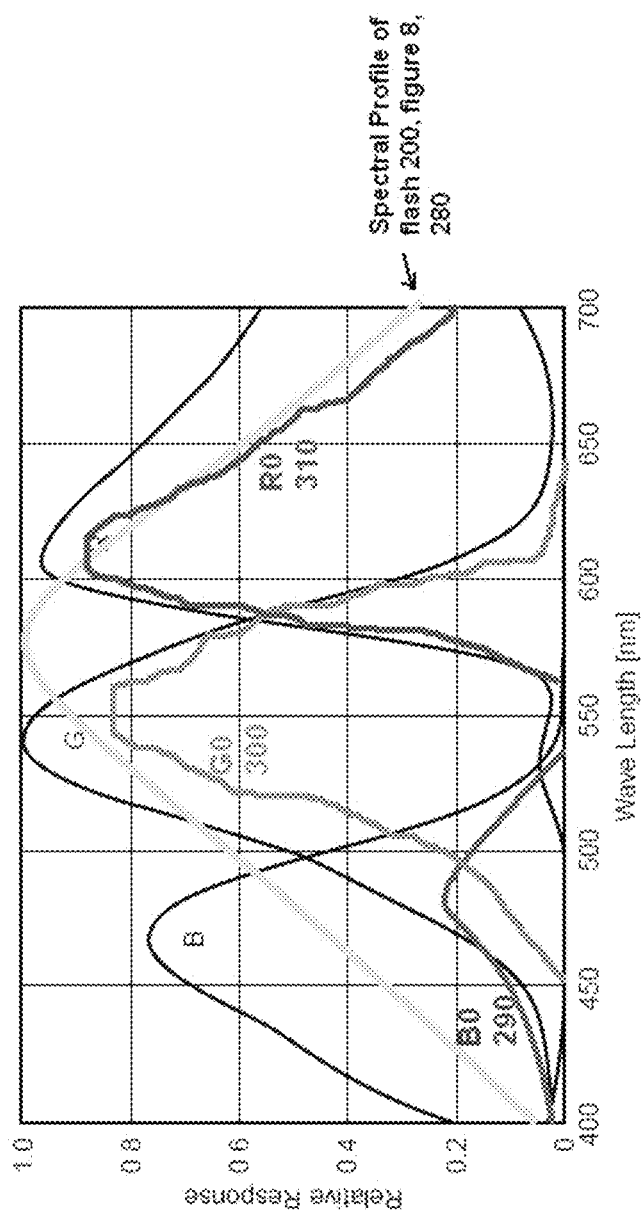
FIG. 10 shows another family of spectral curves.

FIG. 10 reiterates this basic point, now imagining that flash LED 200 might have a profile that looks like the curve 280 in the figure. We then can see the resultant B0 curve, 290, the G0 curve 300 and the R0 curve 310. FIGS. 9 and 10 suffice to make these matters clear, such that one can appreciate that flash units 210 and 230 of FIG. 8 both have their unique effective B1, G1, R1 and B3, G3, R3 respectively. All told, we have 12 unique effective response curves, bounding at least for this example the number of 'bands' we can measure at 12.

FIG. 11 competes with FIGS. 7 and 8 as being a general summary of certain aspects of the technology, only this time from the plumbing-side of the universe. One can imagine that we are in a pretty dark room taking a picture of this red apple, maybe 1 meter away from the apple. Our four flashes take $2/15^{th}$'s of a second to occur, the CMOS sensor grabs and stores four Bayer-frames of data. If we then zoom on one specific 'Bayer-cell' of green-red-blue-green, which happens to be 'focused' onto a tiny patch of the red apple 320 in the figure, we now can see the conceptual-yet-palpable explosion of that singular Bayer cell into a pseudo-3D array of 12 digital values (16 if we count the G's twice, but later we shall see that these are averaged in the simplest implementations). [Later, we will quite explicitly take away the condition 'in a dark room' and discuss the multifaceted and fascinating world of bringing normal ambient light back into the scenarios]. Rounding out the technical description of FIG. 11, then, we find the labels 330A, 330B, 330C and 330D applied to the 4 (or 4*n for video) frames captured under the four different LED lighting conditions. The figure attempts to be highly explicit that it is the same Bayer cell each time, just different in time and lighting.

FIG. 12 inherently asks the question: now what? So you get these 12 independent or 16 dependent numbers, what next?

FIG. 12 for fun fills in some hypothetical and quite realistic digital numbers into the 16 splayed "Bayer-cell sub-cells" as one might say. The question is explicitly asked in the figure labeled 350: how does this array of 16 8-bit values somehow translate into an estimate for the innate reflective spectral profile, 340, of the apple patch 320?? The depicted curve 340 is explicitly different from the red apple's curve, 100, FIG. 3, precisely to illustrate that we don't yet know what it is and we must find some way to estimate it given only the 16 digital values.

A very, very brief side trip into the limitless world of functional estimation cannot be avoided in this summary line, largely depicted in FIG. 13. This is a laughingly tippy-tip summary of how one can 'parameterize and discretize' otherwise continuous functions, knowing that there are trade-offs in the process. The benefit of the process is as simple as it comes: you can estimate functions using a countable set of numbers. The trick then just becomes turning one set of numbers, our acquired 16 digital values of FIG. 12, into a new set of numbers which multiply some chosen set of these so-called bases-functions, hopefully producing a function which gets as close as possible to the 'unknown curve' 340, upper right of FIG. 13. The reason applicant felt it was imperative to take this side trip into an area that many mathematicians take for granted is that some of the most profound engineering challenges of practicing this technology will be contained in the subtleties of choosing proper bases functions and specifically in matching innate physics of LEDs and pixel-filtering to such bases functions as the 1931 CIE curves. Applicant has not yet performed, yet full expects to during broader implementations of this technology, very detailed looks at the performance benefits versus implementation cost trade-offs between, for example, using discrete versus continuous bases functions as but one example. The figure shows examples of both accordingly, dusting off an old favorite named Chebyshev Polynomials, a mathematical gem with an appropriately obscure and evocative name.

FIG. 14, however, evokes the old phrase measure it with a micrometer, mark it with a chalk and chop it with an axe! But this axe is not all that coarse and indeed, it may for many applications wind up being a highly useful and practical approach to basic hyper-spectral imaging and the vast world image processing that entails.

FIG. 14 depicts a 'custom' set of 5 basis functions intended to be a first cut at what might nicely work for both the physics/psychology of human vision as well as the physical practicalities of CMOS/CCD sensor response profiles, LED spectra, etc. It is an explicit compromise between a purely hyper-spectral system that might posit 5 equal 60 nanometer bands from 400 to 700, and one which takes into account that Bayer-profiles already bias raw information content of sensor data into the 'photopic' region of the spectrum, i.e., the region tuned to human vision. So why not let's tune our 'simplest' bases functions (aka 'bands') to this region as well. We will later discuss the very important bases-function choice of the smooth CIE curves. FIG. 14 thus continues the important summary line of the technology, emphasizing how the basics work and leaving important variants for their own sections.

FIG. 14 presents the newly minted bands V, W, X, Y and Z, how original! V just happens to be violet-ish, Y yellow-ish, but there is no intent here to sanctify these bands nor tread on the many existing bands of color science and astronomy. The intuitive rationales to these functions, certainly subject to empirical tuning once real Bayer-sensors and real LEDs are in the picture, include: a) symmetry; b) a nice spread around the 1931 CIE chromaticity diagram; c) a coarse 'coupling balancing' between the typical R, G and B curves of a Bayer sensor; and d) a very nice 80/50/40 ratio of the bandwidths, which introduces the next FIG. 15.

FIG. 15 adjusts these bases functions to become so-called orthonormal, a fancy way of just saying the areas under their curves are equal (and equal to '1' if you really want to nit-pick the y-axis scaling). So what is the deal with these five box functions? The deal is that we are going to try to estimate object spectral profiles (over each and every Bayer-call of four pixels) using these boxes as our curve-fitters, that's the deal. FIGS. 16 and 17 will take us through the mechanics.

Starting first with FIG. 17, at the highest level we are just going to create a very classic 'linear transformation' between our 16-valued acquired vector and our newly minted VWXYZ vector. Give me a 16-valued 1-D array of numbers, I'll give you back a 5 valued array, try that with dollars and people, a profit of 11 numbers each transaction, not bad. The traditional form of this transformation, especially when you have a situation where functions behave nice and linear just like spectral profile multiplication does, is the matrix equation form, depicted as g=Hf.

We will return to FIG. 17 but let's look first to the very elemental operation required to even talk about a 'transformation.' What exactly is being transformed? FIG. 16 tries to answer this simple question: Any given response function (of our 12, with G0 singled out, 300, in the figure) will 'linearly couple' or 'transform' or 'light up' or 'choose your English word' into our chosen bases group, here using FIG. 15's VWXYZ. This is just what it looks like, an area based integration of the multiplication of one curve by the other, sequenced across all five VWXYZ bands. To make this a bit more tangible, label 410 is by 5 new entities below the graphic, given the names G0V, G0W, G0X, G0Y and G0Z. These are the so-called coupling coefficients between our chosen bases functions and this particular effective response curve. Some crude estimate numbers are thrown in there both for fun as well as roughly showing that they correspond to the areas whereby G0 spreads its energy into the various buckets, the numbers being typical integrations.

FIG. 17 illustrates our matrix formulation now partially filled out with bona fide numbers. We see twelve numbers in the g vector (420), down from 16 because we chose to average our pseudo-dependent G values in each Bayer-cell. This is the acquired data and it will change each image to the next. We then can see a shrunken version of FIG. 16, here in FIG. 17 now explicitly calculating but one of our 12 rows of the H matrix, 430. It is implied that this operation will be done on all twelve rows, using each of the unique individual response functions run through the FIG. 16 washing machine.

Then we find the f vector, 440, now populated with V, W, X, Y and Z subscripted by a 'p,' 450, because we will be performing this transformation of 12 numbers into 5 numbers for every Bayer cell associated with all 'patches' that make up a full image.

The good news is that this highly explicit matrix equation is not required in the implementation of this technology, there are very well known ways to create inverse matrices which just vector process 12-valued vectors into 5-valued vectors. The steps required in creating these inverse matrices can be as involved as the whole functional estimation world of FIG. 13, replete with 'regularization' of poorly ranked matrices and the like, but these topics are not for summaries. The even better news is that the summary section of this disclosure now concludes and the remainder of this disclosure will discuss various nuances and alternatives to realizing this technology, with the 800-pound Gorilla being the use of CIE bases functions instead of hyper-spectral-ish bases functions.

Optimization

Figure 18:
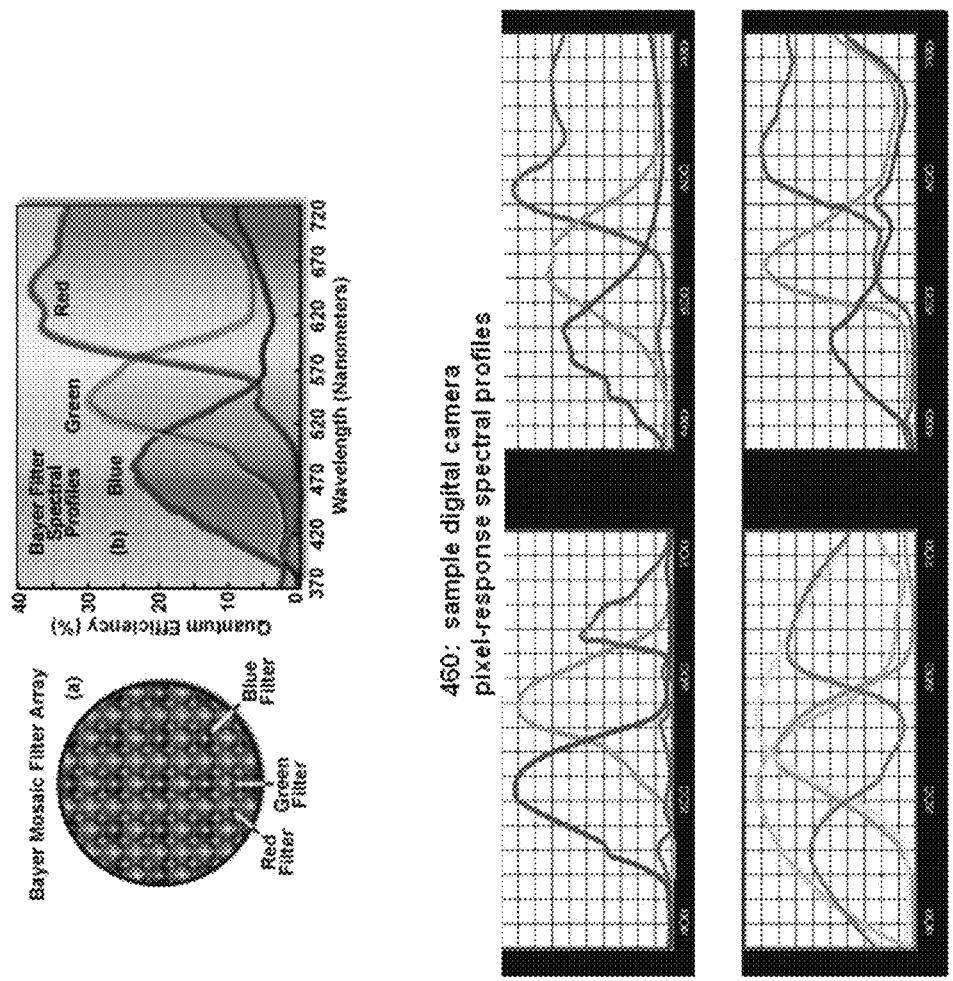
FIG. 18 introduces some of the considerations from a sensor side of the system.
Figure 19:
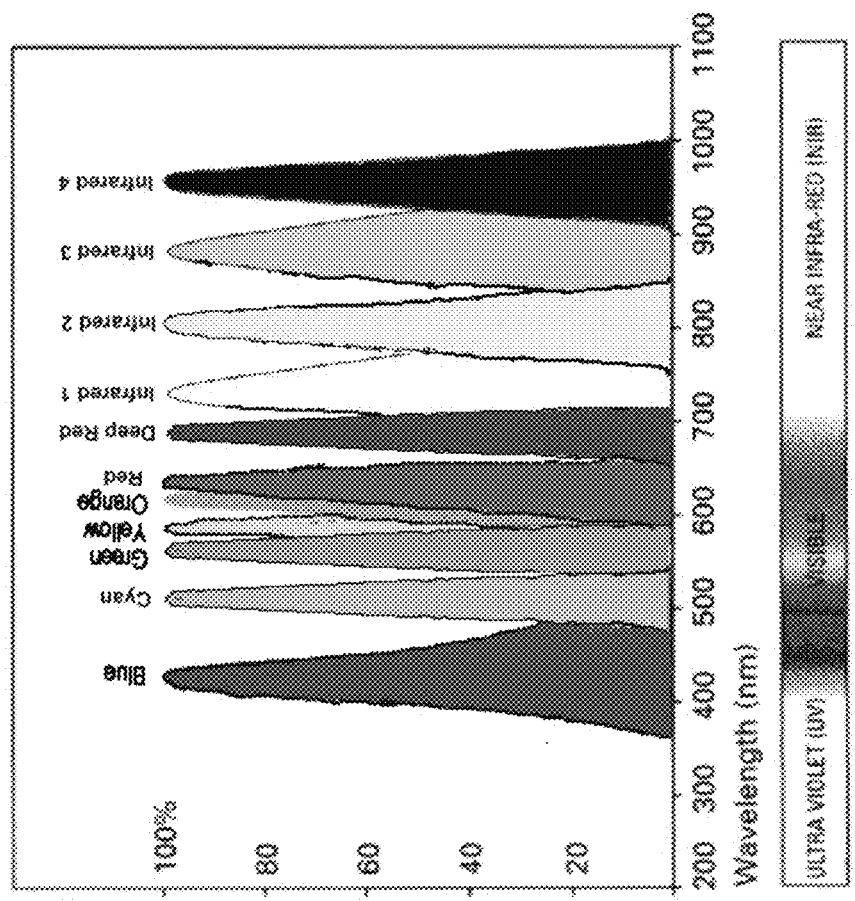
FIGS. 19-22 delve into considerations concerning the illumination LEDs.

FIG. 18 conveys in a single picture that there is all manner of flexibility on the sensor-side of this technology in terms of innate pixel spectral sensitivity profiles. Ever since Bryce Bayer of Kodak develop the single-chip color solution, no end of refinement went into finding better and more cost effective solutions ultimately determining the productized forms of the spectral curves. Also depicted in FIG. 18 are digital camera spectral curves, 460. One even has four different spectral curves, all the better, where adding a fourth inherent sensor band merely increases the effective 'independent' number of response profiles. Sony's rather new 'RGBW' sensor lay-out, previously mentioned, is simply heading in directions that this technology can exploit.

Figure 20:
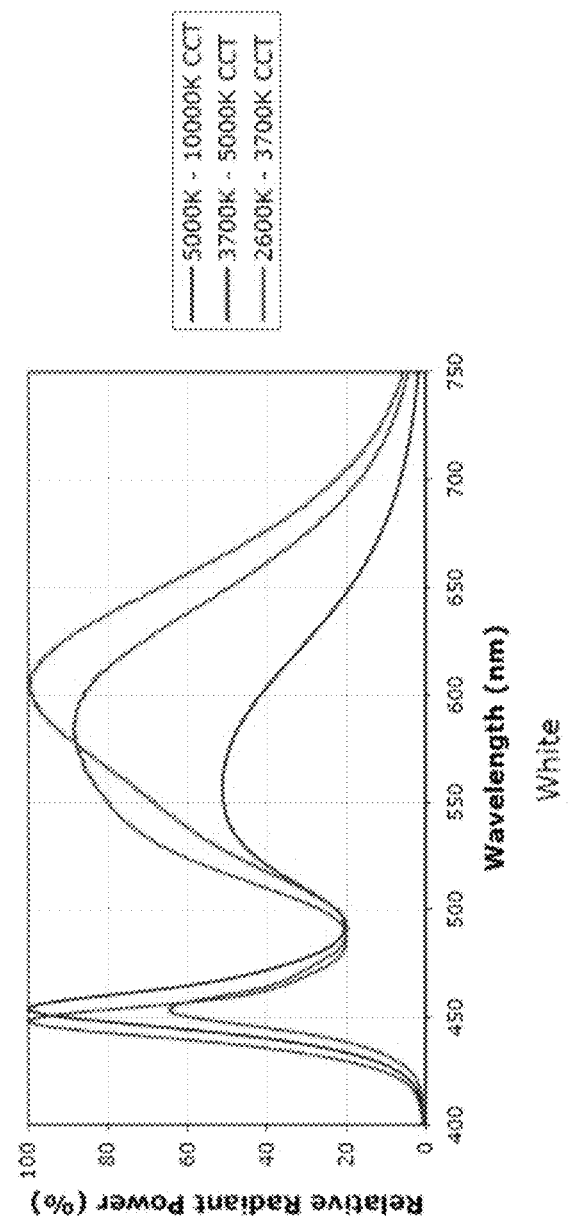
Figure 21:
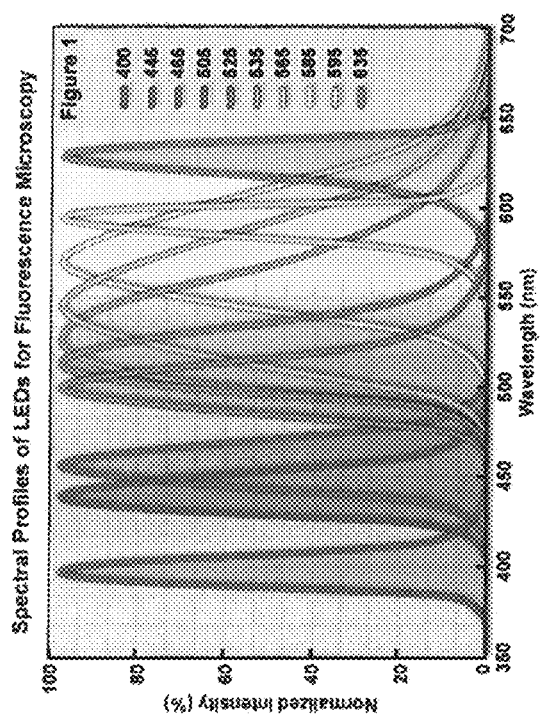

FIGS. 19-22 all collectively attempt to convey the very rich 'design space' represented on the LED-side of this technology. Depicted throughout these figures are various copied diagrams from not only different manufacturers but different industries as well, with FIG. 21 explicitly lifted from a fluorescence microscopy work. FIG. 21 provides another example of the ability to design spectral shapes aimed at certain applications, and in particular provides an example from Fluorescence Microscopy. FIG. 21 demonstrates even more flexibility on the LED spectral-shape side. FIG. 20 displays a fairly typical spectrum of a 'white' LED, where this is actually a family of curves showing that slightly different spectra can be achieved based on a variety of design-scope decisions made on materials, drive electronics and even physical temperature if applicable. It is fully anticipated by applicant that this technology will add another log to the fire well burning already in the LED industry, a fire which is always pushing for new spectral properties all within generic economic constraints.

FIG. 22 also serves the purpose of a more formal introduction of the heretofore much-touched-upon 1931 CIE chromaticity diagram. A full introduction to this rich diagram and its 7 decades of development is radically beyond the scope of this disclosure, and we shall be content here to simply say that it remains a bedrock of color science.

Figure 23:
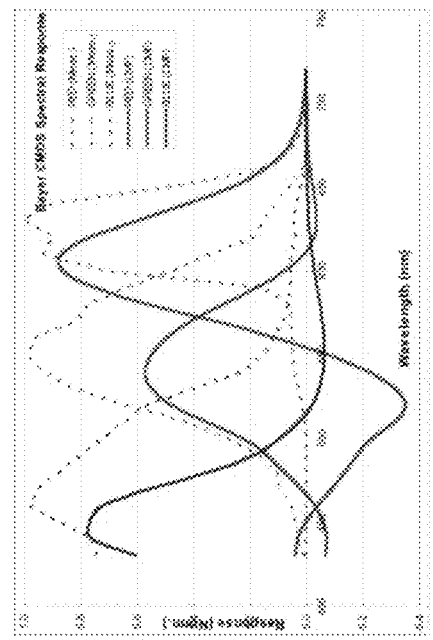
FIG. 23 illustrates a relationship between Bayer filters and orthogonal color matching functions.

This disclosure will discuss primarily using the raw x, y and z 1931 color matching functions (FIG. 24) but the reader should understand that there are many transformed variants of these functions, including orthogonalized versions depicted in FIG. 23. All of the subtle variations have their rationales and areas of strength, so by choosing the classic 1931 functions this disclosure once again has explication trump the black hole of optimization and perfection, an activity best left to commercial and proprietary efforts that drive one competitor to have a winningly-distinguished product over another.

FIG. 23 serves as a form of historic reference on how the design of Bayer-filters for pixels has been related to orthogonal color matching functions. The intuitive trick for Bayer-sensor designers of the past has been to 'generally match up' the filter-based responses (which includes silicon sensitivity functions) to the classic human vision color matching functions. With a rough fit thus obtained, a designer could then perform highly sophisticated modeling and testing of how well a given color camera would perform relative to its ability to 'nail' chromaticity coordinates of objects, AS a function of the innate spectrum of those objects and the lighting conditions—comparing and plotting generally error ovals similar in visual kind (but not substance) to the ovals in FIG. 22. In short and perhaps a bit too oversimplified, once a designer finds that physics-based witches' brew of filter goop, they were pretty much stuck with the chromaticity-error behavior of the devices. One small objection to Bayer-pattern CMOS over the years, relative to the wider flexibility inherent in 3-chip color cameras for example, has been this limitation to goop characteristics irreverently described. Word on the street in 2012 is that more and more manufacturers have gotten the goop significantly better where innate capabilities of the goop matches the functions better and better. In any event, the aspects of this technology dictate that getting the goop close to some of these curves is all well and fine (helpful, yes), but when combining this with sequential structured-spectral LED lighting, one now has a whole new dimension to tune in to analytic chromaticity matching. The upshot of this is that a sensor-LED combination of design principles can lead toward an unequivocal engineering pathway toward precision chromaticity recording, replete with all-possible-object-spectrum variation plots within the CIE chromaticity diagram itself. In other words, one can model 'all possible reflection-spectrum' objects that have a specific chromaticity, then directly see how those objects will be measured—chromaticity-wise—by a camera with Multi-LED flash as per this technology. Error-bars, or error ovals, will still be in full play but adding the LED physics to the party brings in the steroids.

FIG. 24 then explicitly introduces the classic 1931 x, y and z curves taught to color scientists in their very first lectures as students. A deliberately generic LED-sensor combo profile is included, labeled 470. Whatever set of pixel profiles and whatever set of LED profiles produce whatever larger set of combined profiles, they all multiply by these three classic curves giving rise to what the figure calls a 'weight' in the matrix, 480, but a dozen different scientists and mathematicians will give it two dozen different terms. The bottom line is that it is a single numeric value placed into the H matrix, with this particular CIE matrix having only 3 columns corresponding to the three classic curves. To the right, then, is the unknown f vector being solved for, labeled 490. Same deal as before then: any given 'patch' corresponding to a Bayer cell, and RGBW cell (maybe even a 9 by 9 cell with 81 different filters!) will give rise to this inherent matrix, inverse matrices (vector processing coefficients) will be generated, then out will pop direct CIE color matching coefficients which then . . . voila . . . skipping the mathematical step of turning Xp, Yp and Zp into a 'chromaticity coordinate' . . . turns into an X, 500, on FIG. 25.

FIG. 25 also wants to compete with FIG. 11, which itself wants to compete with FIGS. 7 and 8, as being a high level summary of aspects of the technology. But FIG. 25 won't win because the 1931 CIE diagram is pretty arcane and contained to the color science community and its immediate brethren, AND, hyper-spectral imaging in general goes well beyond matters dealing with only human vision. So, we can grant FIG. 25 a claim to summarizing one of the most intriguing consequences of the technology at least.

FIG. 26 also must play the role that other figures already have played of being a pointer to rich and varied proprietary activity as opposed to any kind of grand description or summary of such. The subject is how one deals with ambient light in both a rigorous as well as a practical way. The answer is gazillions.

The figure unabashedly presents a humble text list of five particular 'things' designers and engineers can do, with a not-possible-to-be-more-explicit suggestion to use common ingenuity and best engineering practices to develop specific approaches and distinguish your offerings accordingly. This is not a 'punt' of this whole topic, it is an act of humility whilst facing design and implementation issues that hundreds and thousands of very gifted people in the past have grappled with, and inevitably as many more will do so in the future. This is where the allusions of religious fervor were previously invoked.

So, the list in FIG. 26 starts with a very simple approach which certainly should do for most 'normal consumer' photography, but surely even more sophisticated things will be done even in this application. To wit: design in a little button (or some buried user-choice menu item) a simple switch that has a little sun, a light bulb, and maybe a moon or something). Better yet, don't even make the user do anything, just figure things out from the captured image data itself using many known image processing techniques. But, the core approach is to estimate the ambient lighting characteristics, especially its general brightness level relative to the flash brightnesses, and just add this estimate to the H matrix row values outright. This exercise is left to the reader and is well known to those practiced in image processing where 'ambient effects' need to be dealt with one way or another.

Item 2 in FIG. 26 presumes a pretty bright LED source and envisions its pulsing on a fairly short period along with an equally short exposure time for the pixels. This inherently will bring down the ambient levels of light simply by reducing the active exposure time OF that ambient light. For example, 1 millisecond exposures every $\frac{1}{30}^{th}$ of a second will clearly have 33 times less ambient light content than 33 millisecond exposures!

Item 3 can be done in combo with other. It is the notion that if you can't beat 'em join em.' By all means take an image with just ambient light! Simple. You can even use this as an estimator for item 1. You can also then use it in your matrix equations if you have sufficient confidence in the ambient light's general spectral profile. If the application is 'decent color photographs,' a little bit of error is not always a bad thing, go ask anyone who plays with color in Photoshop.

Item 4 is a kind of cheat but very possible as well. There are so many photography gizmos out there, use 'em. Light meters and auto-light gauges and sunshine sensors (GPS coordinates even) . . . all of these can provide useful information to any form of data correction, compensation, etc.

Finally, item 5 is a bit of an odd one but quite workable for the very serious photographer (or hyper-spectral imaging practitioner). One might not know the relatively stable background 'lumens' value of the ambient light, maybe it is say 50 lumens for some given patch of the apple, but one CAN flash that patch with 30 lumens of this flash, then 40, then 50, then 60, knowing that you are pumping in 10 lumen increments, then differences on your sensor data should correspond to the 'known differences' that you are pumping onto the scene. Patches of objects should also respond linearly to these increments as well as absolutes in brightness, so hey, for you precision measurement types out there that want and/or need pretty analytic approaches to fine-scale spectral measurements with as much of ambient background removed as possible, this might be your ticket.

Sample Applications

It might turn out that the main application of this technology will be dominated by simply being applied to the many decades of advance in color imaging, who knows. But this section and a few diagrams tree-top discuss some other applications.

FIG. 27 illustrates two of the starker and clear potential medical applications of this technology. In both of these cases and many other medical situations where 'color cameras' are used as a core part of the practicing of some given medical art—hello—hyper-spectral analysis of pixels will virtually always trump simple human visual color scrutiny in terms of raw diagnosis capabilities. Is there hyper-spectral tuned diagnostic database out there in the world? No, not much yet to applicants' knowledge, but boy there ought to be. Normal versus abnormal biological clusters in the colon, esophagus and stomach will all naturally create more of a 'signature' in 4 bands or five bands or more, than they will in human-visual-system tuned RGB. Clearly, Doctors will rely heavily on human color perception as well, but that is not the point—fine, keep doing normal color viewing/analysis, but bring a whole new view to the situation. Doctors have long proven that any new tool of diagnosis will be eventually welcomed and put into practice especially if the costs keep coming down. FIG. 27 also has dental imaging there for grins. Applicant would be afraid to use this technology on his own mouth for fear that I want to go seek professional cleaning far more often than he currently does!

FIG. 28 then attempts to do a modicum of justice to an otherwise bewildering array of potential applications both on the purely 5+band hyper-spectral imaging side as well as the 'true color imaging' side. The beyond obvious application is simple food/produce quick quality control, both vendor-side and consumer-side. Vendors may freak out thinking that all their customers might some day be inspecting making their fruit purchases with their smart phones rather than the squeeze of some grimy fingers, but hang on, maybe that's a good thing? And surely the cat and mouse game of true quality versus presented quality would find new chapters of sophistication . . . but the point remains, this technology has the potential to play here. Likewise inspections, counterfeit 'suspicions' if not outright 'proof,' all possible. The figure is embarrassingly high level in its attempt to summarize the applications, with surely ten years hence answering the question better.

FIG. 29 then alludes to a slightly more niche world surrounding identity, printed graphics, packaging, etc. Digital watermarking and 'fingerprinting' are both well-known methods for identifying objects for a range of applications, and the printing industry has always found various interesting technical gimmicks to spruce up its fare (such as color-based stereo printing where colored glasses can reveal 3-D forms, as but one simple example). It is beyond the scope of this technology to explain why this technology can improve upon these existing arts, but in summary, it can greatly increase effective signal strength in 'chroma' oriented digital watermarking applications, and the additional information channels and fidelity thereof can greatly increase signature-characteristics for fingerprinting applications. And gimmick wise, no question, direct graphics can be printed into CMYK objects which can't be seen by normal human vision but sure enough, with a little bit of multi-band distinguishing, come out clear as day in a hyper-spectral image.

Figure 30:
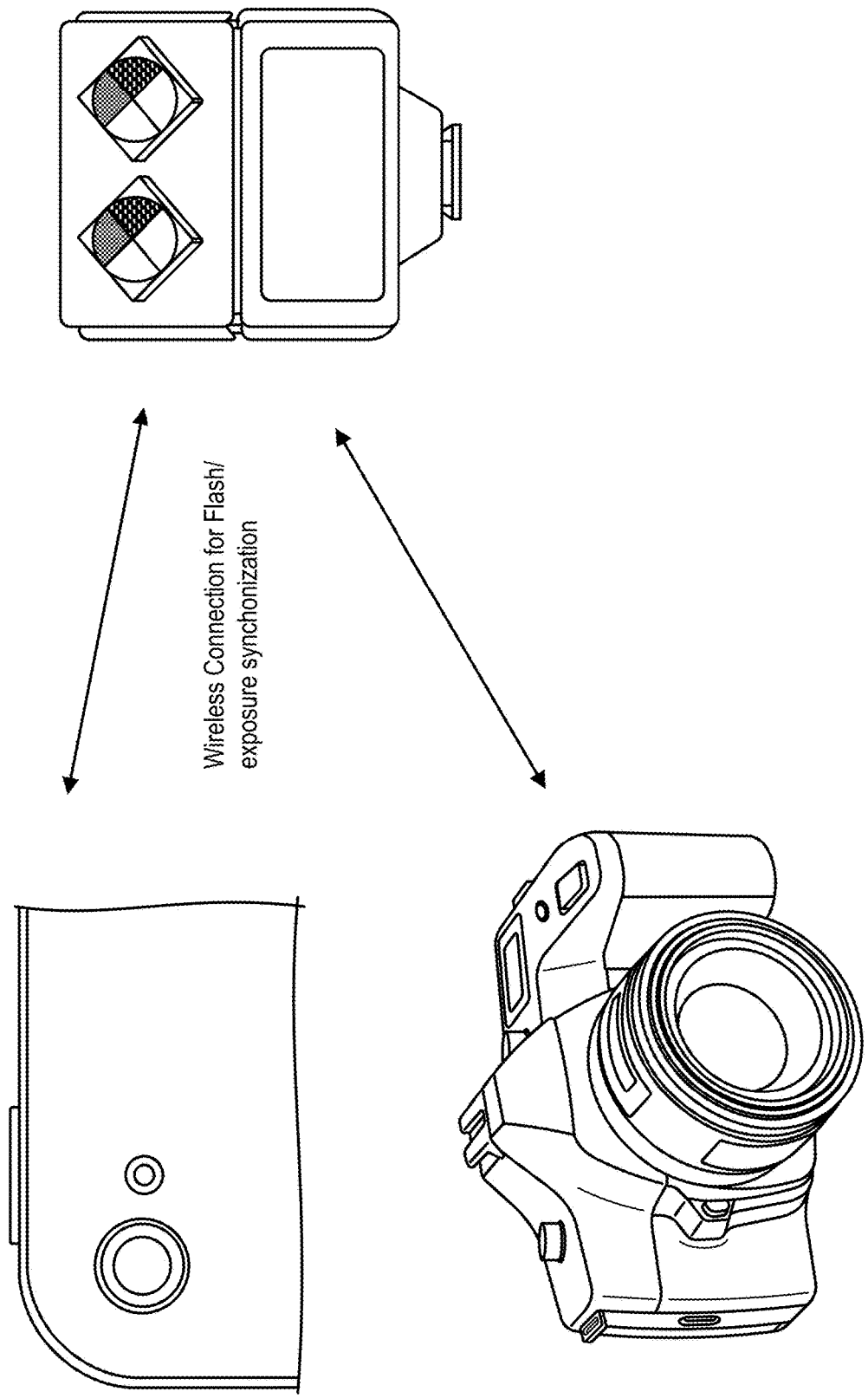
FIG. 30 details how conventional form-factor flash units can employ the present technology.

FIG. 30 just presents the quick note that any and all 'traditional flash units' of any kind could potentially be 'upgraded' to the principles of the technology. The need for frame/flash synchronization can be solved in a variety of ways, including 'post hoc' filtering in cases where there is no wired or wireless way to do direct synchronization. Bottom line: there is a bunch of legacy equipment out there that with a little cleverness can be morphed in this technology's direction.

FIG. 31 makes the point that integrating a properly tuned multi-LED into the actual LED aperture/slot of a smart phone may be practically a few years out, and there are highly viable and faster ways to market with this technology. The depicted smart phone has a not-entirely uncommon 'clip-on' unit, in this case some extra helper-optics, but there is zero reason why this can't be a flash unit instead (or in addition to).

Figure 31A:
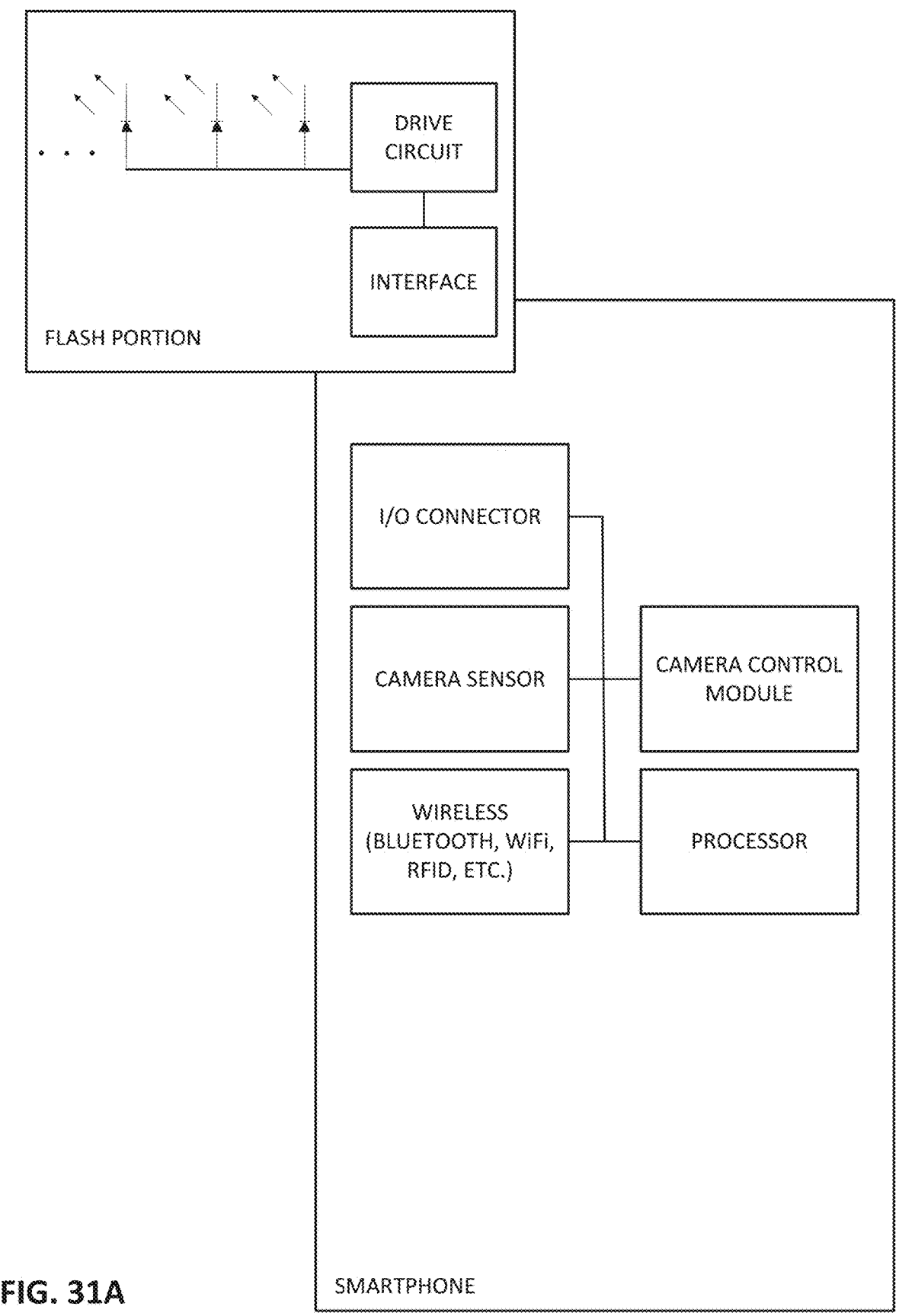

FIG. 31A is a block diagram showing selected components of a smartphone and of such a clip-on accessory. In the phone, a camera control module sends signals to which the camera sensor responds. Among these signals is a frame timing control signal, which triggers the sensor to capture a frame of image data, e.g., in a video sequence. The accessory includes an interface portion that receives a version of this frame timing signal from the camera. Based on this information concerning the timing of frame capture, a drive circuit in the accessory controls illumination of selected LEDs in a programmed, synchronized manner.

In one particular implementation, the clip-on accessory plugs into an I/O connector on the phone. For example, the multi-pin connector at the bottom of the Apple iPhone device may be used, or the signal jack through which audio signals are transferred between the device and peripherals can be used. In the latter case, the flash accessory may be programmed in accordance with audio signals provided to the accessory under control of the smartphone processor. The flash unit can interpret the frequencies and timings of these audio signals as specifying flashes of different LEDs, of different intensities, and of different durations, in successive video frame capture intervals.

In another arrangement, the interface receives the frame timing signal by a wireless connection, such as RFID or Bluetooth or WiFi. In yet another arrangement, a signal is conveyed from the smartphone to the flash accessory by a wired connection.

Power for the flash unit may be provided from the smartphone (e.g., via a wired connection), or the unit may have its own battery power source.

While the flash accessory in the depicted arrangements is adapted to physically engage a portion of the smartphone, so as to removably attach to the smartphone, in other embodiments the flash components can be integrated into the smartphone.

FIG. 32 quickly treats the important practical issue of motion. Motion of both the camera relative to a scene, but also motion in terms of video. This disclosure has touched upon video mainly as a 'flashing' and frame reconstruction issue, this figure looks more at the raw motion of the camera frame relative to some external scene. The somewhat mature technology of 'motion compensation' is explicitly called out in the figure, where many companies and camera suppliers have already solved basic problems of what many call 'motion blur.' (This problem is also addressed in applicant's application 61/759,996, and counterpart non-provisional application Ser. No. 13/842,282 (now U.S. Pat. No. 9,136,300), entitled Next Generation Imaging Methods and Systems, which are hereby incorporated by reference.) Point number one here is: use them. The figure keys more in on the ideas that different frame exposures correspond to different spectral flashes as a general matter. So, there are then ways to tap into standard motion estimation of the frame relative to a scene, these same approaches can be applied to the luminance element of all frames—their general structure of brightness variations, to then ultimately re-associate the pixel patches from one flash image to another flash image. Image X may need to shift a couple pixels up and over to some master reference frame, and image Y may need to do the opposite. These operations are fairly well known in image processing, mainly dealing with image registration and also 'orthographic alignment,' with the end result always being improved resilience to performance degradation due to motion. This area also fits well into the proprietary methods bucket, where practitioners of the technology are highly encouraged to invent improved image registration methods.

Light Tweaking

Figure 33:
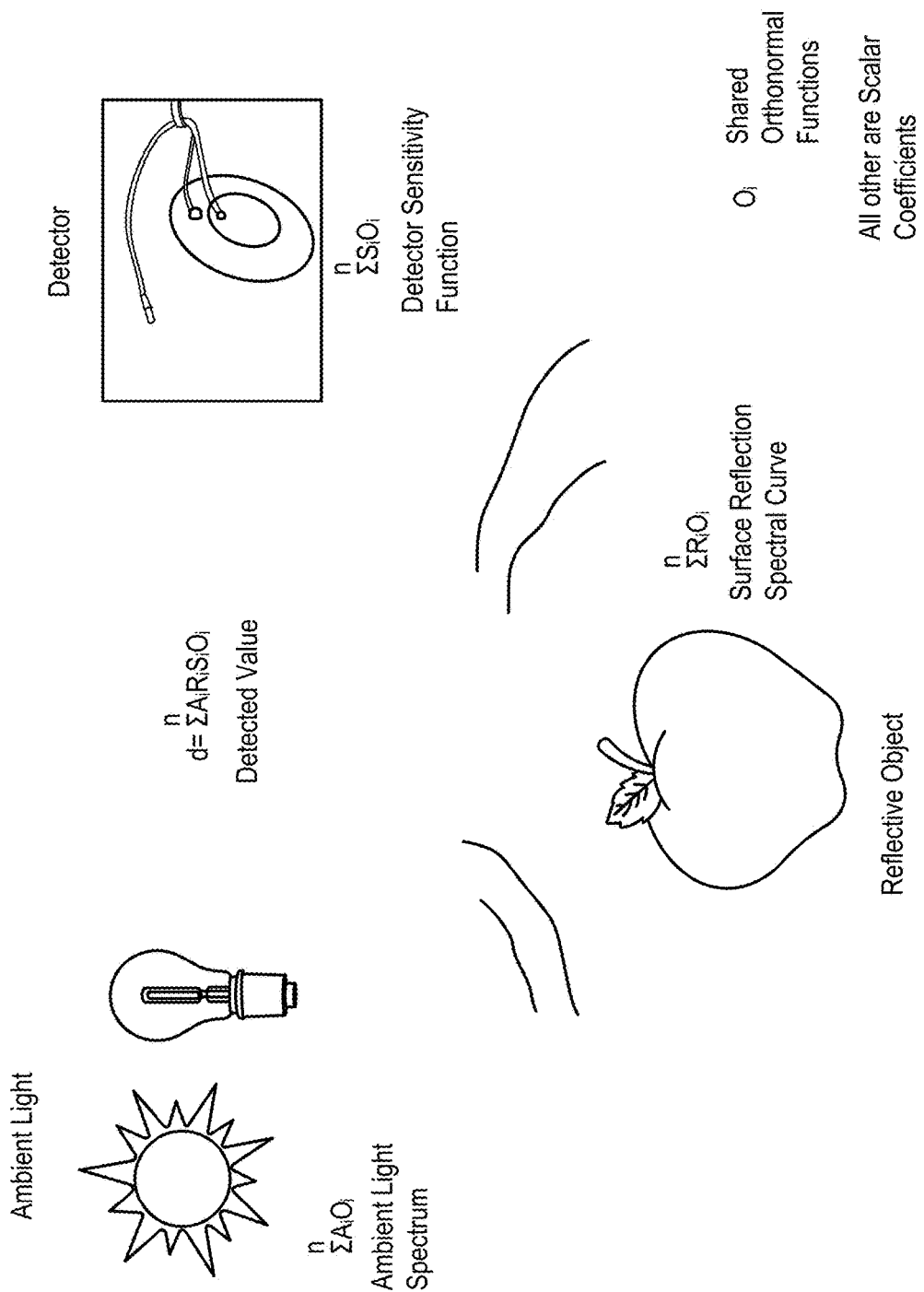
FIGS. 33-36 further elaborate considerations involving ambient lighting.

FIG. 33 attempts to describe from a more mathematical angle how arbitrary ambient lighting can be dealt with and mitigated in terms of its effects on the measurement of surface spectral characteristics and/or surface color. The mathematical treatment then culminates in a more detailed 'routine' that can be applied to the issue of ambient-lighting correction. This routine will be referred to as light tweaking.

In FIG. 33 we find light sources (representing 'ambient' light) with some arbitrary spectral profile represented as a set of coefficients multiplying some orthonormal set of bases functions defined from 400 nm to 700 nm. We see this light source uniformly lighting some flat and uniform surface with a reflectance spectral profile with its own set of coefficients using the same orthonormal bases functions. Then we see a single photodetector measuring the reflected light from the surface, where the spectral response of the detector has yet a third set of coefficients describing its properties, again using the same bases functions. Those practiced in illumination and light detection arts can appreciate the generalizations in the extreme represented in this figure. This is very deliberate so that light tweaking can be clearly defined and seen instantly by artisans to be viable.

Figure 34:
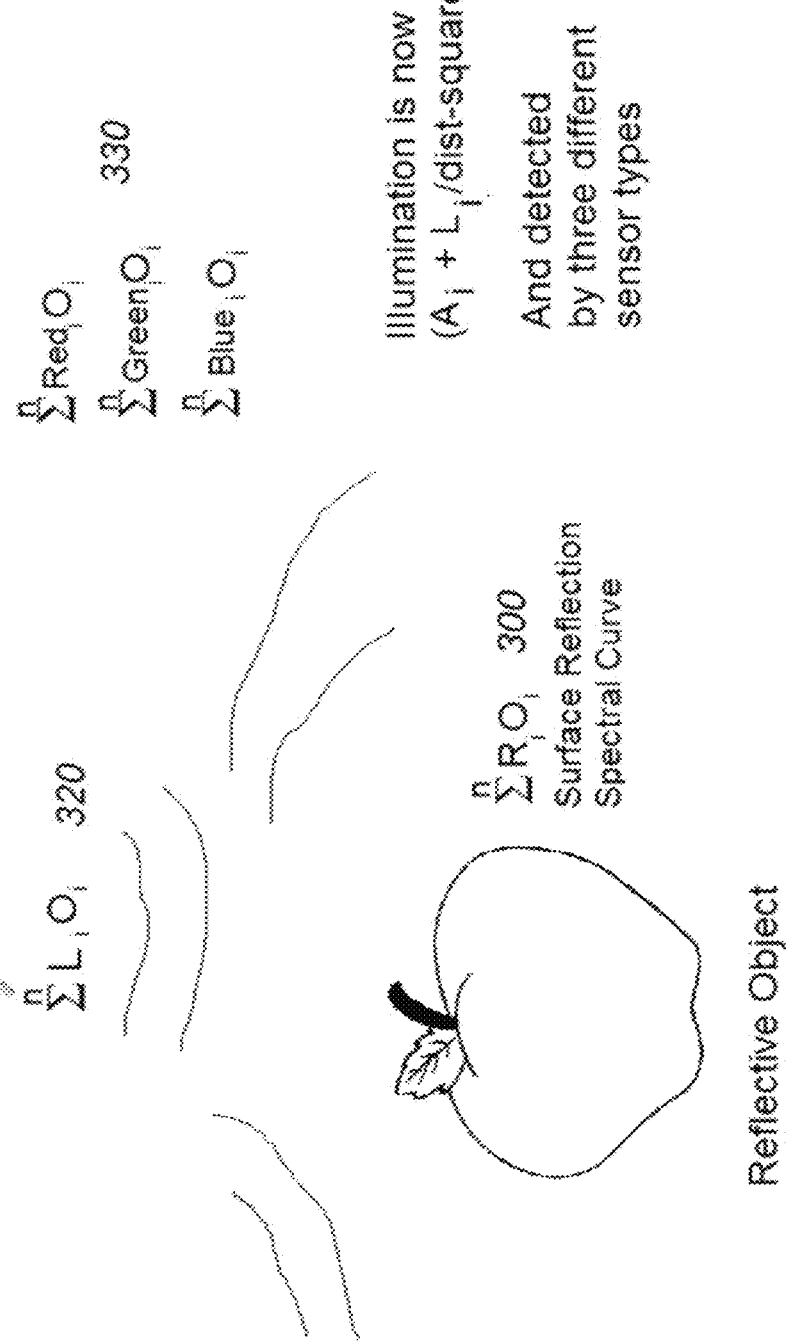

FIG. 34 now introduces a fourth set of spectral coefficients belonging to an LED (or equivalent) second light source also uniformly lighting the surface. Depicted with this new LED source is the need to be more specific about distance between a source and an object than with 'ambient.' For the purposes of measuring 'relative spectral reflectance' of surfaces, all spectral components of the LED lighting will experience the same distance-squared diminution, and hence distance is merely a formal factor which requires noting for a full mathematical treatment but which can easily be dealt with in the measurement solution process. We also see three detectors now instead of one, where all three have differing spectral sensitivity functions and in this particular embodiment, they take on the spectral profiles typical of Bayer-pattern imaging detectors or R, G and B. The task to be defined and then solved is to determine the unknown surface spectral coefficients, 300, given the unknown ambient coefficients 310, and the known spectral coefficients 320 and 330. More particularly, the task will be to make this measurement even when the light energy from the LED source is dwarfed by the ambient light energy, perhaps up to where the ambient light is fully ten times brighter than the LED light reaching the surface, and perhaps even brighter. Ultimate brightness ratios and measurement signal to noise properties reduce to classic empirical testing, where additional disclosure will show that once thousands and millions of Bayer pixels are sampling surfaces multiple times per second, superb surface spectral measurements become possible. The same 'routine' certainly applies to non-Bayer spectral sensitivity pixels and non-LED known light source illuminators and much more complicated ambient lighting conditions than that depicted in FIG. 33.

FIG. 35 now expands the number of LED light sources to 4, from just the 1 in FIG. 34. Not unsurprisingly each LED has its own spectral radiance profile characterized by coefficients 340. For this point in the disclosure's description of the 'routine,' FIG. 35 can represent the state where all LED elements are turned off and hence all L1, L2, L3 and L4 individual spectral coefficients are zero. The next few paragraphs and figures then describe the 'tweaking' by this four element LED unit, in contrast to this completely off state of FIG. 35.

FIG. 36 now introduces an individual tweak of light tweaking. LED 1 is turned full on during a sampling exposure of the 3 R, G and B pixels. The sampling duration (exposure time) is identical to that of FIG. 35. FIG. 36 shows that there are now new measured values from the three pixels, 350. For explanatory purposes, these values are only slightly higher than those of FIG. 35 so that we can immediately illustrate that the LED lighting can be much weaker than ambient lighting and yet as we will see, good surface spectral measurements can nonetheless be made. Label 360 indicates this by putting the explicit distance fall-off term into the figure, where we can imagine that the LED contribution might be 10% or even less than the ambient contribution.

The light tweaking routine then posits that a 5 frame period cycling of pulsing the individual LED sources, including a single 'all off' state, can illuminate the surface. This cycling would be designed to be in perfect synchrony to the frame rate of a conventional Bayer-pattern imaging device (or any monochrome of multi-spectral imaging device as well). Each frame would isolate some given state of supplemental (to ambient) LED illumination, including no supplemental illumination at all. The ensuing mathematical formalism of this cycling can also be depicted in FIG. 36 if we substitute the appropriate L coefficients into the equations 350, including zeros for the all-off state of the 5 cycles.

FIG. 37 explicitly shows how the unknown ambient lighting spectral coefficients can quite easily be removed from the aggregate mathematical equations. In practice, everyone knows cameras move and surfaces move, but by cycling the 'no illumination' state along with the LED tweaked states, a constant sampling of pure-ambient values can take place and interpolated into the time periods where the tweaked states are occurring.

Straightforward simultaneous linear equations fall out isolating the unknown surface coefficients in a classic 'f' vector, modulated as they are by the 'known' tweak values of the LED coefficients and R, G and B, represented by the classic H matrix, then finally the measured del-R, del-G and del-B values themselves become the classic 'g' vector, all rolled up as a g=Hf standard linear algebraic equation. f=inverse H times g is the equally classic solution to this equation, with over a century of prior art methods applicable to properly forming, filtering and shaping such solutions generally with the goal of optimizing signal to noise ratios on the measurement of surface reflectance coefficients. [Note that an additional 'unknown' is present—the precise ratio of overall ambient light to the LED light; solutions can be formed with this additional unknown, or, there are methods such as depth-sensing which can aid in independently measuring this unknown for applications where this might benefit the overall measurement fidelity; the g=Hf formulation implicitly contains this distance factor and it is only in highly mobile situations where this additional distance nuance needs to be worried about as an error component on measurements due to motion].

This section's discussion up through FIG. 37 posits a very simple lighting situation, a simple surface, uniform lighting and only three detectors whereas modern imaging devices usually have millions of such RGB detectors. Be this as it may, these simple principles are quite extensible to small patches of imaging sensors viewing small pseudo-uniform patches of objects and their surfaces. Ambient lighting conditions can vary quite a bit on 'normal' objects and scenes, especially with regards to surface normal (perpendicular directions from the surface) relative to where a camera is placed. Applications will range from extremes where surfaces change their characteristics on a 'per pixel region' basis, all the way to broad uniformly lit surfaces giving rise to near-identical measurement conditions across millions of pixels (think placing a camera up close to a flat color of some graphic printed paper or package). It is thus entirely expected that these principles described in FIGS. 33-37 will adapt accordingly. Where certain levels of 'region uniformity' are discovered, thousands and millions of R, G and B measurements per second can be classically averaged together prior to submittal to the g=Hf solution formalism, culminating into excellent surface spectral measurements even when the LED lighting is 10× fainter, or even fainter, than ambient lighting.

Counterfeit 'Suspection'

Using the present technology, ink and other manufactured surfaces will be found to have distinctive 'spectral signatures' that can be used to separate originally printed, authentic articles from counterfeited articles. The non-English word 'Suspection' is used in the title, though those practiced in the art of counterfeit analysis may substitute 'detection' as well. There is a subtle yet slightly arcane reason suspection is used rather than detection: purists understand that unequivocal 'detection' of counterfeits is an asymptotic goal and never (in practice) an achievable absolute. A milder form of a technical goal is then to strongly suspect something to be counterfeit and then to either believe that suspicion if its integrity is sufficiently high, or, to subject some suspected counterfeit article to further testing for authenticity.

A counterfeit suspection device can consist of a clip-on unit similar to FIG. 31. A local or internet library of spectral signatures for various articles is stored, and when some given article is 'scanned' by the device and a spectral signature thus generated, a comparison with stored signatures is made, with some threshold set separating 'apparently authentic' versus 'suspected as counterfeit.

Specific choices of LED illumination spectral ranges can also be tuned and selected to help discriminate between originals and counterfeits. For example, a specific ink might be chosen which might have very strong reflective properties around 610 nanometers, and then one of the LED choices for illumination may similarly have strong illumination at 610 nanometers. The strong signal picked up from this concurrence of spectra would assist in separating originals from counterfeits in the ensuing spectral measurement processes.

Multiple phases of illumination and analysis can be conducted—each yielding further evidence tending to indicate that a suspect item is or is not a counterfeit.

Spectricity Vectors

Figure 38:
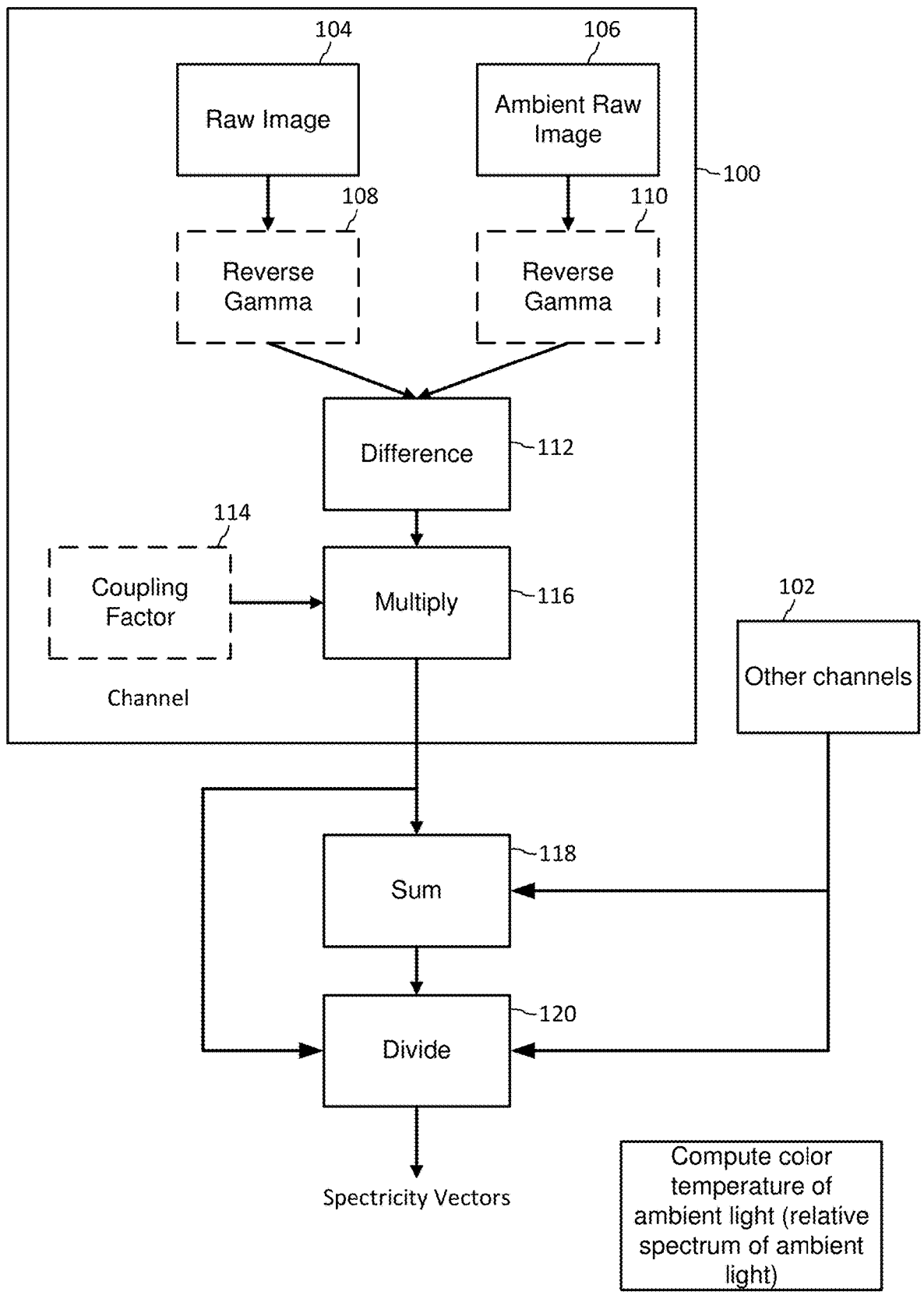
FIG. 38 is a diagram illustrating a process of generating spectral images in response to pulsing a target object with illumination in the presence of ambient light.

FIG. 38 is a diagram illustrating a process of generating spectral images in response to pulsing a target object with illumination in the presence of ambient light. The objective of this embodiment is to generate a form of spectral image data, which we refer to as an N dimensional "spectricity" vector. This vector has N-dimensions of spectral components per spatial location coordinate. For example, for an image comprising a 2 dimensional spatial array of pixels, each pixel location has N-dimensions of spectral components, which we sometimes refer to as channels. This technology also applies to image sensors that provide 3 dimensional arrays of pixel values (horizontal, vertical and depth dimensions).

The coordinate space of an N-D spectricity vector may also correspond to other domains such as a spatial frequency domain or other transform domain. Later, we discuss applications that transform (and inverse transform) spectricity images to different domains to derive spectral feature vectors used in classifiers, object discrimination, and object identification applications, including such applications based on supervised and un-supervised machine learning methodologies. These types of transformations further generalize the concept of a coordinate space of the N-D spectral vector.

Further, some applications employ video capture, which adds a temporal component to the spectricity vector. This temporal component enables applications to leverage the variation of a spectral image over time. Just as spectral images may be analyzed in a spatial frequency domain, likewise, spectral video vectors may be analyzed in a temporal frequency domain and other transform domains that include a temporal component.

The term, "spectricity," is loosely derived from the concept of chromaticity, as it represents ratios of a spectral component to a total. Whereas chromaticity is expressed as two ratios, spectricity extends the number of ratios to N channels, where N is greater than the typical 2 color space values used to express chromaticity in the field of color science.

As described in the methods above, we configure an RGB sensor based digital camera to capture images during exposure periods that coincide with illumination periods of different light sources (in this case, specifically 5 different LED colors in the visible light range). FIG. 38 illustrates the processing of captured images in terms of spectral channels, 100, 102. The processing for one of the channels is detailed in block 100, and this processing is the same for additional channels, as generally reflected by block 102. In this embodiment employing an RGB sensor (in particular, a sensor with a Bayer filter), each raw image is captured from a Bayer sensor and provided in the form of digital values (8 bit per spectral component per pixel). The raw image has three channels corresponding to the R, G, and B components of the sensor. The light from an LED light source, as well as the ambient light, couples at least in part into the R, G, and B components of the sensor.

Figure 39:
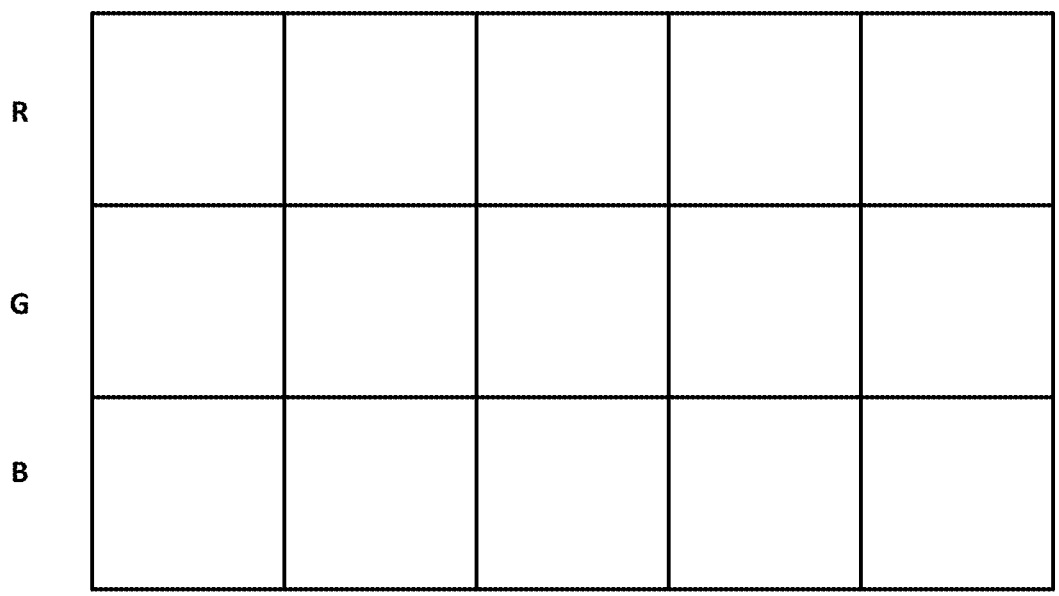
FIG. 39 depicts a matrix with the color channels of the sensor, R, G and B, on the vertical axis, and the LED light source colors on the horizontal axis, B, G, R, A, Y.
Figure 41:
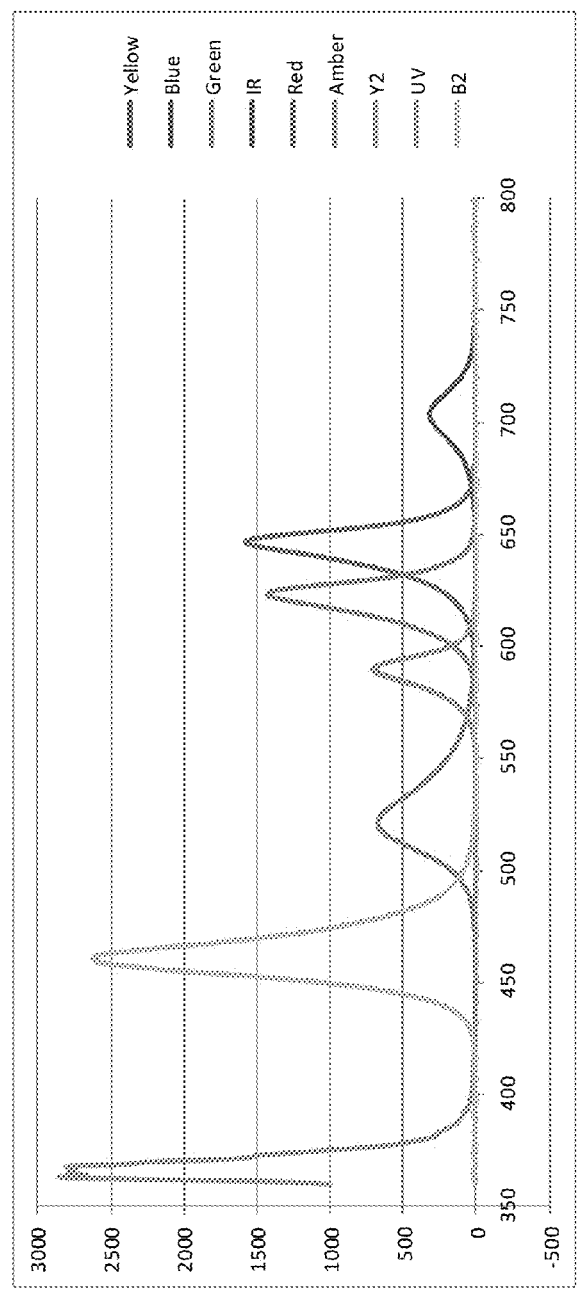
FIGS. 41-42 illustrate spectra measurements of LEDs used in various of our experiments.
Figure 42:

To help illustrate this point, FIG. 39 depicts a matrix with the color channels of the sensor, R, G and B, on the vertical axis, and the LED light source colors on the horizontal axis, B, G, R, A, Y (Blue, Green Red, Amber, and Yellow). In the simplest case of one LED illuminated at a time, the light from that LED is sensed, at least in part, within the three components of the sensor. For this embodiment, we used LEDs available from Marktech Optoelectronics of Latham, N.Y. ("Marktech"). FIGS. 41-42 illustrate spectra measurements of LEDs from Marktech used in various of our experiments.

In a typical camera device, the image undergoes filtering as well as other possible distortions and corrections (such as gamma correction, white balance automatic gain control, etc.). For five LED light sources individually pulsed, there are 15 channels provided by the sensor output, depicted as the cells of the matrix of FIG. 39.

Returning to FIG. 38, the input for each channel is a raw image 104 (captured with LED tweak) and a raw ambient image 106 (captured with no LED tweak). Each of these inputs optionally undergoes a process of reversing image transforms incurred in the image capture process and image post processing, such as gamma correction as shown in blocks 108 and 110. FIG. 38 illustrates the "reverse gamma," which refers to reversing the gamma correction, as one example of possible reverse transforms applied to undo transforms applied by the camera device or post processing that occurs prior to application of this method. The box is depicted in dashed lines, as it is optional depending on whether gamma transform has been applied prior to this point.

After this phase of reversing processing applied by the camera device, the adjusted ambient image is subtracted from the adjusted, LED tweaked image in block 112 to produce a difference image. In our experiments, we operate the light sources so that they are about 20% of the ambient light level, as measured in lumens. Looked at another way, we seek to have the modulation of light due to LED light sources tweaking the ambient light by about 20-30 Digital Numbers (DN) on a scale of 0-255 DN, which corresponds to 8 bits per color component per pixel. The ambient light level should be at or below a level such that the light added from each LED tweak changes the pixel values by about 20-30 DN without saturation. This tweaking of the light around a target object modulates the light reflected from the target. The amount of modulation needed to produce usable spectral images depends on the dynamic range of the sensor and ambient light level. Though subtraction is depicted here in FIG. 38, for applications where the ambient light is at or near zero, it is not necessary to capture and subtract the ambient light because it has negligible impact on the modulation of light from the LEDs.

For example, the sampling instant can be chosen to correspond to a null in the ambient light luminance—assuming it is predominantly artificial lighting—thereby minimizing the need to counteract ambient light. See, our related U.S. Pat. No. 8,385,971, which is hereby incorporated by reference. In U.S. Pat. No. 8,385,971, there is a passage on ambient lighting, and particularly on exploiting nulls in ambient lighting.

The resulting image (with or without differencing as the case may be) is then multiplied by a corresponding coupling factor. The coupling factor is a factor corresponding to the channel from the coupling matrix (see above discussion about deriving a coupling matrix generally and below for another example of its derivation). As noted below, a coupling factor need not be applied in all applications.

The same processing is applied to other color channels, as generally depicted by block 102. The N channels of spectral components of the resulting vectors are summed for corresponding spatial/temporal coordinates in block 118 and then the spectral component value at each coordinate is divided by the corresponding sum in block 120 to produce a normalized spectricity vector at each coordinate. Each of the channels comprises an array of spectral values, each value corresponding to a spectricity ratio measurement for a particular location coordinate, which corresponds to a point or region in space (and/or time for time varying data capture). To increase signal to noise ratio, for example, neighboring spatial and/or temporal samples may be combined in a filtering operation.

In the example of FIG. 39, there are 15 channels making the dimension of the spectral component of a spectricity vector 15 (5 different light tweaks×3 color components of the RGB Bayer sensor). As a practical matter, there is not usable coupling of the light source in each channel, and thus, the practical, usable spectral dimension of the spectricity vector is less than 15 (e.g., in some of our experiments, our processes generate spectricity vectors with 8 spectral component dimensions per location coordinate). Of course, as light sources are increased and applied in various combinations, it is possible to create more distinct spectral bands of light tweaks that are then coupled into the filter of the image sensor.

For the above embodiment, the coupling factors are derived by capturing raw images for each of the light source tweaks reflected from a white test sheet. The resulting images provide a measure of the coupling of each light source tweak into the filter corresponding to each color component of the sensor. From this measurement, a coupling factor is derived. While this coupling factor is not required in all applications, it is useful for applications to calibrate data from different light source—sensor pairs. The calibration process is: determine coupling matrix for light source—sensor pair, and apply coupling matrix for that pair to produce spectral images, and repeat this process for different light source sensor pairs used to collect spectral images. For applications where calibration of different devices is not an issue, the spectricity vector can be used without applying a coupling vector. However, even in such applications, it is useful to be able to ascertain the coupling so that it can be taken into account in subsequent use of the spectral content, to remove un-desired bias that the coupling may introduce in the spectral images.

Figure 40:
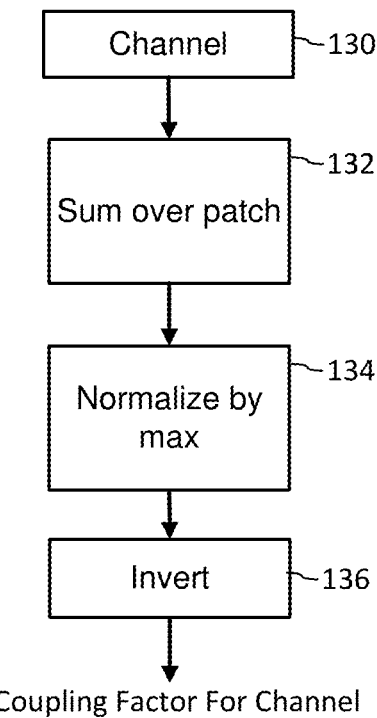
FIG. 40 illustrates a method for determining coupling factors for a pair of light sources and image sensor.

FIG. 40 illustrates a method for determining coupling factors. Taking the matrix of FIG. 39 as an example of spectral channels, we illustrate the process as follows. Each cell in the matrix of FIG. 39 corresponds to a channel in which the light emitted by an LED during an illumination period and reflected from a test patch is captured through one of the color components of the camera sensor. One can think of the channel 130 depicted in the process of FIG. 40 as the output of block 112 of FIG. 39, with similar options and variations as discussed above (e.g., reversal of transforms, differencing to subtract ambient, etc.). For each of these channels (130), the process of computing the coupling factors sums the pixel values over the patch area 132. Next, the process normalizes the coupling values by dividing by the maximum sum that is determined as the maximum from the sums of patches measured for all of the channels 143. The coupling factors are computed by inverting the coupling values 136. This provides a factor for each channel that is applied by multiplying it with a corresponding pixel values for that channel (e.g., as shown in blocks 114 and 116 of FIG. 38).

As illustrated further in code listing examples filed with this application, calculation of the coupling factors for a coupling matrix may also entail a process of removing measurements that fall below a threshold, as a form of filtering out un-wanted contribution from noise sources.

Cross Reference to MatLab Code Examples

As noted above, this application includes a computer program listing appendix including the following Matlab computer program files: Spectricityv11_multiday_set2-code_appendix.txt, SpectraImg-code appendix.txt and spectraId-code appendix.txt, configParser-code appendix.txt, all incorporated into this specification. The file, Spectricityv11_multiday_set2-code appendix.txt, includes Matlab code listing instructions for computing spectricity vectors, called spectricity images, and for colorimetric mapping (see below). The files named, SpectraImg-code appendix.txt and spectraId-code appendix.txt, configParser-code appendix.txt, are related as follows: SpectraId-code appendix includes a main Matlab script, configParser-code appendix is used to run this main script, and SpectraImg-code appendix includes instructions for computing colorimetric mapping (referred to as true color, see CalcTrueColor function), for computing a coupling matrix and spectricity vectors, etc.

Colorimetric and Other Mappings Derived from Spectral Images

Figure 43:
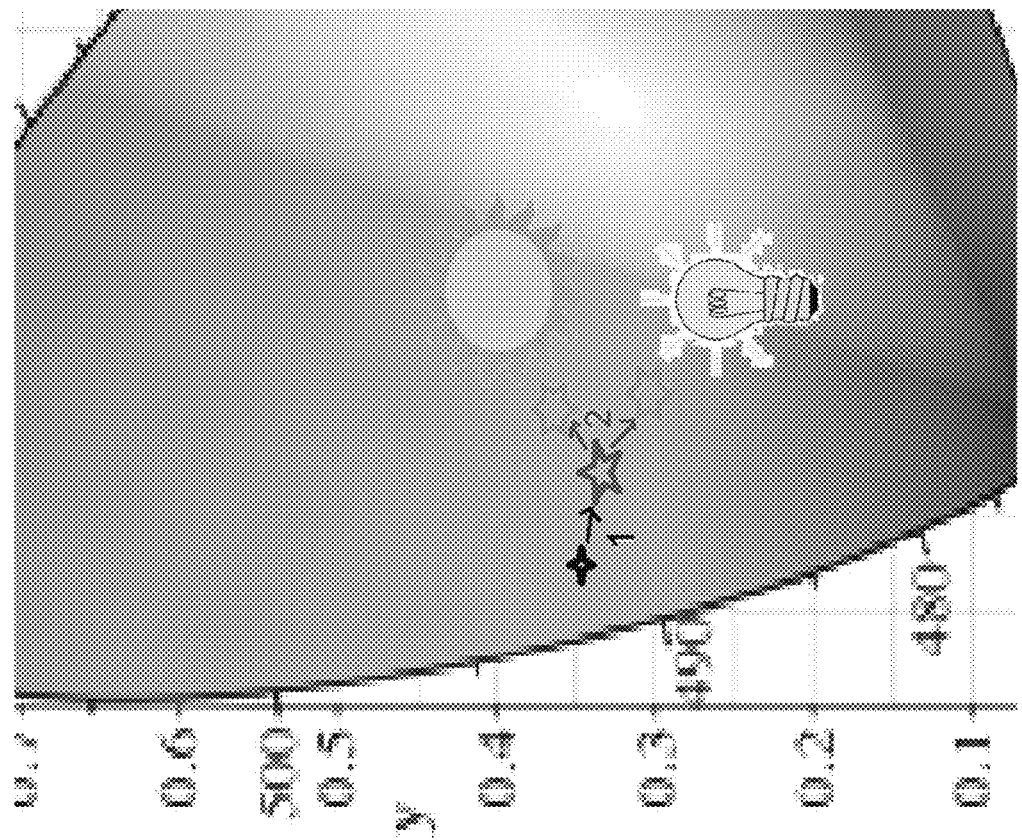
FIG. 43 illustrates chromaticity errors caused by an RGB camera.

An RGB camera effectively attempts to estimate the chromaticity coordinates of all objects in a scene. This estimate is notoriously noisy and error prone due to many reasons, with a significant reason being 'lighting.' This observation is illustrated in FIG. 43. FIG. 43 illustrates chromaticity errors caused by an RGB camera. The black and orange stars represent how the chromaticity value in color space provided by an RGB camera is different than the correct value (Red star). Due to errors within the camera, the actual value at the red star is misinterpreted by the camera to be the chromaticity value at the black star, even without lighting related errors. Additional errors in chromaticity measurement occur due to the type of light, as represented by the chromaticity value under natural sun lighting (orange star near sun graphic) vs. the chromaticity value under artificial lighting (orange star near the light bulb graphic).

The chromaticity is a 2 dimensional vector (e.g., in CIE coordinates, CIE_x and CIE_y), whereas the above described spectral ratios provide more useful N dimensional spectral ratio values for object surfaces, more stable relative to lighting conditions and with greater than 2 dimensions of 'useable signal.'

To provide a more reliable and accurate measurement of chromaticity, the N dimensional vector of spectral ratios obtained by the above methods are mapped into 2 dimensional chromaticity space. More generally, this mapping can be adapted to map spectral vectors into a variety of color space standards, such as CIE and others.

This colorimetric mapping is achieved by capturing standard color chart test patterns (e.g., Gretag-MacBeth or ColorChecker color rendition chart, etc.) with the above spectricity vector methods. A color mapping transform matrix is then derived to map the N-D vector into 2D chromaticity coordinates. Color images generated from this method provide more accurate colorimetric measurements using less reliable images captured through a Bayer sensor.

Once measured this way, the color temperature of the light falling onto a scene can be subsequently measured in the process. The methods of this disclosure enable the spectral composition of the lighting, including the ambient lighting to be measured, corrected and mapped into a color space domain in which the color temperature is computed.

As illustrated throughout this document, there are many applications of these techniques. The use of reasonably precise LED light tweaking without much regard to ambient conditions is a powerful feature. This can be leveraged significantly with machine vision techniques and some of our well-used correlation techniques. Machine vision can be used to stitch together (and optionally construct a 3D model from) many ambient+LED combined images taken by viewing a scene for several seconds. Exposure time and/or illumination period of LED (time a LED is turned on) for each frame can be optionally varied in some pseudorandom manner. After tying object pixels together through the many images with machine vision methods, the various LED reflectance values for each object point can be estimated with knowledge of the various exposure information. We elaborate on several more enhancement and applications below.

Errors in Spectricity Measurements and Various Approaches to Mitigating Those Errors Above, we described principles involved in measuring the spectral ratios and/or LED-pixel sensitivity ratios (the latter involving the wavelength-distribution mixing of LED spectra with the sensitivity profile of a pixel) of surfaces. This section provides further details on common error sources that often arise in actually implementing these principles, along with explications of approaches that can be used to estimate these error sources and mitigate them. The next two sections lay some groundwork for these topics.

Object Surface Changes Vs. Measurement Errors

The technical goal of spectricity measurement is to accurately measure the innate surface reflectance properties of some patch of a surface. A measurement results in a spectricity coordinate for a patch, also called a spectricity vector for that surface. Ideally, this vector is completely determined by the optical properties of the surface in question. At some level, all surfaces will have changes in their optical reflectance properties over characteristic time periods: a light grey patina developing on stainless steel cutlery over a few years versus a quick weeks-scale rusty reddening of an iron chain left out in the rain; quicker still, the hours-scale bruising of a fruit, and the seconds-scale blushing of a cheek. These intrinsic optical changes to surfaces are just what we are looking to measure; they are not error sources of course.

Errors can be broadly defined as any changes in a measured spectricity vector value for some specific surface which itself has no changes in its optical properties. There are numerous sources of errors within this broad definition and these sections will concentrate on some of the large error sources along with their mitigations. Three specific error sources and their mitigations will be described: 1) Field Angle Non-uniformity; 2) Surface innate-reflectivity non-linearity; and 3) Surface Normal effects due to undersampled Bi-Reflectance Distribution Functions (BRDF) (to be explained in its own section).

Figure 44:
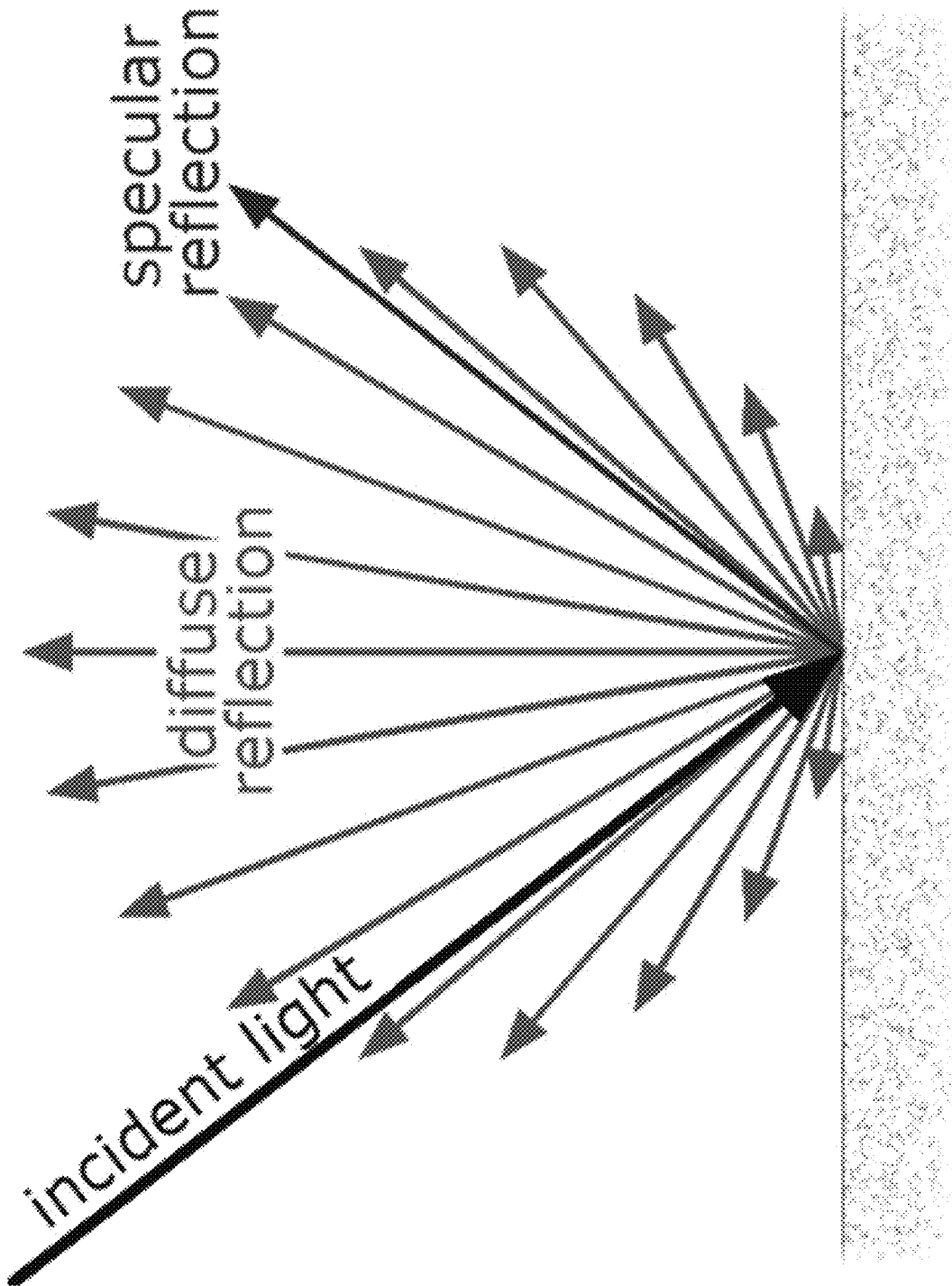
FIG. 44 depicts that an incident beam of light (e.g., from a focused LED) generally gives rise to specular and diffuse reflection.

Light Reflectance and a Split Between Specular and Diffuse Reflection; the Bidirectional Reflectance Distribution Function FIGS. 44-45 below provide further context for the ensuing disclosure. FIG. 44 depicts that an incident beam of light (e.g., from a focused LED) generally gives rise to BOTH these two types of reflection—1) specular, as if the surface was a mirror, and 2) diffuse, as for a tough surfaces; different surfaces have different ratios of how much light reflects into these two modes.

Figure 45:
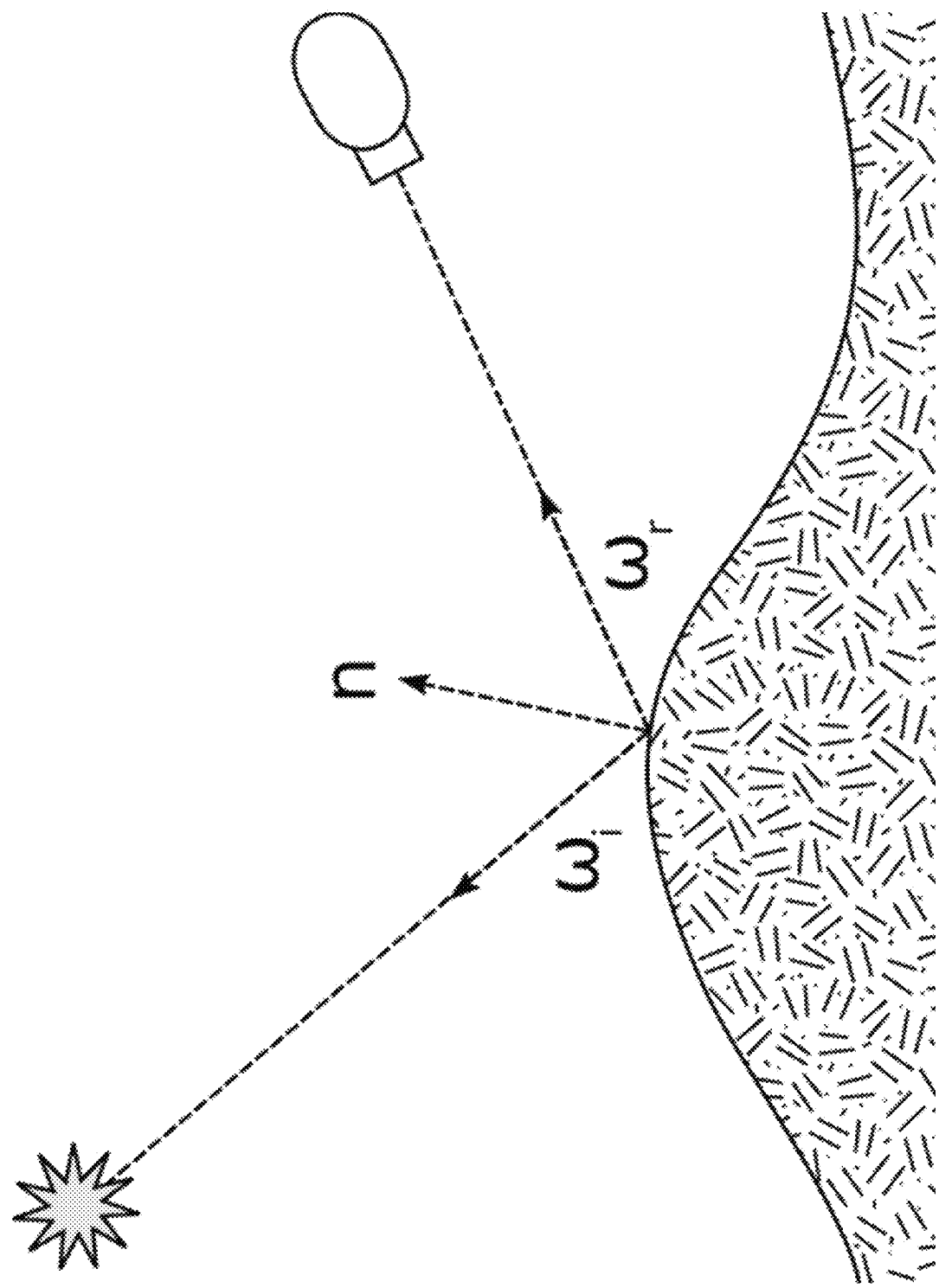
FIG. 45 is a diagram illustrating an example of how much light from one angle, Wi, gets reflected into another reflectance angle Wr.

As depicted in FIG. 45, extremely precise applications can be even more specific in describing how much light from one angle, Wi, gets reflected into another reflectance angle Wr. This is the somewhat arcane 4 dimensional 'Bidirectional Reflectance Distribution Function'. In smartphone implementations, with the lens and the LED source being nearly co-located, Wi and Wr are almost identical. LEDs and cameras do not necessarily need to be co-located, and hence the fuller BRDF view can be important to understanding spectricity error sources.

FIGS. 44 and 45 briefly summarize some salient properties of reflected light. In each figure, an idealized illuminator comes from some specific 'ray angle', giving rise to scattering of light into all angles. FIG. 45 depicts a light detector which presumably can vary across all angles Wr. The full BRDF becomes a four dimensional function once the hypothetical light source direction onto the surface also varies across all angles, with each incident light angle (Wi represented by two variables) reflecting light into all angles (Wr represented by two more variables). Indeed, as pertinent to this disclosure, it becomes a 5 dimensional function once wavelength-specific measurements are considered. This spectral aspect can be approximated to be nearly uniform across wavelengths but for many spectral imaging applications, this might be a poor assumption and further errors in spectricity measurements will result.

One main point for this disclosure is that many configurations of this technology posit a single camera and a generally-singular, compact LED lighting unit. In mathematical terms, such an arrangement posits lighting a given surface from one specific angle Wi, then viewing that surface from a typically co-located or equal angle Wr to Wi. The resultant measurement from that specific point in the 4 dimensional BRDF then becomes a proxy for all values in the BRDF. To the extent this singular measurement cannot properly describe the aggregate reflectance properties of a surface as represented by the full BRDF, then such discrepancies must be chalked up as error. This disclosure refers to this error source as 'undersampling the full BRDF'. There is yet a fifth dimension to the BRDF once one considers monochromatic light as the incident light, as already noted. To the extent the BRDF is rather similar from one wavelength to another, or not, this will be a factor in the extent of error introduced by this particular source of error with regards to spectricity characteristics of surfaces.

At an academic level, the undersampled BRDF source of error can appear to be rather egregious, and indeed, for very high end applications such as chemically designing inks and paints for example, these potential errors can be quite important. But fortunately for many other applications such as mobile device identification of common objects and surfaces, the specular versus diffuse error-source situation depicted in FIG. 44 is more practical concern than the errors due to undersampled BRDFs.

Field Angle Non-Uniformity Error and Mitigation

One of the principles of this disclosure posits that one given LED will differentially (by adding to ambient) illuminate surfaces in a scene, followed by another LED, then the next, etc. An implicit but here now explicit idea behind this is that the generic ratios of illuminating 'differential light tweaks' remain relatively constant with both distance of a surface from the camera/LED combination, as well as from the center of a scene out to the edges of a scene (i.e., the surfaces illuminated position in a scene relative to the center of the scene). For all physical realizations of this technology, this perfect constancy of LED illuminant ratios is not possible once one considers the situation at the few percent level (percent differences in ratios for example). The consequence of this deviation from strictly uniform lighting is that the raw measurements of spectricity vectors on otherwise identical surfaces will change both with distance and with what common practice calls 'field of view angle'. In general, the latter effect of changes due to field of view is more pronounced than the changes as a function of distance, but this is ultimately a function of details of how the optics of the illuminating LEDs are designed (e.g., broadly diffuse lighting versus 'focused spotlight', as but one example). Distance changes may become as important as field of view angle changes, in other words, it will be application and lighting design dependent.

Figure 47:
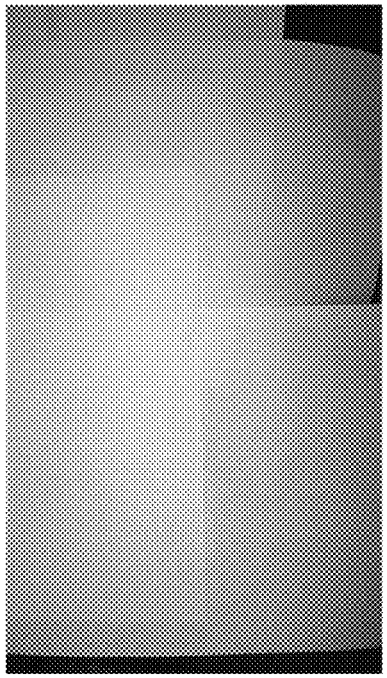
FIGS. 46, 47 and 48 provide visible examples of the field angle non-uniformities.
Figure 46:
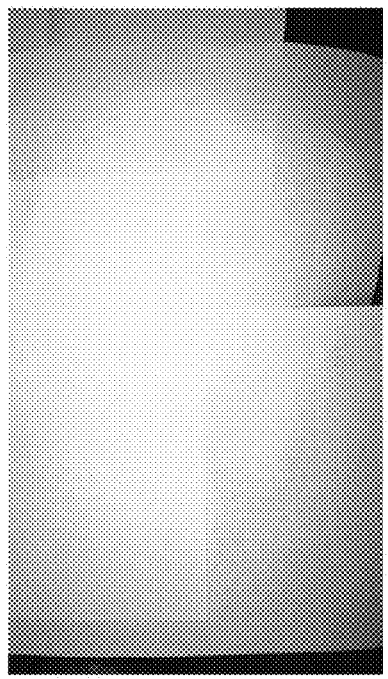
Figure 48:
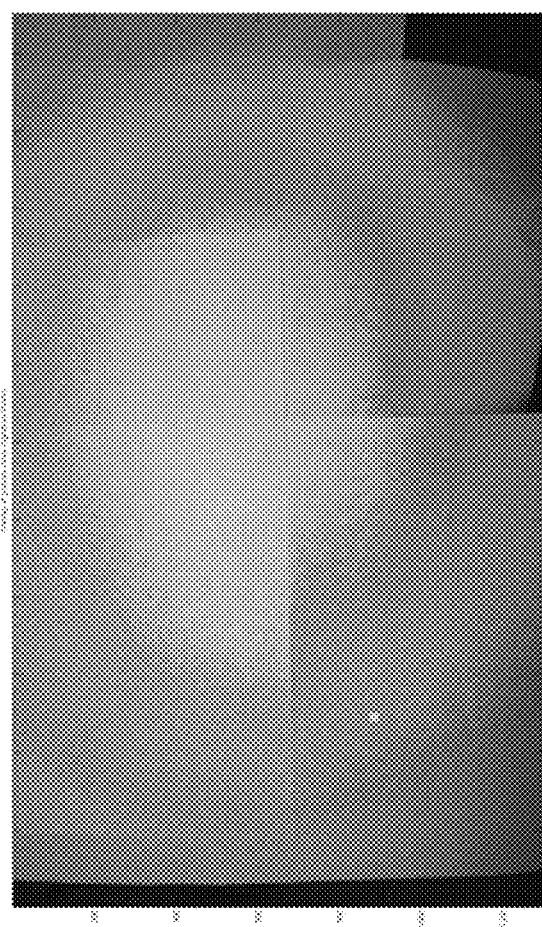

FIGS. 46, 47 and 48 provide visible examples of the field angle non-uniformities. Figures after these abstract the notions and lead to a variety of solutions to mitigating errors introduced by these unavoidable physical effects. Ordinary sheets of paper are used for several reasons not least of which is that they could quickly prove a few points. There is in fact edges and details in the images, but the overall field angle non-uniformities can still be illustrated as well.

FIG. 46 depicts green LED differential lighting of some white paper sheets. This lighting is in addition to a modest level of 'normal' ambient diffuse lighting. Hence the LED lighting is differentially modulating the pseudo-uniform scene. In practice, a uniform white surface, commercially made white targets, or simply 'good enough for any given application' white surfaces, can be used as a scene.

One can visibly see in FIG. 46 that a normal kind of brightening in the middle of the scene is surrounded by an equally normal dimming as one moves out from the center.

FIG. 47 depicts the same scene as FIG. 46, but now differentially lit by a blue LED one frame in a video sequence later, where the pulsing of the LEDs are coordinated with the framing of a camera—a Bayer-pixel color camera in this case. The LED part used in both this figure and the last has seven 200 micron by 200 micron active LED 'chips' tuned to different modestly narrow bands in the spectrum. The placement of the LEDs are in a small ring of approximately 3 millimeter breadth, where physical wires/leads are present in the direction of illumination, i.e., the wires subtly affect the far field illumination pattern.

Comparing FIGS. 46 and 47 is of course not easy without further instrumentation to assist, but suffice it to say that the detailed illuminant profile of the green LED, referenced say to its peak illumination point in the scene, is definitely different from the blue illuminant profile if one considers those profiles at the ~1 to 10% difference range. Likewise, the same is true for the other 5 LEDs in the particular 7-element part used in this example. One can appreciate that even the flatness of the 200 micron active elements will produce an ever so slight shift (perhaps 5 to 10 degrees) in the precise peak location of its light energy in the far field.

The same process used to obtain the images of FIGS. 46 and 47 is used to obtain images for three other LEDs, which were used to illuminate these sheets of paper.

FIG. 48 provides an 'iso-spectricity overlay' image of the processed scene.

More specifically, FIG. 48 depicts an iso-spectricity overlay image of the white sheets of paper, each separately illuminated by the 5 LEDs. The ambient lit scene is the backdrop, whilst a 15 dimensional vector value of a random point in the center of the scene is used as a 'reference value' and all the other measured spectricity vectors in the scene are compared to it, with simple Euclidean distance used as a modulator on the 'red' that gets overlaid into the image.

Those practiced in the arts of lighting, image measurements, chromaticity measurements and even those schooled in higher dimensional vector mathematics can all appreciate that there is a great deal more that could be explained here; later sections will indeed explore more on 'iso-spectricity' visualization for example. BUT, the point for this section is that FIG. 48 clearly and intuitively shows that for even normal white sheets of paper which 'should' have relatively uniform spectricity signature vectors, raw measurements of those vectors appreciably change as a function of field angle.

The magnitude of these changes are somewhat exaggerated in FIG. 48 in that the iso-spectricity thresholds that needed to be set can zoom in on the 'couple to few digital numbers' range, right close to the noise floors of most normal cameras, and hence even a few percent change in uniformity between one LED and another can produce the obvious effects illustrated in FIG. 48.

So, knowing that these non-uniformities can produce tangible errors in spectricity vector measurements, we proceed to a discussion of what can be done about them.

Figure 49:
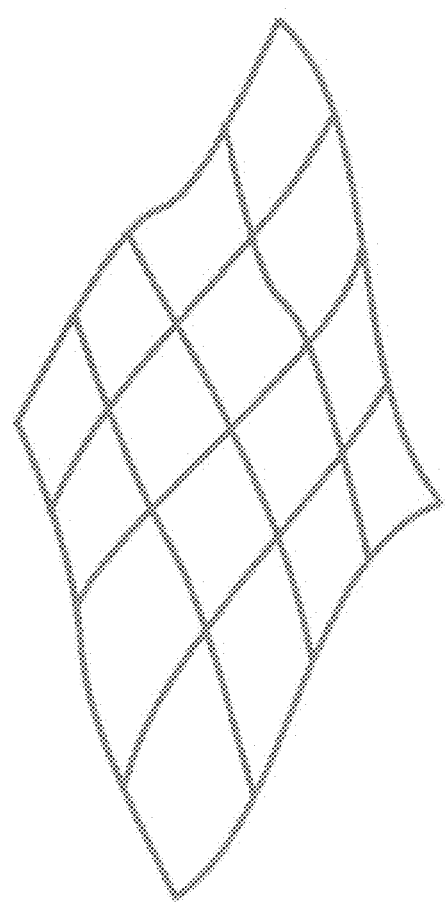
FIG. 49 contains a summary of largely what FIGS. 46-48 have shown experimentally, followed by further figures and explanations of both theoretical procedures and actual calibration procedures that can be performed to mitigate these errors.

FIG. 49 contains a summary of largely what FIGS. 46-48 have shown experimentally, followed by further figures and explanations of both theoretical procedures and actual calibration procedures that can be performed to mitigate these errors.

FIG. 49 is intended to illustrate the following: Finely conducted experimental procedures on calibrated 'white photographic panels' show that as one performs the operations to obtain spectricity values on such a white panel, one will produce a curved/warped 2 dimensional sheet of spectricity values in N-dimensional space, where N=15 in the previous figures. The N-D Spectral Signature of the image of a 'white sheet' should all be the same, but even the most calibrated camera with the most calibrated lighting will produce a resultant 'sheet' in N-D Spectricity Vector Space (or its 'Signature'). Even the most carefully designed uniform illumination system will still have measurable non-uniformities if one pushes hard enough to find them. These non-uniformities are depicted in the distortion of the sheet in FIG. 49.

FIG. 49 is making an implicit point: For a relatively fixed physical arrangement between a camera and some given multi-LED illumination unit, a relatively stable calibration of the non-uniformities can be measured and ultimately 'displayed' or at least conceived of as a 2 dimensional warped plane in an N dimensional space. There is little need to actually try to visualize such a sheet, but there are in fact ways to try to do this visualization that will be touched upon in subsequent sections.

Practically speaking there are both theoretical ways of approximating the numeric behaviors of these 2D warped sheets (through knowledge of the design of the LEDs, its illuminating patterns, and the like), but more importantly empirical ways to measure these sheets in ways that are pragmatically stable for weeks, months and perhaps the lifetimes of any given physical arrangement, smartphone based or otherwise. One can imagine making and storing actual measurements of the calibrated white panels at all the cross-points in the depicted sheet above. One can also then 'curve fit' 2 dimensional sheets within the N-dimensional space to the measured data, thus smoothing out high frequency errors in the measurement of these sheets and arriving at a mathematical description of the specific sheet for a specific camera/LED unit combination.

Figure 50:
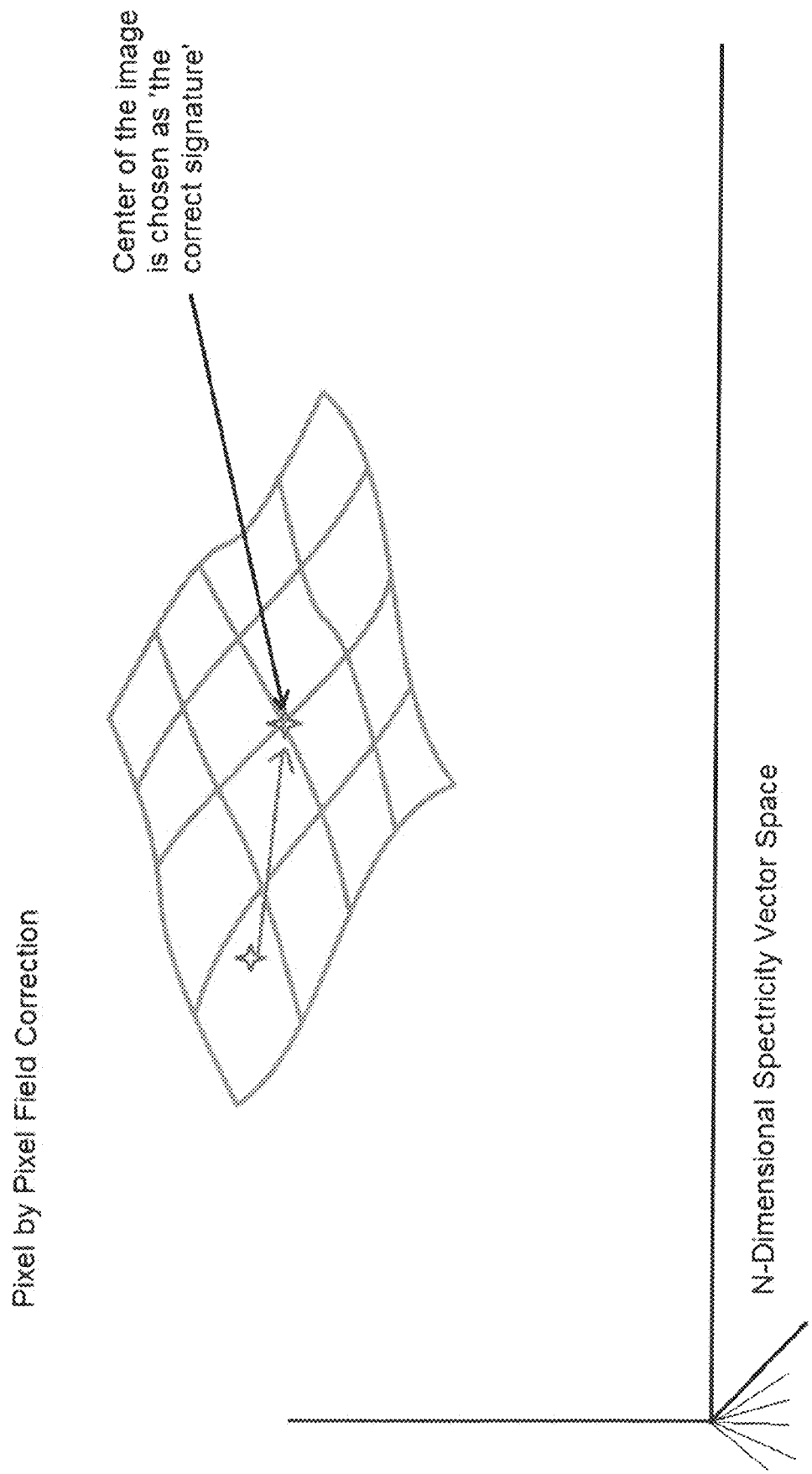
FIG. 50 provides an illustration that explains a process of field correction.

FIG. 50 provides an illustration that explains a process of field correction. After a camera/LED's warped sheet has been measured, reduced and stored, then all subsequent spectricity measurements using that camera/LED apply correction vectors as a function of field angle, using an arbitrary reference point such as the 'white' spectricity vector value found at the center of a scene. All other field angles get corrected to this center point.

FIG. 50 also helps illustrate how 'stored sheets' become a kind of look-up-table that become spectricity vector correction values to all subsequent measurements made by the camera LED combination. Those practiced in the art of light measurement fully understand that there will still be finer-scale error sources involved with these kinds of correction operations, and specifically that corrections applied to 'effectively white' surfaces may differ measurably from surfaces that have more complicated spectral structure, but the point of this section is that the gross behavior of field angle errors can be mitigated if not entirely removed. A rule of thumb design target for common commercial applications would be to mitigate 'spectricity blurring' as a function of field angle by up to an order of magnitude, if possible. Intuitively, as well as empirically, one can appreciate that if these procedures are followed and subsequently a 'red sheet' or a 'green sheet' is measured by a so-calibrated camera—LED pairing set-up, the resultant 'spreads' of the spectricity vector values of those sheets should be nearly an order of magnitude tighter in comparing raw vector value spreads to calibrated spreads. At the end of the day, 'error mitigation' largely boils down to such measurement and verification considerations. As shown in FIG. 50, the signature at a point near the center of the image is chosen as the correct signature. In this process of pixel by pixel field correction, all other pixels in the image get a correction vector applied to them due to the field non-uniformity (the blue vector applied to the red pixel corrects its value).

Figure 51:
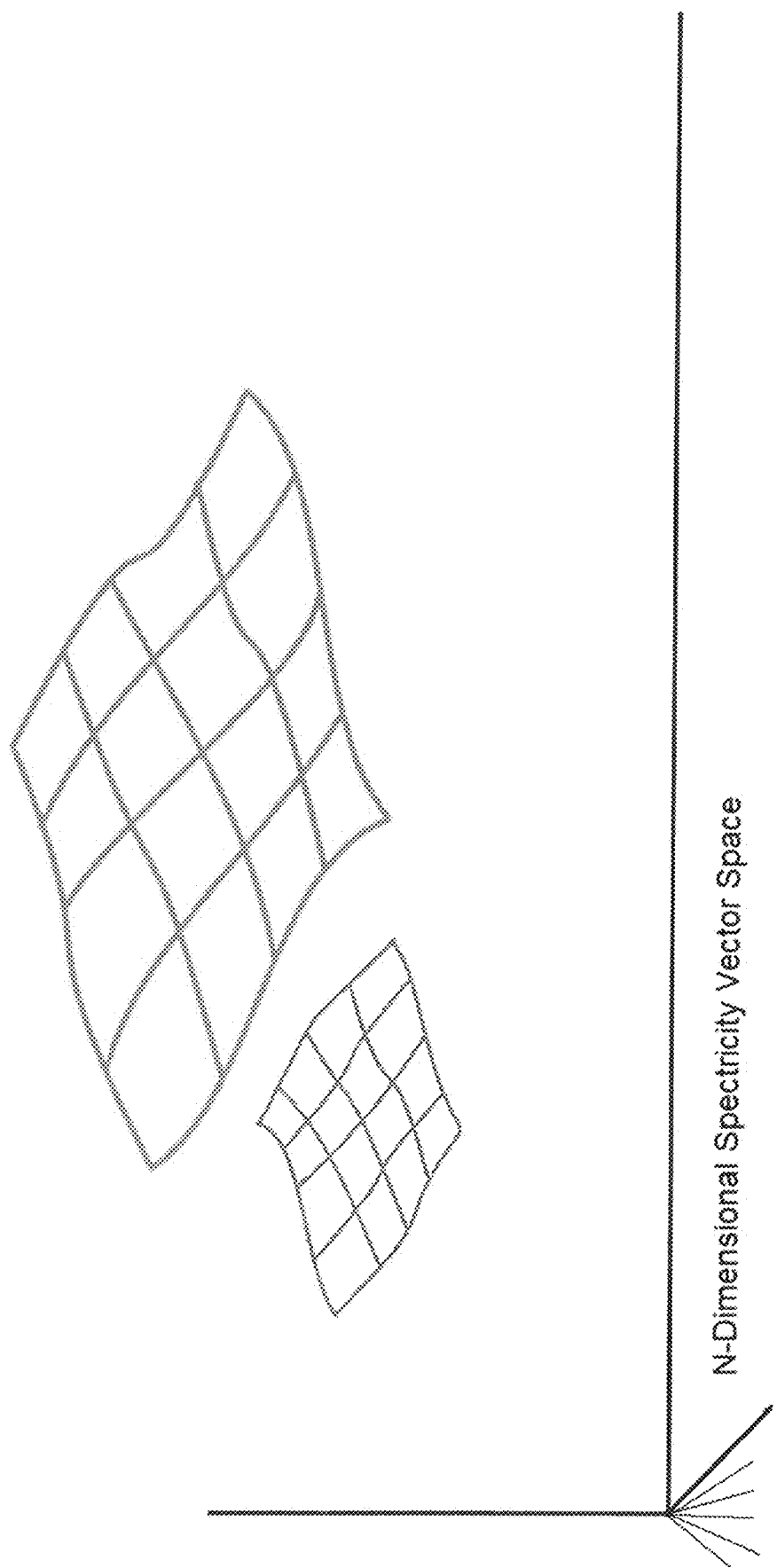
FIG. 51 depicts spectricity errors caused by gross reflectance values (i.e. lightness-darkness of surfaces).

FIG. 51 next delves into the slightly counter-intuitive but all too prevalent situation where the level of reflected illumination from a surface, as well as the detailed linearity behavior of normal cameras, can produce additional errors in spectricity measurements which also thankfully can be mitigated.

FIG. 51 depicts spectricity errors caused by gross reflectance values (i.e. lightness-darkness of surfaces).

FIG. 51 explains that if we now replace the bright white panel with one which is a mid-level and still calibrated 'grey', virtually every reasonably precise (modest laboratory/dark-room setting) will exhibit measurable shifts in spectricity vector values between the sheet measured with the white panel and the 'new grey sheet' measured on the grey panel. A similar effect happens when a 'grey sheet', with identical spectrum to a 'white sheet', has its spectral signature measured: its sheet shifts around in 'signature space'. This is also due to ever-so-slight non-linearities even in high end 'gamma=1' cameras. The degree of this effect is rather exaggerated in FIG. 51, but the point is made. Indeed, it is a testament to the higher fidelity measurement capabilities of even normal smartphones that these slight shifts can even be measured at all.

There are a variety of causes of such shifting, as with the white panel already described. A leading cause is simply is that the silicon sensors inside every camera always have some level of non-linearity if only at the physics level of the pixels (which is a very small non-linearity indeed). For many applications the degree of reflectance level error may be too small to care about, for others it may be necessary of measurement and mitigation.

Figure 52:
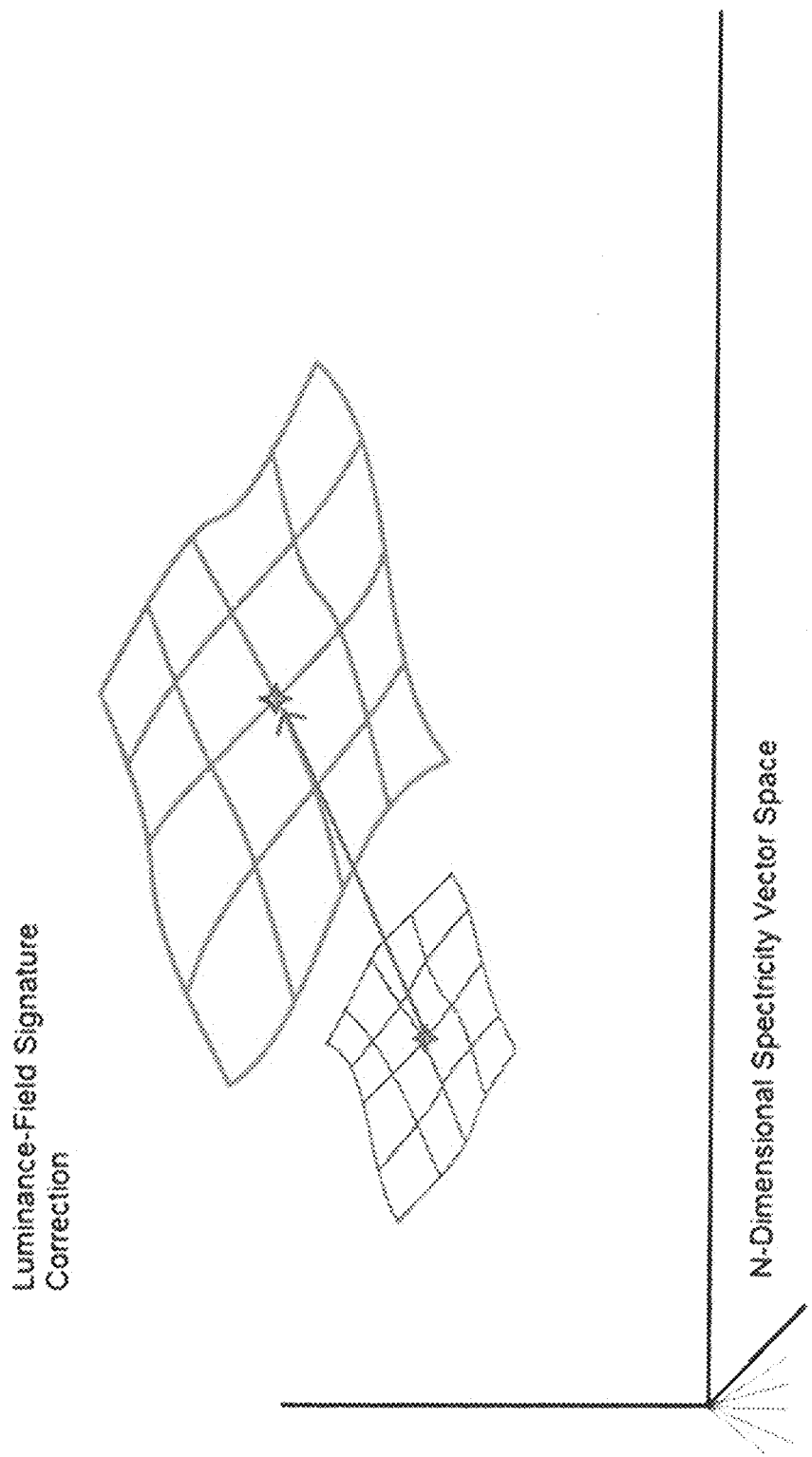
FIG. 52 depicts reflectance-level spectricity vector correction.

FIG. 52 depicts reflectance-level spectricity vector correction. Inherent luminance of the reflected surface point also becomes a factor in calculating then applying the signature correction vector for all pixels (corrected to the 'full white' center pixel, an arbitrary global standard point). This correction process uses a similar process as the one for FIG. 50. As with FIG. 50, additional 'grey level sheets' (often just two or three can nicely sample the range from black to white) are measured, stored, then a given measured spectricity value. These volumetric correction maps are created by literally putting white sheets and calibrated 'grey sheets' directly into the stage of the camera/LED set-up and collecting the appropriate data. The correction process accesses those sheets and generates an appropriate correction vector.

Both the raw ambient luminance channel of a scene, as well as the total reflected LED signal level as determined after an LED cycle has been captured, can be used to provide a measurement of the reflectance level of a given surface in any given part of a scene.

One final important point in this section on mitigation of errors due to field angles and innate surface luminosity is that the vast variety of commercial cameras, both color and black and white, all one way or another have been designed with the human visual system (HVS) in mind and they all have their own brand of camera specific image processing. This is a category of image processing that is programmed into modern cameras to tune camera performance. Yet this image processing (e.g., camera specific image correction designed with HVS in mind) are all potential sources of error in spectricity measurements if they are not either turned off or otherwise factored in to the measurement chain of spectricity vectors. Auto-gain, white balancing, nearest neighbor Bayer processing, gamma, are a few of the examples of such processing. Some but not all of the measurable effects illustrated in FIGS. 46-52 can trace their roots to these internal camera processing functions. Gamma in particular is an important issue and other sections of this disclosure discuss its ramifications and corrections, as one example.

The baseline rule is: If a given reference surface with stable physical properties nevertheless has differing measured spectricity vectors as a function of some discernible environmental condition, the cause, then that cause becomes a candidate to objective measurement of its induced spectricity vector changes and then subsequent mitigation. This generic baseline rule is clearly applicable to all empirical measurement arrangements of course, but its applicability to this disclosure is made explicit.

Specular Versus Diffuse Reflection Ratios

Recalling FIG. 45, the specular versus the diffuse reflection characteristics of various surfaces are rather important to understand and wrap into the baseline principles of this disclosure. Those of us having the privilege of normal vision have an intuitive connection to these differences in reflective properties, largely summarized by the degree of shiny versus matte of surfaces and everything in between.

Fundamental physics teaches us that the spectral content of diffuse versus specular reflection from most if not all surfaces will differ from each other if not largely then at least at the finest spectral discrimination scales. A driving reason for these differences is that specular reflection tends to be more involved with the physics of air-matter surface phenomena, while diffuse reflection tends to deal more with surface penetration and subsequent interaction (often absorption) with near-surface matter. At a crude high level, specular reflection tends to exhibit more pan-spectral uniformity than the more spectrally-selective properties of normal matter.

This all matters to this disclosure for a classic double-edged sword pair of reasons:

1) A given physically stable surface can have significantly different spectricity vector measurements depending on whether or not the camera-LED combination is 'normal' to a surface versus at some angle;

and

2) These differences in spectricity can be exploited in a variety of ways, most notably in that they a) provide additional information on surface topologies and b) 2 dimensionally sample overall 3 dimensional object properties as projected onto the camera, both of which can greatly assist in object recognition among other things.

So the pseudo-negative side of that double edged sword, the practitioner can expect measured spectricity vectors of surfaces to vary as a function of the surface-normal vector relative to the camera center-axis. This will be the case specifically for set-ups where the LED unit is co-located with the camera within a centimeter or two laterally to a camera lens, or even LEDs circled around a lens.

Figure 53:
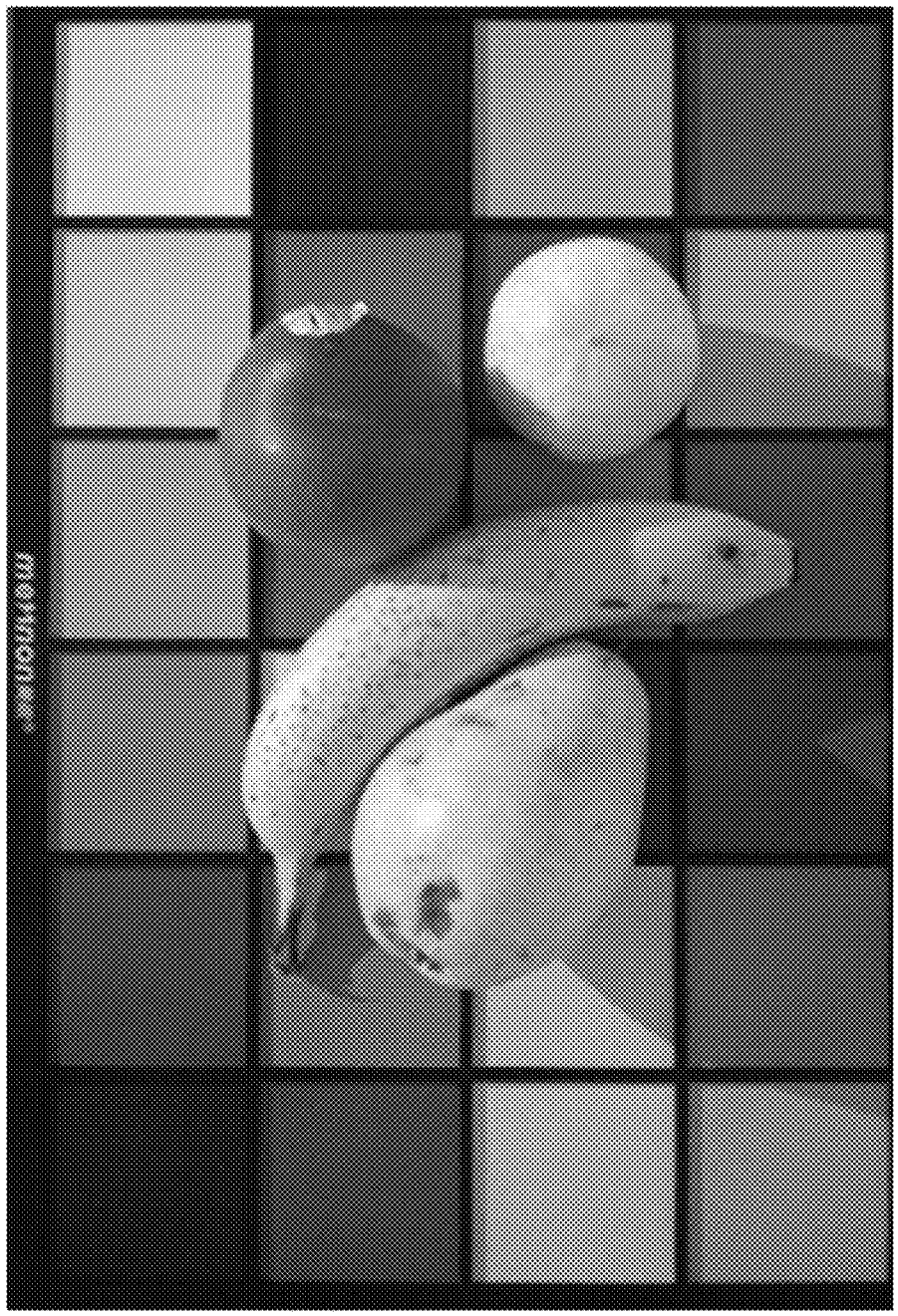
FIG. 53 depicts an image of a scene taken with a normal Bayer-type color camera.

But before diving in further, FIG. 53 attempts to further ground these concepts:

FIG. 53 is a normal color photograph of a scene with both diffuse ambient lighting as well as one distinct thermal light source casting shadows. The intuitive notion of specular reflection can clearly be seen as a white-ish glint on the pear as well as on the nectarine.

FIG. 53 grounds us in our intuitive notions of specular versus diffuse reflection. Images of billiard balls work nicely in this regard as well. The image of FIG. 53 was taken with a normal Bayer-type color camera. The existence of shadows brings out the further subtlety that some level of diffuse reflection can derive form the thermal source, while other reflections in the shadows are mainly from ambient diffuse reflection.

Figure 54:
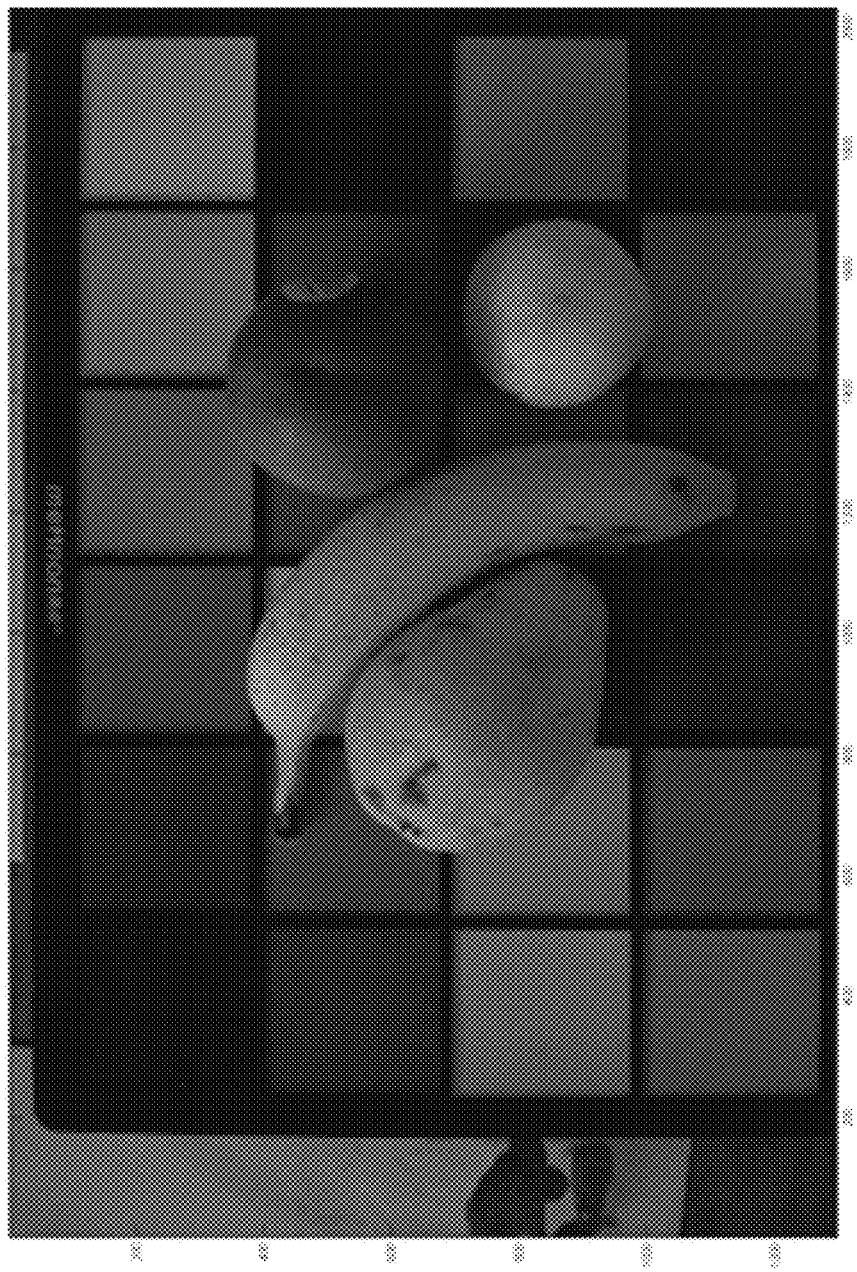
FIG. 54 depicts an image of the same scene as FIG. 53 but with the ambient light significantly dimmed.

FIG. 54 is an image of the same scene and camera set-up as FIG. 53. Now the ambient light has been significantly dimmed and is largely determined by a distant thermal light source, itself reflecting off of a broad ceiling. This 'ambient lit scene' will now be studied and used for explaining further inventive aspects of our technology.

FIG. 54 now sets the stage for not just discussing the specular versus diffuse reflection issue, but also for further practical details on spectricity measurements and their resulting properties.

The ambient lighting evident in FIG. 54 gives rise to pixel values in the upper right white panel in the 100 to 130 digital number range on a 255 8-bit scale. Subsequent additional illumination of this scene by 5 different band LEDs gave rise to an increase in 'average' digital numbers of pixels by roughly 20 to 30 digital numbers all depending on wavelengths and the R's, G's and B's that preferentially responded to the various LEDs and color patches. At a crude high level, the 'differential tweaks' from the LEDs, obtained by subtracting the ambient frame from the individually lit frame, was on the order of 20% to 25% of ambient. A long term goal is to see if these differential tweak levels can approach 10% of ambient, but 20% to 25% is a good place to start.

Figure 55:
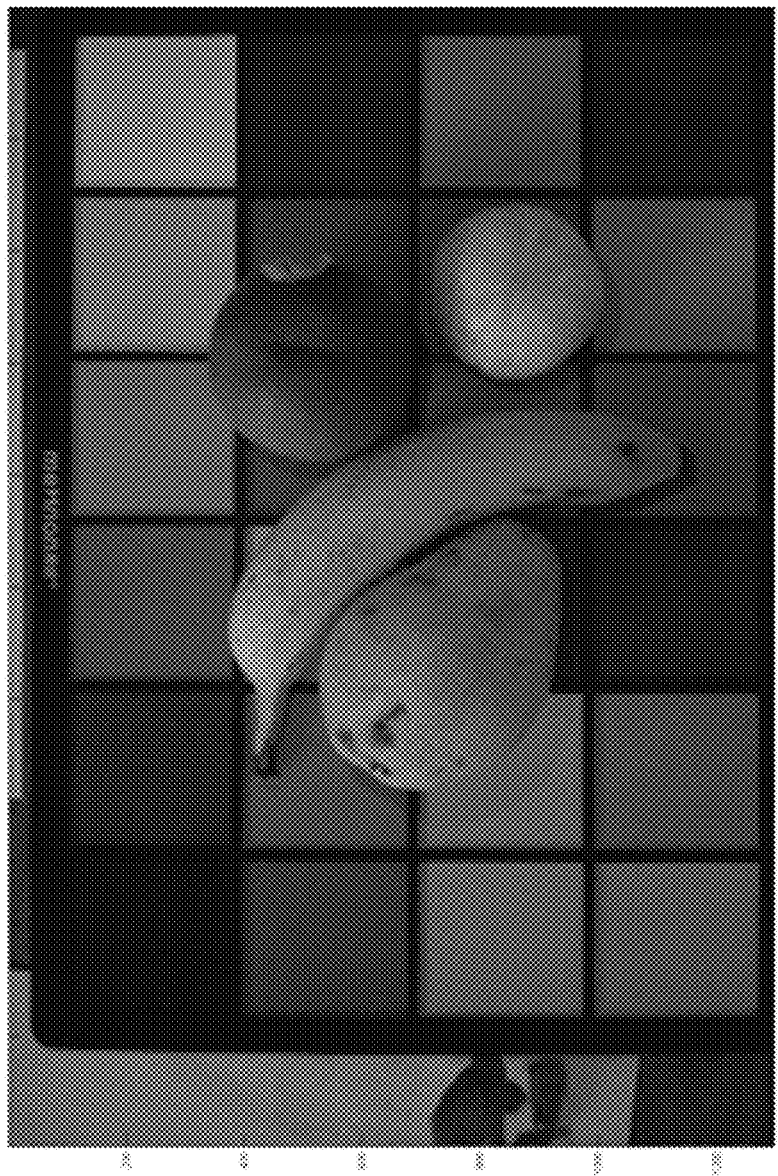

FIG. 55 is an image obtained from the same ambient lit scene as FIG. 54 but now with the 'differential tweak' of the blue LED turned on. The measurement set-up here had the scene at about 20 inches from a normal Bayer camera, while the LED unit was displaced by about three inches. Smartphone integration or 'rings of LEDs around lenses' will not have nearly this level of separation, but for these studies and for explaining the principles in our disclosure, this separation can prove useful, starting with noting 'the shadow' in the light green panel to the lower left of the pear: the pixel levels in the shadow next to the pixel levels in the 'lit' side of this green panel clearly illustrate the ~20 to 25% level of differential tweaking of the scene.

FIG. 55 has four other counterpart images where 'red', 'amber', 'green' and 'yellow' LEDs were individually lit. Just for further illustration, FIG. 56 shows the green tweaked image.

The Green LED tweaked image of FIG. 56, taken less than one second later than the ambient image of FIG. 54 and the blue-tweak image of FIG. 55. The timing is not critical for these set pieces but the broader idea remains that the LED tweaks are either frame synchronized with a camera, or, at least timed such that individual LED tweaked data is derived from the raw imagery itself (see demux discussion herein), as is often the case with rolling shutter image data where part of a frame has good 'full tweak' data and other parts may have none (as a function of scan lines typically).

Figure 56:
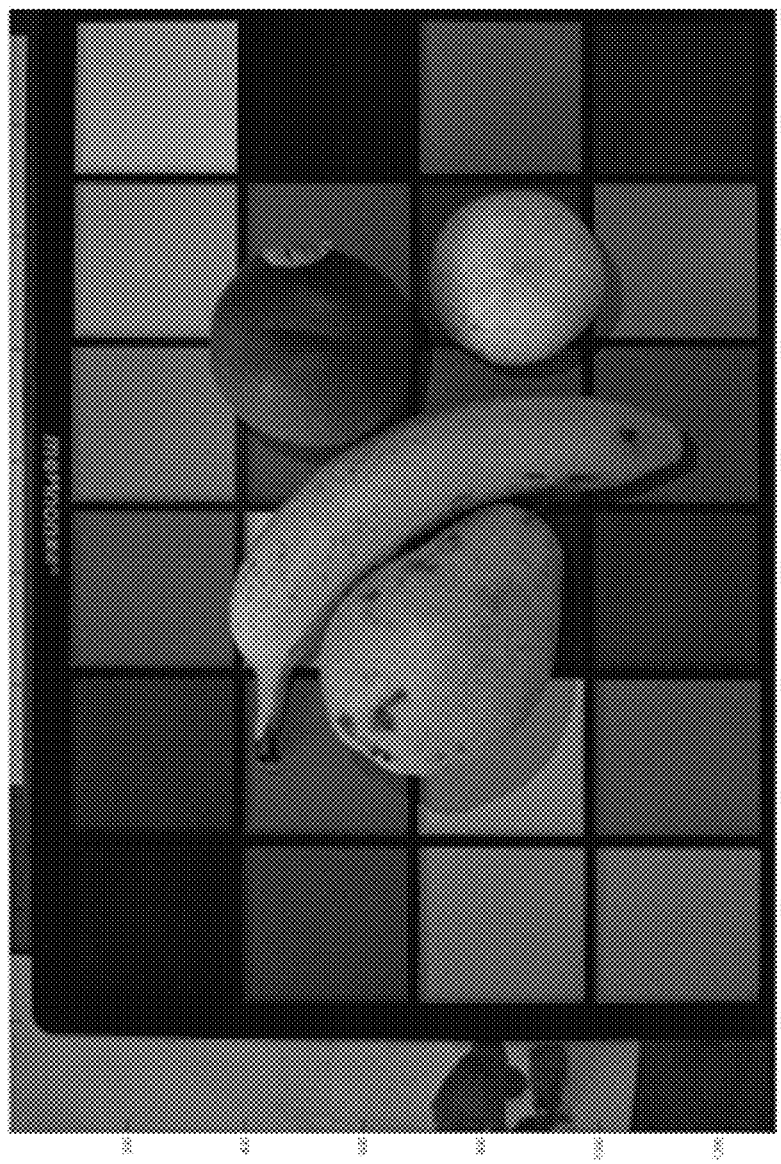

Getting back to the theme of this section, specular and diffuse reflection, examination of FIGS. 55-56 shows that the subjective location of the 'specular shininess' on both the pear and nectarine have both shifted from their locations evident in FIG. 53. Also, at an intuitive level, one can see in both FIGS. 55-56 that this new location is much closer to the 'surface normal' of these two fruits, relative to the camera main axis. Thus, the specular reflection is closer to where we expect it to be.

One mitigating factor in the negative-side view of specular versus diffuse reflection begins to reveal itself in FIGS. 55-56. That is, all things considered, the specular shiny spots are not too big at least relative to the full sizes of the pear and the nectarine in these examples. These types of effects, as described for similar effects, are detected and mitigated, as appropriate, to achieve the broader goals of most applications: identification and evaluation of objects.

Figure 57:
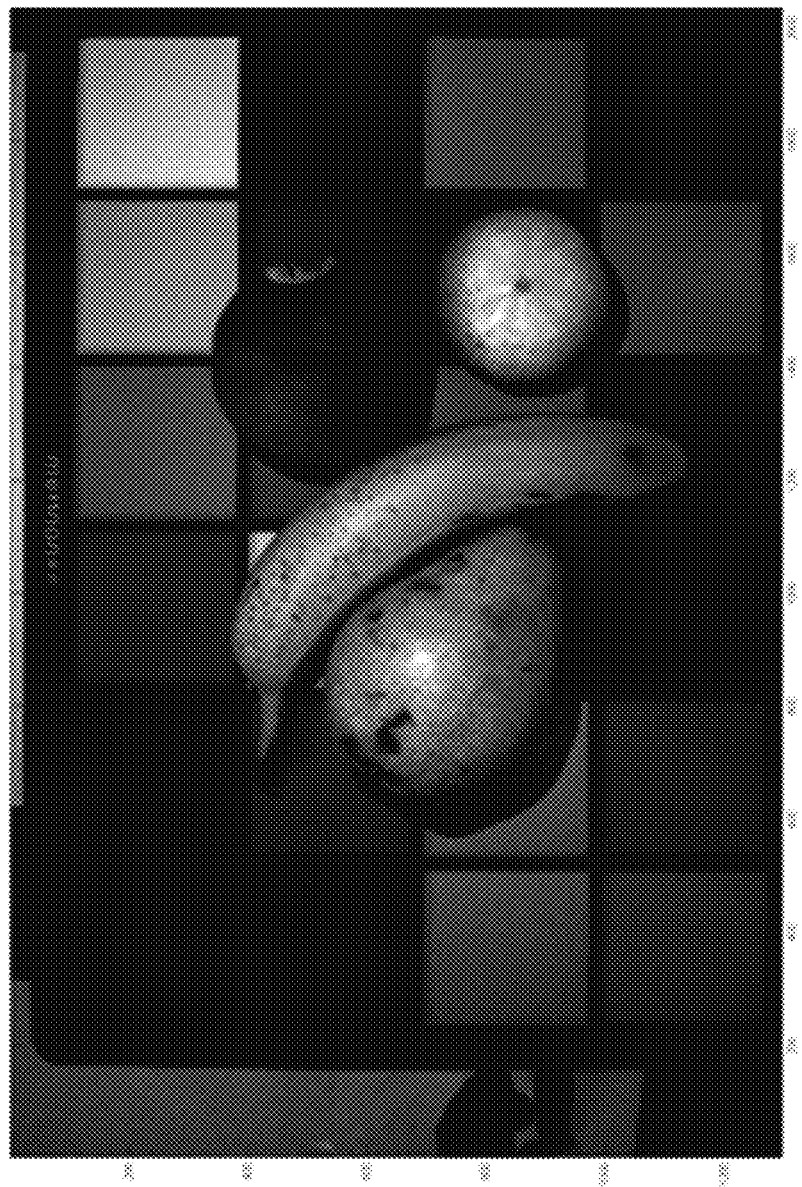
FIG. 57 depicts the sum total of the increases in pixel values measured for each of the 5 LED-ambient images (their raw digital number increases across R, G and B values), displayed as a black and white image.

The total sum of only the differential LED light tweaks is now presented in FIG. 57. Specifically, FIG. 57 depicts the sum total of the increases in pixel values measured for each of the 5 LED-ambient images (their raw digital number increases across R, G and B values), displayed as a black and white image.

FIG. 57 is interesting in many ways but not least for its additional evidence of the differences between specular and diffuse reflection effects. If we take the reasonable assumption that most of the camera processing non-linearities have been accounted for in the differencing operation producing the so-called 'pure' LED-tweak images (basically FIG. 55 minus FIG. 54, FIG. 56 minus FIG. 54, and likewise with the three other LEDs), then FIG. 57 is a good representation of 'just the added light from the LEDs', all put on top of each other. This was our flashlight made up of five individual LED flashes.

Given the rather dim condition of the outer-field patches and the borders, it can be appreciated that even in 20% to 25% LED tweak to ambient conditions, the resultant LED tweak data is pretty low except in those areas closer to the LED flash/camera unit, and obviously of a whiter nature. Thus, one aspect of this disclosure is here illuminated, that being that weaker signals can be more of the norm than the exception as various practical applications will not be tolerant of 'battery draining and eye-blinding' LED flashing.

An additional explanatory benefit of FIG. 57 is that this frame, augmented by the value '1' in any pixel location that might happen to come out as 0 due to normal noise, is precisely the 'sum' frame that all other differential frames will be divided by in order to obtain raw spectricity values for individual patches in the scene.

Concluding this section on specular versus diffuse reflection at least in terms of the negative-side of 'error sources', we finish by noting that methods can be designed to measure/identify patches within images captured by these methods which are more prone to specular reflection and which are oppositely prone to diffuse reflection. In particular, ratios between the two are estimated on a scene-patch by scene-patch basis. Then furthermore, the resultant measured spectricity vectors for those given patches are thus 'labeled' by their S to D type reflection propensity. Object-type specific characterization can then be performed based on how spectral content changes as a function of moving from S-type reflection to D-type reflection.

More on Under-Sampled BRDFs, Potential Spectricity Vector Errors

Returning again to FIG. 45 and related discussion, at the heart of the definition of the BRDF is the notion of the surface normal and various orientations relative to light source and observer. This in turn emphasizes 3 dimensional space and that these entities must be described in 3 dimensional space.

The negative 'error inducing' aspect of under-sampled BRDFs has already been introduced. Reviewing FIG. 45, to the extent a spectricity vector is measured for some specific lighting and viewing angle, the assumption is made that the measured value is reasonably correlated to all other—at least diffuse—locations in the four dimensional BRDF. Again, from some amount of experience of applicants, this is a decent assumption for many surfaces, bearing in mind the previous discussion on how specular reflections might creep into any given situation. When large aggregates of patches are sampled presumably belonging to an integral objects, presumably having a reasonably similar spectral profile on most exposed surfaces, then a de facto larger sampling of a population of related BRDFs is happening by simply forming 'an image' of the spectricity vectors. In most cases, the specific orientation properties of the object and its surface elements is an initial unknown, but normal morphological reasoning suggest that if one is taking a picture of a pear, then a de facto sampling of patches will see patches ranging from those aligned with the camera axis to those 'at the edges' and perpendicular to the camera axis, then all surface normal in between those two. Purely circular objects like billiard balls have quite predictable distributions of those surface normal whilst heavily folded hot green peppers may not. The overall point relative to 'error mitigation' for individual patch spectricity measurements is that 2-dimensional and/or 'spatial/structural' information of the underlying image itself can assist in sleuthing probable surface normal estimates for given patches, then using these estimates again as effective 'labels' on measured spectricity vectors. A large fuzzy histogram bin can be set around surface patches with ~45 degree angles plus or minus 30 degrees for example, with such wide margins still being useful to higher level object recognition algorithms. Some information/estimates will be better than none, especially when it is realized that modern cameras obviously now have millions of pixels which effectively break down into thousands and hundreds of thousands of patches if one views 'patches' in the roughly 10 by 10 pixel sense.

This line of discussion brings us to the following point: The path and curvature properties of spectricity vectors can, with proper scrutiny and attention to details, be informationally complete descriptors for object morphology. To illustrate the point, the following is method based on this technology for obtaining surface structure of objects:

First using a configuration of the type described in this disclosure, a light source—camera pairing is used to capture images;

then a programmed device or hardware logic:

obtains the spectricity vectors of an object from some fixed viewpoint from these images, calculates the curvatures and paths of those N-D spectricity vectors as a function of the 2 dimensions of the camera's pixels, then maps those resulting paths/curves in N-D space to surface normal estimates of objects.

The surface normal estimates provide a feature characterizing an object's surface, which may be combined with other features for object recognition. This can be leveraged in 2D and 3D object recognition methodologies as another identifying feature, such as in the Bag of Features based approaches referenced below.

This method is applicable for objects that have 'modest' and demonstrably semi-uniform spectral properties across its surface. This characterization of object surface is useful for a variety of applications including, for example, object recognition purposes among others. Aspects of these path/curvature properties will be seen in subsequent disclosure sections, starting with the next section on Spatio-Spectricity Produce Recognition.

Spatio-Spectricity Object Recognition

In U.S. Pat. No. 6,363,366, incorporated herein by reference, entitled "Produce Identification and Pricing System for Check-outs," inventor David L. Henty describes a system which posits that many types of produce can be distinguished based on unique spectral signatures.

This task of distinguishing produce can be augmented by employing methods of this disclosure to extract additional distinguishing characteristics and integrate them tightly with feature vector techniques used in 2D image and 3D object recognition. One advance, for example, is the use of the above described technique to characterize an object's surface from spectral image data, and use a combination of surface features and spectral signature to discriminate and/or identify objects.

Henty's disclosure did not address a number of challenges associated with identifying produce that are yet to be adequately addressed. While one would hope that one specific type and ripeness of banana has a measurably unique 'spectral signature' all to itself, much as a stable formula for a specific dried house paint might have, the reality is that even just on the surface of a single banana, measured in a laboratory/darkroom setting, one finds an extraordinary breadth of not just 'spread' in those signatures but also complicated N-dimensional structure. The next day the same banana, still in the laboratory, moves on to new though certainly highly related structure in signature distributions over its surface. Add now the banana in the bunch right next to it, and several more, over several days, and both the global spreads as well as the specific N-dimensional structures dictate that more sophisticated feature vector extraction is needed to enable classification of such objects.

The techniques described in this document may be leveraged to derive feature vectors from spectricity vectors, in combination with other image features used for 2D image and 3D object recognition.

In one class of classifier technology, our classifier methods uses the principal components of the error ellipsoids of these spreads to formulate a spectral image based feature vector for discriminating produce.

To provide a more powerful discriminator, our classifier embodiments invoke a higher level of discriminant blending which—as with RGB chromaticity long before it—places higher dimensional spectricity coordinates into two dimensional SIFT/SURF/edge discriminant image recognition disciplines. As one example, the two dimensional curve and path behaviors in N-D spectral space that are native to singular instances of a given fruit or vegetable are the characteristic structures that are submitted to late-stage discriminant routines.

We describe these techniques further below and in related disclosures in process.

Omnidirectional Lighting (Diffuse or Directional LED Configurations)

For must applications, it is desired to create uniform lighting across the field of view. For example, in implementations used to experiment with various LED configurations, we have sought to configure the LED light sources to provide nearly uniform lighting across a typical sheet (8.5× 11 inches). To do so, we configure LEDs to provide diffuse lighting. As described herein, while suitable for some applications, the light field may not be sufficiently uniform for others. In that case, the various techniques describe in this disclosure for correcting for this effect may be employed.

For some applications, additional shape and structural characteristics of objects can be extracted from images of them by pulsing with directional and non-directional light sources. These variations in light sources may be used to more accurately reveal object edges and redress shadows.

User Interface

The technologies of this disclosure can be used to development useful user interfaces that enable users to visualize and discriminate characteristics of objects captured by a camera. In one arrangement, the user interface is implemented in a programmable computing device with a cursor control and display. The display depicts images of objects, such as produce, captured using the above techniques for deriving spectricity vectors. 2D color images of the N-D spectricity images are generated by mapping N-D spectricity vectors to a 2D color image space. Then, within this display, the user can select pixels within an object of interest. In response, the computing device calculates a distance metric and then determines from the N-D dimensional spectricity data of that pixel and all other pixels, which pixels fall within a threshold distance of the selected pixels' spectricity vector. A new image is then generated highlighting pixels in a visibly distinguishable color that fall within the distance metric. One such distance metric for N-Dimensional vector space is a Euclidian distance, but there are many other distance metrics that may be substituted for it.

This approach can be further extended to create augmented reality (AR) type user interfaces superimposed on video captured of objects. AR applications process a video feed, recognize objects within a scene and overlay graphical UI elements over the video feed as it is displayed on the user's device. The above UI paradigm, extended to the AR context, and with feature recognition automated, provides a foundation for a variety of AR type UI features. These UI features take advantage of the discriminating and identifying power of N-Dimensional spectral content with the ability to map graphical elements specifically to color image pixels in the 2D display. Thus, as the user views objects in a scene, objects identified or distinguished by their N-D spectral vectors have their pixels highlighted or otherwise augmented with graphic overlays mapped to screen locations.

Classifiers

The process of constructing a classifier involves selection of features that most effectively discriminates among the class of objects sought to be classified. There are a variety of ways to select features, including manual and empirical based techniques, machine learning methods that utilize supervised or unsupervised learning, and combinations of these approaches. See, for example, our patent application on machine learning techniques: 61/880,798, entitled Learning Systems and Methods, which is hereby incorporated by reference.

In some spectral imaging applications, principal component analysis has been employed to reduce the feature space and determine features, e.g., spectral bands used to discriminate objects. In one application, for example, PCA was used to determine spectral bands for discriminating grapevine elements. See: Fernández, R.; Montes, H.; Salinas, C.; Sarria, J.; Armada, M. Combination of RGB and Multispectral Imagery for Discrimination of Cabernet Sauvignon Grapevine Elements. Sensors 2013, 13, 7838-7859.

Extensions to Hyper-Ellipsoid Regions within Multi-Dimensional Space for Classification As noted above, spectral image data may be mapped into feature vector space defined in terms of a hyper-ellipsoid region in multi-dimensional spectral space where the distinguishing spectral characteristics of an object maps into. One method based on this concept is as follows:

Take an object that one seeks to classify; select N patches of spectral image of that object (e.g., N 11 by 11 pixel patches), fit a hyper-ellipsoid around the region of those patches in N-D spectricity space, expand that region to encompass patches while avoiding overlap with regions for distinct objects.

Various feature quantization and binning strategies may be used to map spectral image data into a feature vector used to identify or discriminate it relative to other objects. Two examples of such strategies are Vector Quantizer and t-SNE based methods.

Spectra Identification ("ID") Imaging Modalities

This document describes a class of embodiments of multispectral imaging technology that can be used in a variety of applications, leveraging machine vision and/or machine learning, as appropriate. By exploiting the spectral dimension, this class of technology provides improved performance in such applications.

One imaging modality is the use of multiple LEDs of varying spectral characteristics for multiple exposures of the target of interest. These multiple LEDs can also be optionally augmented by multiple filters of different spectral characteristics (for example, the traditional RGB bayer filter pattern). The multiple exposures, including optional exposures of the ambient environment with no LED, can be combined mathematically to yield a spectricity image that is analogous to the concept of two-dimensional chromaticity.

There are several alternative imaging modalities that may be preferable for some applications. These include devices employing alternative ways to gather spectral images. One alternative is to use a hyperspectral imaging camera. One type of camera offered by Specim, of Oulu Finland, employs an objective lens in which light is first focused onto a narrow slit and then collimated through a dispersive element. This dispersive element has the effect of splitting the light into a series of narrow spectral bands that are then focused onto an area-array detector. In this way, the spectral properties of the single line of light at narrow, contiguous bands are captured. Since the cameras image single lines of light at a time, they must be operated in a push-broom or line scan fashion in which either the object to be measured is moving across the field of view of the camera, or the camera is moved across the field of view of the object. In this manner, a hyperspectral cube can be created that represents a stack of 2-D images, each of which contains specific information about individual frequency bands.

Advances have been made in replacing traditional optics of this approach with on-chip optics and a tunable microelectromechanical system. In particular, IMEC of Lueven, Belgium has developed sensors based on this type of approach. In one spectral imager design, the narrow slit and collimator become optional and the dispersive elements and focusing lens are replaced by an optical fixed wedge structure that is post-processed onto the imager sensor. In another design, the slit and collimator are also replaced with a tunable micro-electromechanical system (MEMS), such as a MEMS implementation of a Fabry-Perot Tunable Optical Filter (TOF). Other types of MEMS based TOFs include, for example, Mach-Zehnder (MZ) filters, and Grating-based filters. When a TOF is used in conjunction with an objective lens, the other elements can be replaced, resulting in a faster, more compact, frame-based hyperspectral camera. For instance, such devices can operate at approximately 10 k lines/s compared with the 0.2 k to 1 k lines/s with traditional optics approaches. The line scan hyperspectral imager from IMEC, for example, scans 100 spectral bands in the 600-1000 nm wavelength range.

TOFs may be configured on an array of pixel elements of an image sensor (e.g., CCD or CMOS) such that they provide an optical band pass filter corresponding to a group of pixel elements. For example, the TOF may be implemented as a stepped wedge positioned across groups of pixel elements.

Another complementary optical element for a portion of the image sensor is a prism for sub-dividing light at different wavelengths to corresponding pixel elements. A prism is particularly useful for splitting incoming IR into an IR wavelength per pixel element on the sensor. In one configuration, for example, a prism is positioned over a rectangular slice of a sensor surface adjacent the TOF elements. This enables the corresponding pixel elements to each capture a corresponding wavelength within the IR range. This type of IR sampling has the advantage that it allows the sensor to get detailed IR sampling per wavelength. Various types of plastics are transparent to IR. Thus, in the retail setting, the IR portion of the sensor can be used to sample characteristics of an item through the plastic packaging or wrapping, such as produce items or meats. For more on use of optical techniques for imaging through plastic and other types of materials transparent to IR, please see 20130329006, which is incorporated by reference herein and provides imaging techniques useful and compatible with those in this disclosure.

The above line scan approach can be employed along with additional image capture elements to capture spectral images in 2 spatial dimensions. For example, in one embodiment, the line scan imager is combined with scanning mirrors to capture full images. In other embodiments, it is combined with strobed or sequenced bandwidth controlled illumination.

Another alternative is to employ Transverse Field Detector (TFD) sensors, with tunable spectral response to provide spectral images. This type of image sensor is described in "The Transverse Field Detector: A Novel Color Sensitive CMOS Device", Zaraga, IEEE Electron Device Letters 29, 1306-1308 (2008), "Design and Realization of a Novel Pixel Sensor for Color Imaging Applications in CMOS 90 NM Technology", Langfelder, Electronics and Information Department, Politecnico di Milano, via Ponzio 34/5 20133, Milano, Italy, 143-146 (2010), and U.S. Patent Publication No. 2010/0044822, the contents of which are incorporated herein by reference. These documents describe a TFD which has a tunable spectral responsivity that can be adjusted by application of bias voltages to control electrodes. In a three channel TFD, each pixel outputs signals for a red-like channel, a green-like channel, and a blue-like channel. Symmetric biasing is applied, such that related pairs of control electrodes each receive the same bias voltages.

Pixel measurements can also be obtained for additional or other spectral bands. A TFD with more than three channels can be provided by applying an asymmetric biasing to a symmetric TFD pixel and increasing the number of spectral channels in the same pixel area. By applying asymmetric biasing, each of five electrodes of the TFD pixel could receive a different bias voltage, thereby providing for five channels that can each be tuned to different spectral sensitivities.

In some of these image sensors, the spectral responsivity is tunable globally, meaning that all pixels in the image sensor are tuned globally to the same spectral responsivity.

In some others of these image sensors, the spectral responsivity is tunable on a pixel by pixel basis or a region-by-region basis. Bias voltages are applied in a grid-like spatial mask, such that the spectral responsivity of each pixel is tunable individually of other pixels in the image sensor, or such that the spectral responsivity of each region comprising multiple pixels is tunable individually of other regions in the image sensor.

Another alternative is an image sensor preceded by a Color Filter Array (CFA) with a tunable spectral response. A CFA may be used with a sensor having a constant spectral response, or in combination with one having a tunable spectral response, such as a TFD sensor. One example of a tunable color filter array described in U.S. Pat. No. 6,466,961 by Miller, "Methods for Adaptive Spectral, Spatial and Temporal Sensing for Imaging Applications", the content of which is incorporated herein by reference. This document describes an imaging assembly comprising a color filter array which precedes an image sensor whose spectral responsivity is constant, but in which the color filter array itself has a tunable spectral responsivity that can be adjusted by application of bias voltages to control electrodes. Each array element thus filters light incident on corresponding pixels of the image sensor, and the image sensor thereafter outputs signals from which a red-like channel, a green-like channel, and a blue-like channel, can all be derived for each pixel. In the case of a color filter array with temporal sensing, the channels for each pixel may be output sequentially, one after the other. In the case of a color filter array with spatial sensing, the channels for each pixel may be output simultaneously or nearly so, although demosaicing might be required depending on the geometry of the color filter array.

A spatial mosaic can be constructed using tunable color filters on top of individual imaging sensors. A Bayer-type mosaic provides color filters tuned to provide three channels distributed spatially. The number of channels can be increased beyond three by tuning color filters to provide four, five or more channels distributed spatially. There is a trade-off between spectral resolution, which is determined by the number of channels, and spatial resolution. However, by increasing the number of pixels of an image sensor, the visual effect of loss in spatial resolution can be minimized. An increased complexity of the spatial mosaic typically requires more complex demosaicing procedures as well as larger spatial filters for demosaicing.

In some of these color filter arrays, the spectral response is tunable globally, resulting in a situation where corresponding channels for all pixels in the image sensor are tuned globally to the same spectral responsivity.

In some others of these color filter arrays, the spectral responsivity is tunable on a pixel by pixel basis or a region-by-region basis. Bias voltages are applied in a grid-like spatial mask, such that the spectral responsivity for each pixel is tunable individually of other pixels, or such that the spectral responsivity for each region comprising multiple pixels is tunable individually of other regions.

Figure 63:
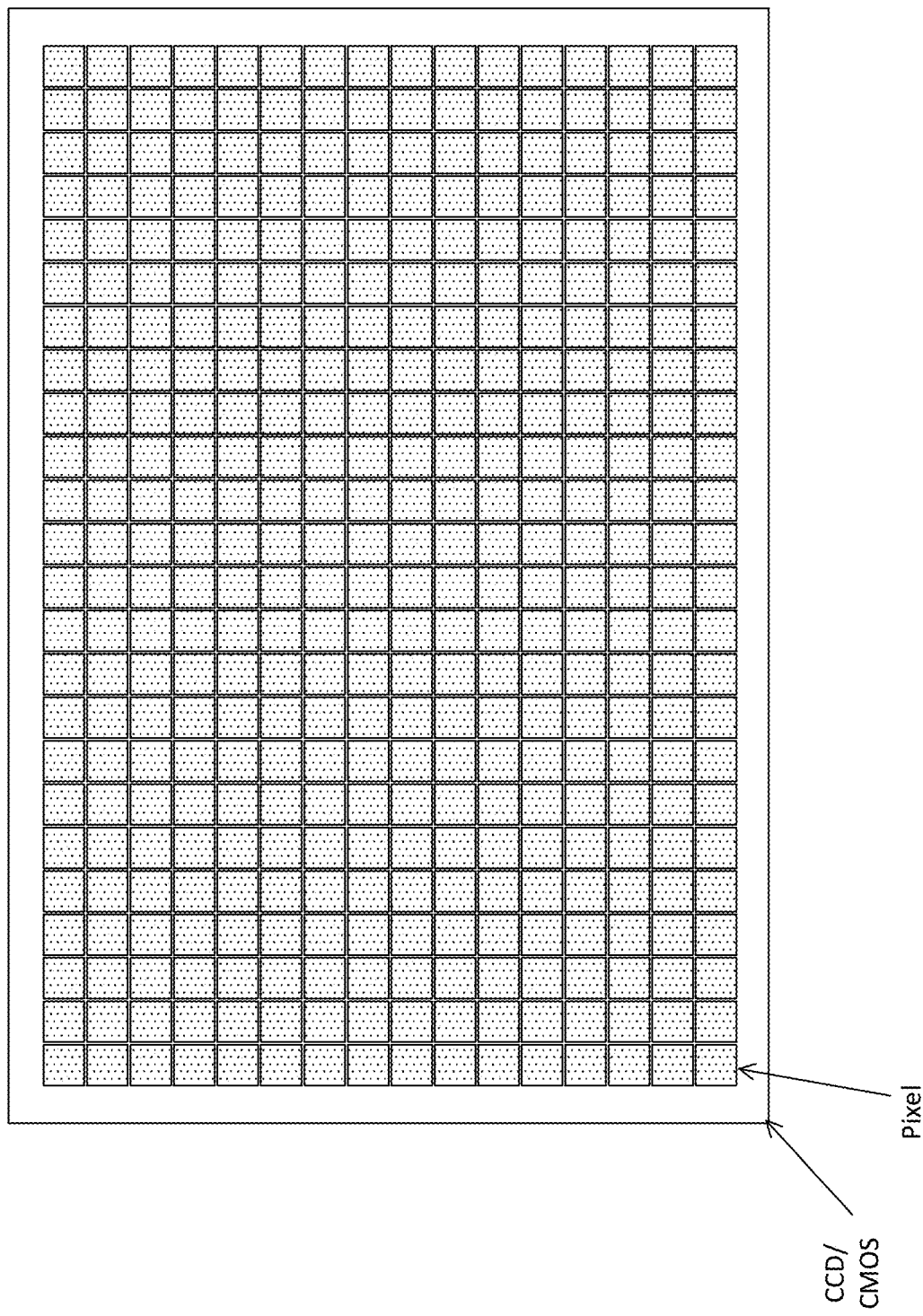
FIG. 63 is a diagram illustrating an image sensor comprising an array of pixel elements.
Figure 64:
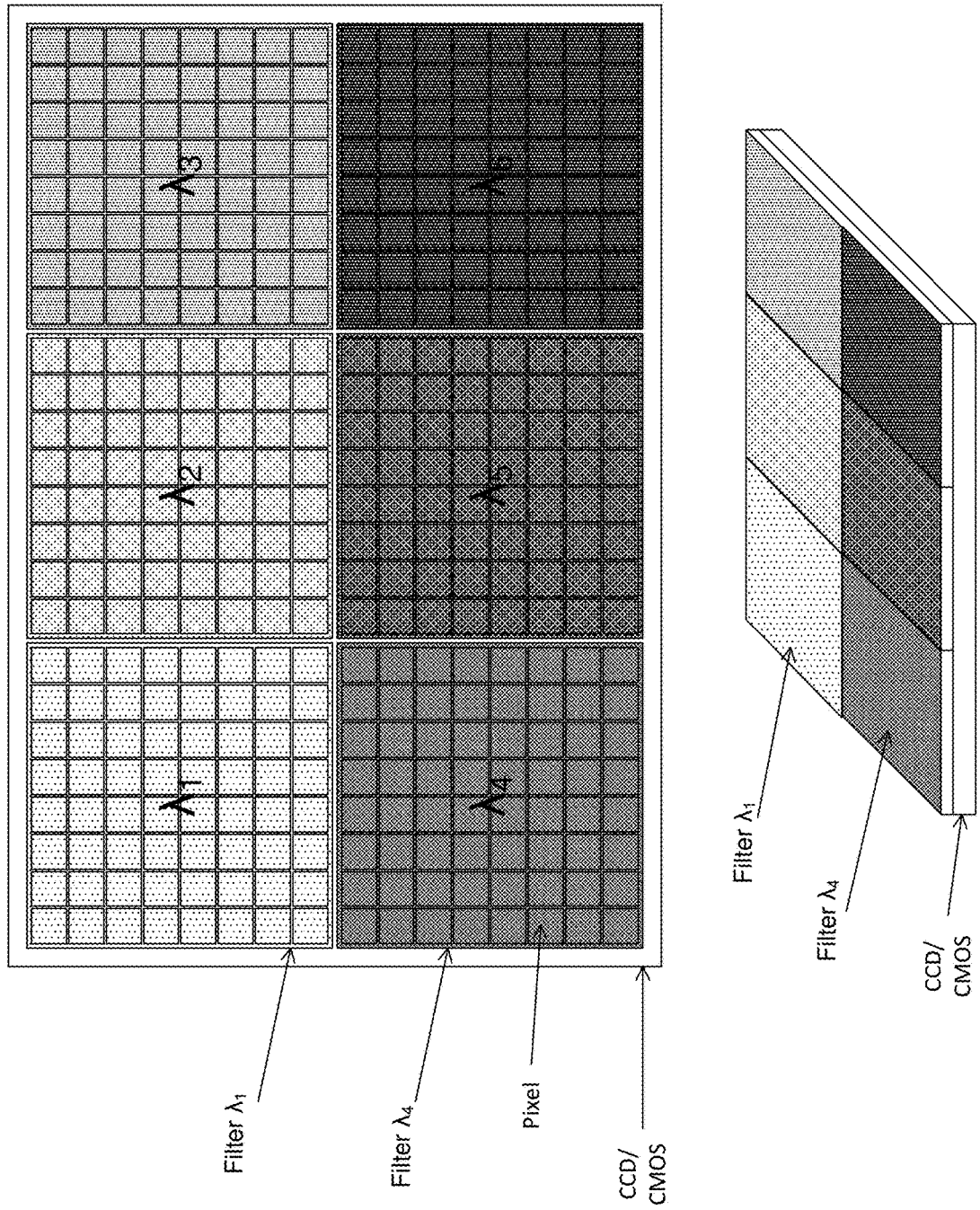
FIG. 64 is a diagram illustrating top and perspective views of an image sensor with optical band pass filters, each for a band of wavelengths $\lambda_n$ (n being a number representing a band of wavelengths), arranged on an array of pixel elements.

FIGS. 63-64 illustrate some example embodiments of these types of multi-spectral image sensors. To provide a baseline from which additional embodiments are constructed, FIG. 63 is a diagram illustrating an image sensor comprising an array of pixel elements.

FIG. 64 is a diagram illustrating top and perspective views of an image sensor with optical band pass filters, each for a band of wavelengths $\lambda_n$ (n being a number representing a band of wavelengths), arranged on an array of pixel elements. This is just one example of a spatial configuration of optical band pass filters to pixel elements on the sensor, and spatial configuration may vary. One reason for varying the configuration is to complement additional optical elements, such as lens, mirrors and prisms, light source position, type and strobing/sequencing, and object scanning methodologies, to obtain a desired 2 or 3 dimensional spatial array of pixel samples with desired resolution of spectral information per unit area/volume of the field of view.

These approaches may be combined with additional elements to capture spectral channels for each pixel in a 3 dimensional array of pixels (x, y, z coordinate space, adding depth). For example, the 1 spatial dimension (line scan) or 2 spatial dimension imaging modes described above may be combined with a micro-lens for plenoptic vision. This yields additional spectral data by slicing the N-D spectricity vector data at differing depths of field. For applications involving scanning objects with translucent surfaces, this enables the imaging device to capture spectral response at depths below the immediate surface of the object. Many biological objects are somewhat translucent, especially to IR—skin, fruits, vegies, etc., and the spectricity vectors for each pixel captured at varying depths provide additional information to discriminate and identify objects.

In addition to spectral and spatial information, yet another type of information that may be measured is polarization using a polarization image sensor. See, for example, V. Gruev and T. York, "High Resolution CCD Polarization Imaging Sensor," in International Image Sensor Workshop, Sapporo, Japan, 2011; and US Patent Publications 20130293871 and 20070241267, which are hereby incorporated by reference herein. In 20130293871, Gruev stacked the photodiodes for different wavelengths of absorption at different depths for each pixel under the polarization-specific filters. This work by Gruev et al. provides examples of polarization imaging sensors.

Other forms of polarization imaging devices may be constructed using alternative and complementary techniques. One approach is to employ polarizing filters on the light source and camera, with the filters selected sequentially for image capture such that a polarizer at a first direction is selected for the light source, and images captured through a polarizer at the camera at the same direction, plus or minus 45 and 90 degrees. Using this approach, polarization measurements can be made for images captured with several different combinations of light source and camera polarizers.

One motivation for measuring polarization (also referred to as polarimetric information) is to discern additional properties of an object being imaged to identify or classify it. Polarization of light caused by reflection from materials contains information about the surface roughness, geometry, and/or other intrinsic properties of the imaged object. Polarization can be used in ellipsometry to measure material properties and stereochemistry to measure specific rotation. Ellipsometry is an optical technique for investigating the dielectric properties (complex refractive index or dielectric function) of thin films. Ellipsometry can be used to characterize composition, roughness, thickness (depth), crystalline nature, doping concentration, electrical conductivity and other material properties. It is very sensitive to the change in the optical response of incident radiation that interacts with the material being investigated. The measured signal is the change in polarization as the incident radiation (in a known state) interacts with the material structure of interest (reflected, absorbed, scattered, or transmitted).

In stereochemistry, the specific rotation ($[\alpha]$) is an intensive property of a chemical compound, defined as the change in orientation of the plane of linearly polarized light as this light passes through a sample with a path length of 1 decimeter and a sample concentration of 1 gram per 1 milliliter. It is the main property used to quantify the chirality of a molecular species or a mineral. The specific rotation of a pure material is an intrinsic property of that material at a given wavelength and temperature.

In applications for classifying produce, the polarization properties of sugar molecules may be used. All natural plant sugars are achiral—that is they have one particular handedness of molecule (left or right handedness). Thus, these sugars will rotate polarized light. Some other molecules within the fruits and vegetables will also have this attribute. Concentrations and molecule types have different rotation amount and this varies with wavelength too. Reflection of polarized light within the outer layers of a produce item show rotation, and varying rotation with wavelength, the composition and concentrations of chiral molecules in that layer, the total optical path-lengths for each wavelength. This polarimetric information provides clues on ripeness available as different sugars are formed or broken down (various reactions catalyzed by enzymes within the fruit or hydrolized or metabolized by decay/bacteria/etc.).

Another application of polarizers is to be able to enhance image sample capture by separating specular and diffuse light, such as that reflected from a scene or object being imaged. The specular reflection is strongly polarized, whereas diffuse reflection is not. The specular reflection from the surface of a package or wrapping or plastic bag on produce, for example, is reduced by using polarizers and post processing to detect and reduce specular reflection from the sampled image, including spectral image data. This post processed image is then submitted to our classifiers for classification. The polarizers allow specular reflection to be detected by correlating the similarly polarized sampling of light across polarizers within the imaging arrangement. Specular reflection will have common polarization, whereas diffuse light will not. Thus, it can be detected by determining correlation among polarization of pixels.

Plenoptic capability in the camera enables the sampling and post processing from the plenoptic camera to provide image views at different view angles, and thereby obtain pixels sampled from view angles at different angles relative to the Brewster's angle. For each of different view angles, the specular reflection is ascertained by post processing of the polarimetric information associated with pixels using the above described technique of correlating polarimetric information across the pixels. Subsequent diagrams depict examples of sensors with both polarizing and plenoptic capability, enabling capture of pixels that image an object at different view angles and orientation of polarizer.

Another way to reduce specular reflection is to illuminate an object using a light source where the angle of light relative to the image may be changed, enabling capture of different frames or scans with different light angles from the light source to the object. One example is to configure LED light sources in ring or other spatial arrangement in which the light angle to the object is sequenced by selective pulsing of the LEDs.

In these types of arrangements, specular reflection impacts can be reduced on subsequent recognition post processing by selecting pixels for input to the post processing captured under modes, such as plenoptic-enabled varying view angle, or pulsed light at varying angles to the object, where specular reflection is measured to be low via the above correlation based technique.

These techniques for sensing and post-process computational exploiting of polarization information may be used in combination with spectral imaging techniques described above. For example, Guev's high resolution polarization imaging sensor provides specific orientations of polarizers over each pixel. This type of imaging structure can be used in combination with color imaging, and spectral image capture described and referenced in this document. One approach is to illuminate an object with switched polarized light sources (on/off, or polarization angle switch (or circular left/right), colors, etc.), and then obtain the additional dimension of information provided by calculating polarization rotation in the image (by wavelength and amount). This type of imaging assembly and method could, of course, be combined with the low-cost hyper-spectral imager camera using the lithographically produced Fabry-Perot filters, or other means of spectral capture (e.g., TFD, CFA, strobed light sources, etc.).

FIGS. 65-71 illustrate additional embodiments of imaging sensor configurations that have polarizer and/or plenoptic capture capability, which may be used in combination with a variety of the multi-spectral capture techniques described above.

Figure 65:
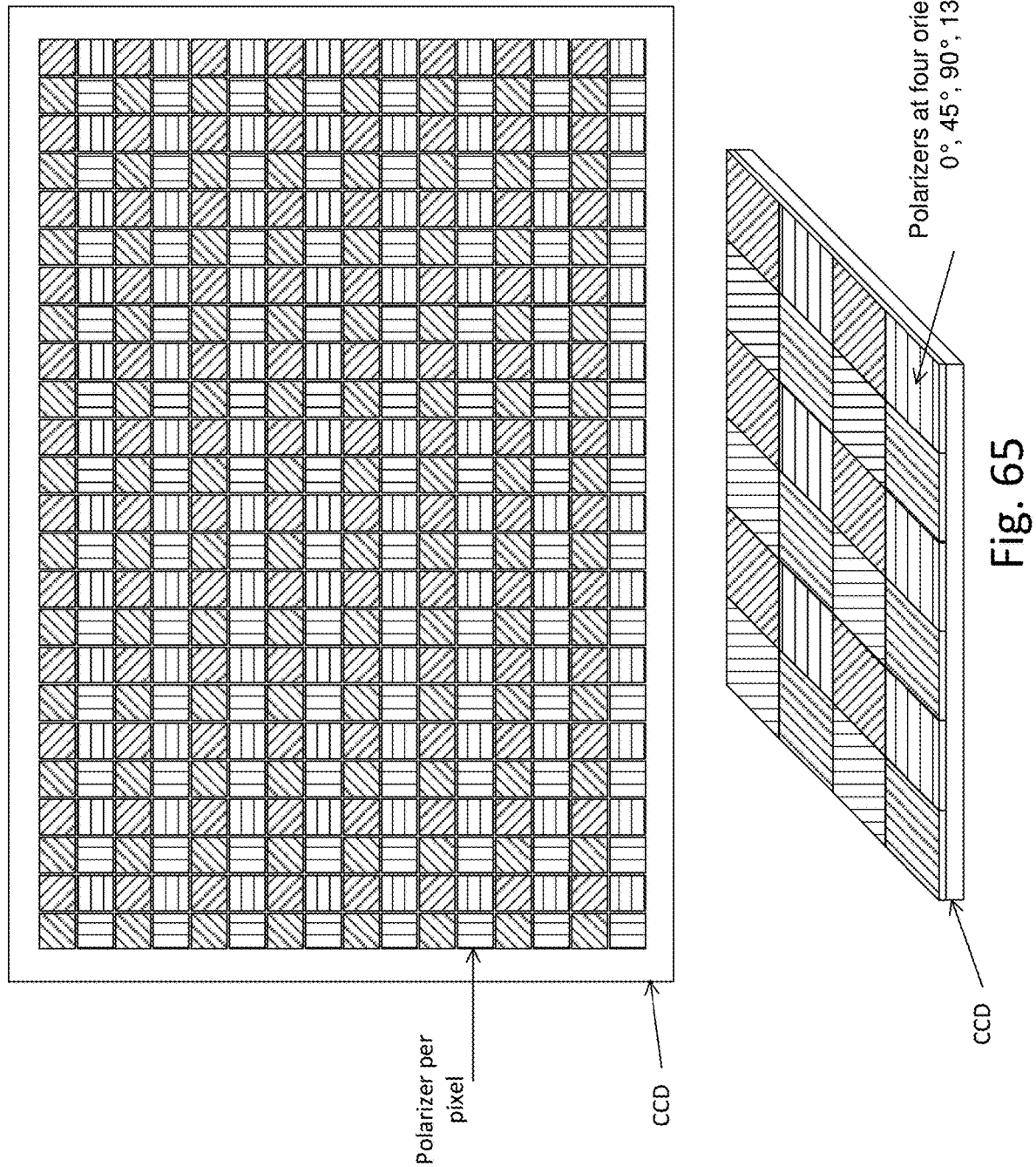
FIG. 65 is a diagram illustrating top and perspective views of an image sensor with a polarizer (e.g., for measuring one of four orientations 0, 45, 90 and 135 degrees) over each pixel element.

FIG. 65 is a diagram illustrating top and perspective views of an image sensor with a polarizer (e.g., for measuring one of four orientations 0, 45, 90 and 135 degrees) over each pixel element. This may be implemented, for example, according to the work of Gruev at al. on polarization sensors cited above.

FIG. 66 is a diagram illustrating top and perspective views of an image sensor with a polarizer per pixel element, and optical band pass filter per 2D block of pixel elements. This is one example configuration of combining polarimetric capture with multispectral capture using optical filters on the sensor. As an alternative to these types of optical filters, other multi-spectral capture may be used instead, or in complementary fashion, such as strobed light sources (e.g., LEDs of different wavelengths), TFD sensors, or other technologies described herein.

Figure 67:
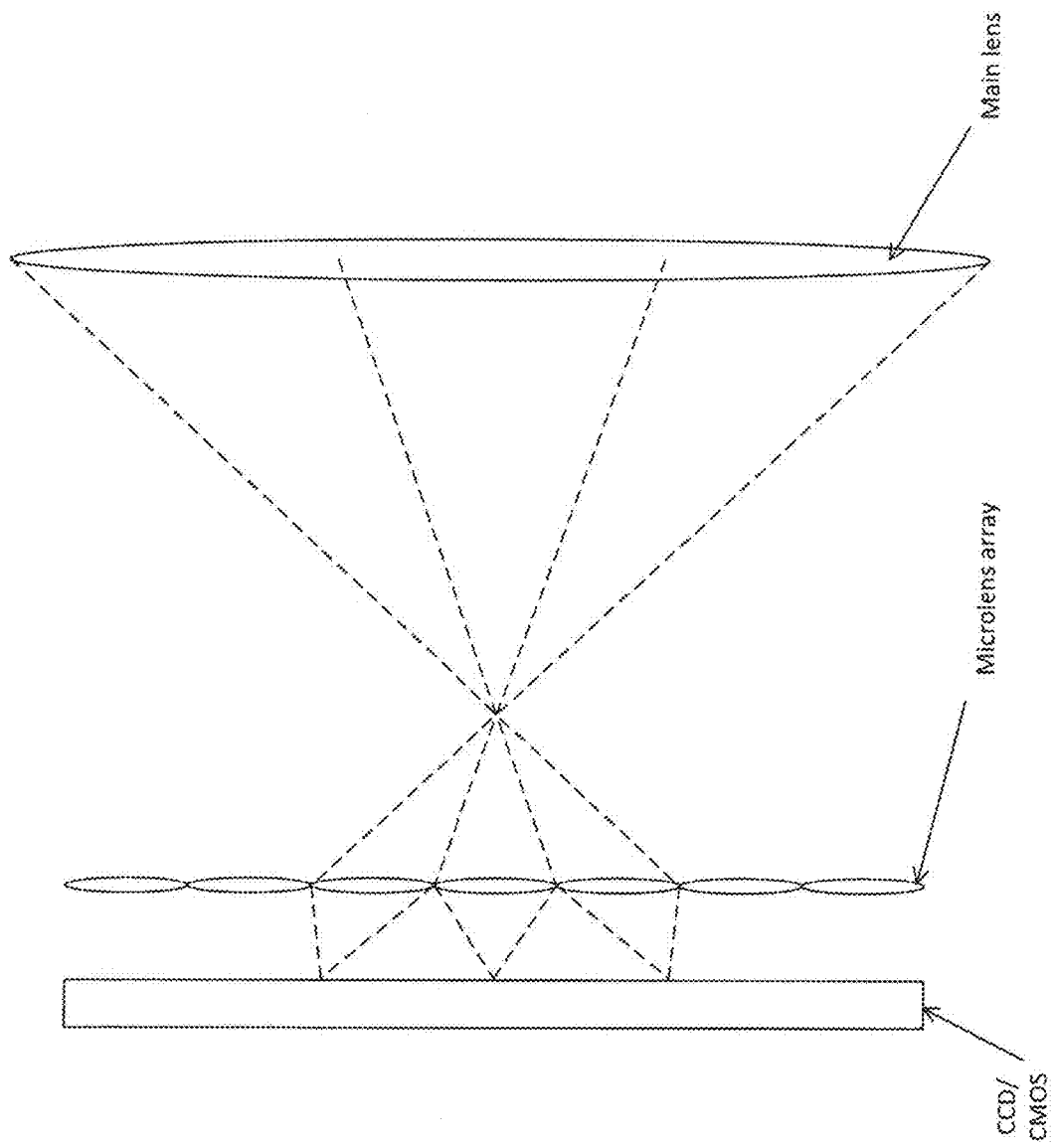
FIG. 67 is a diagram illustrating a side view of an image sensor and lens configuration, together forming a plenoptic camera.

FIG. 67 is a diagram illustrating a side view of an image sensor and lens configuration, together forming a plenoptic camera. As noted in the diagram, this particular positioning of a main lens and microlens array provides a focused plenoptic camera with real image from main lens in front of microlens array. Alternative embodiments have a virtual image from the main lens behind the microlens array, or the microlens array located in the plane of the main image.

The plenoptic capability enables the image sensor configuration to capture multiple views of a scene or object from slightly different view angles. For example, the 2D array of pixel elements under each microlens captures a sub-image of the scene. This provides the capability to capture sub-images of an object being imaged at the pixel elements below each microlens, with each sub-image providing a different spectral and/or polarimetric sampling of the object.

The plenoptic capability also enables the derivation of pixel sample values at different depths (as noted above) using computational photography techniques. This provides the capability to measure spectral and/or polarimetric information at depths above, at and below the surface of an object being imaged (in other words, 3D image capture of spectral and polarimetric information).

FIGS. 68-71 illustrate various options of imaging configurations, and teach many additional variants that can be made by interchanging components.

Figure 68:
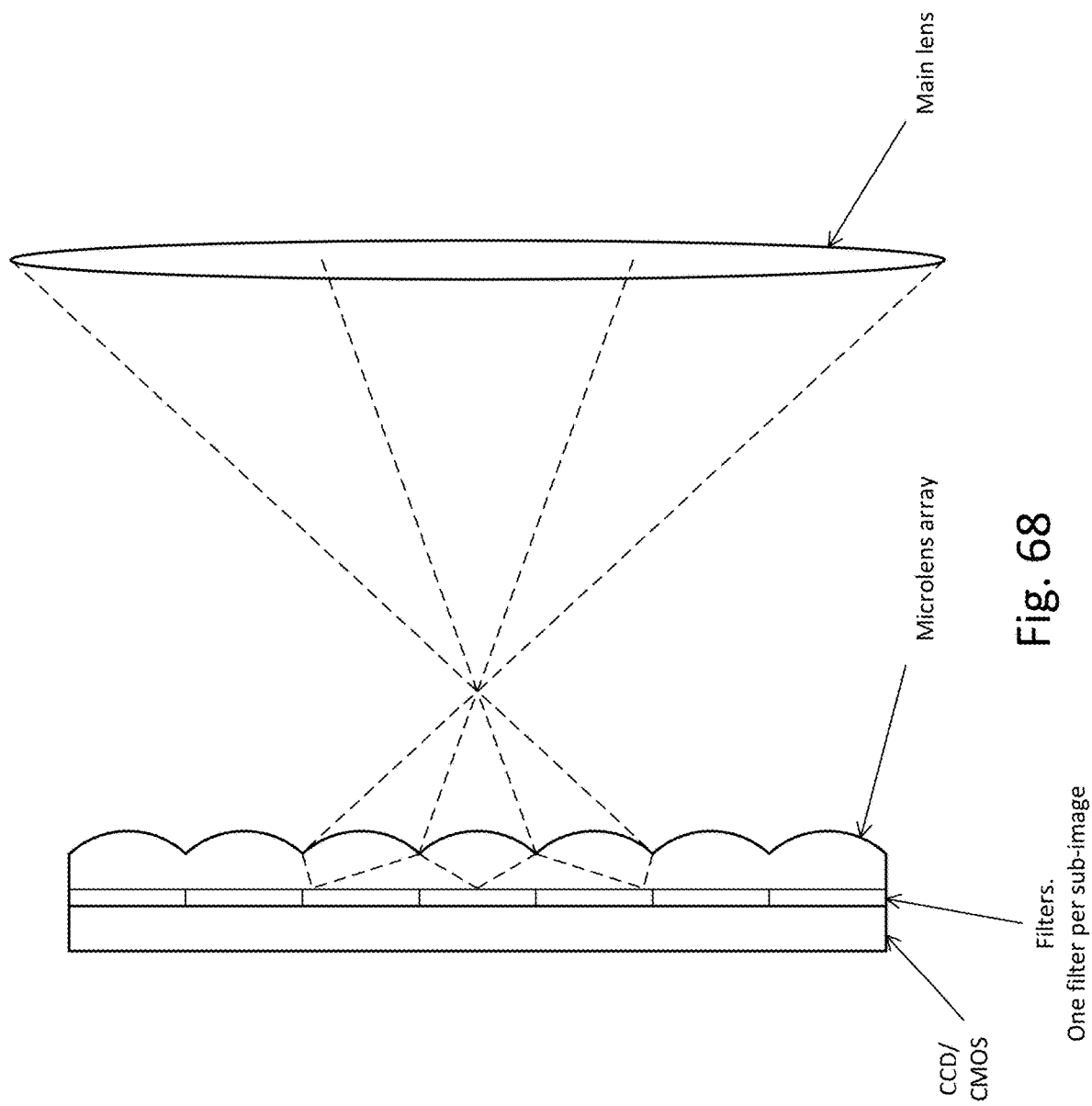
FIG. 68 is a diagram illustrating a side view of an image sensor having optical band pass filters on the sensor, followed by a microlens array, where the filters are positioned to coincide with a corresponding microlens array element such that there is one filter per sub-image obtained through the positioning of a main lens relative to the microlens array as shown.

FIG. 68 is a diagram illustrating a side view of an image sensor having optical band pass filters on the sensor, followed by a microlens array, where the filters are positioned to coincide with a corresponding microlens array element such that there is one filter per sub-image obtained through the positioning of a main lens relative to the microlens array as shown. This is an example where each sub-image provides a different spectral band corresponding to the band of the optical band pass filter coinciding with the microlens above it.

Figure 69:
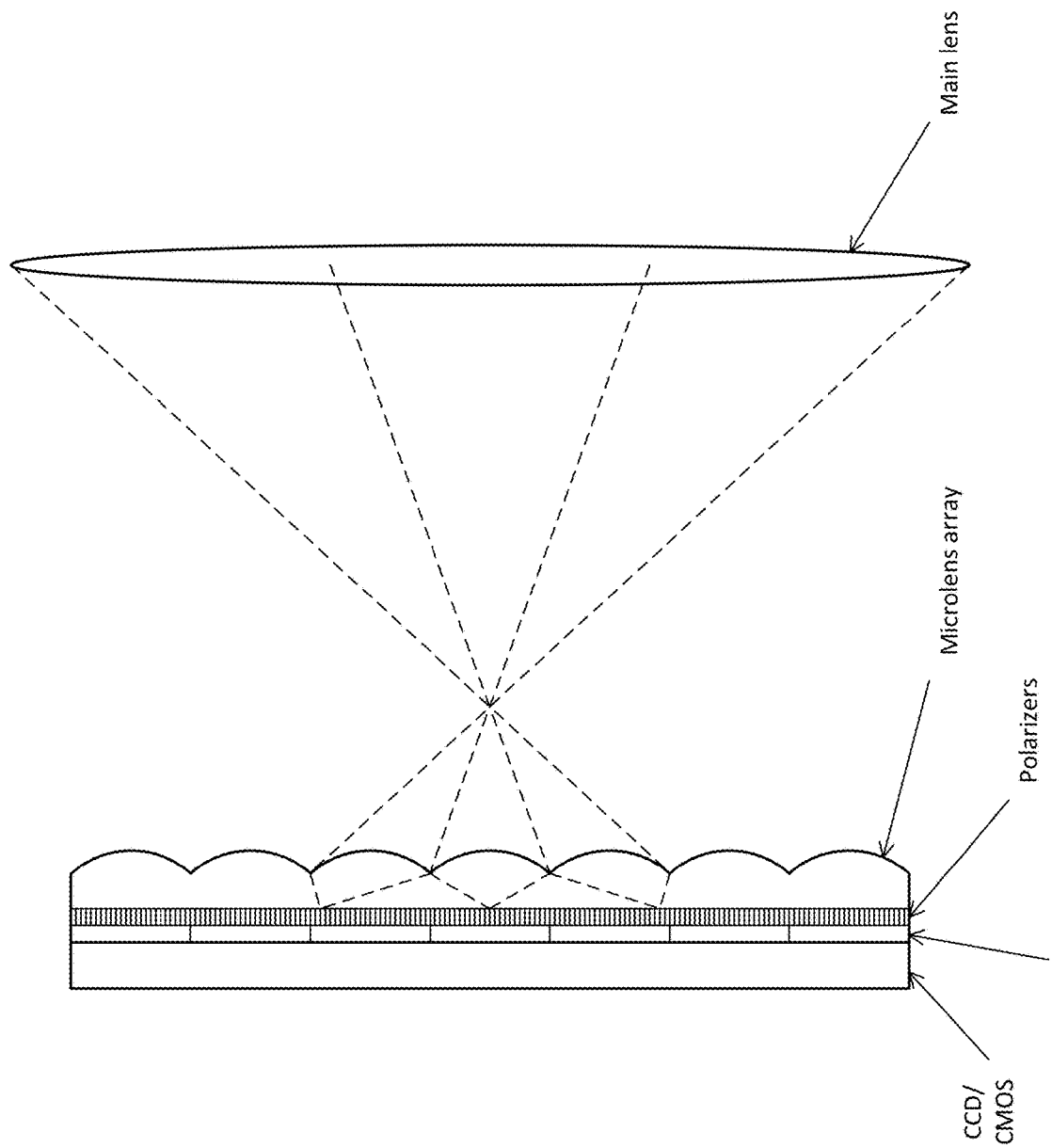
FIG. 69 is a diagram illustrating a side view of an image sensor like the one in FIG. 68, but further adding a layer of polarizers between the optical filter elements and microlens array.

FIG. 69 is a diagram illustrating a side view of an image sensor like the one in FIG. 68, but further adding a layer of polarizers between the optical filter elements and microlens array. This adds polarimetric capture capability to the configuration of FIG. 68. Within each sub-image corresponding to a microlens and filter pair, the polarizers provide polarimetric capture at different orientations, similar to the examples depicted earlier. The orientations of the polarizers can be varied within a sub-image area, or may be the same across each sub-image, yet different from one sub-image to another.

Figure 70:
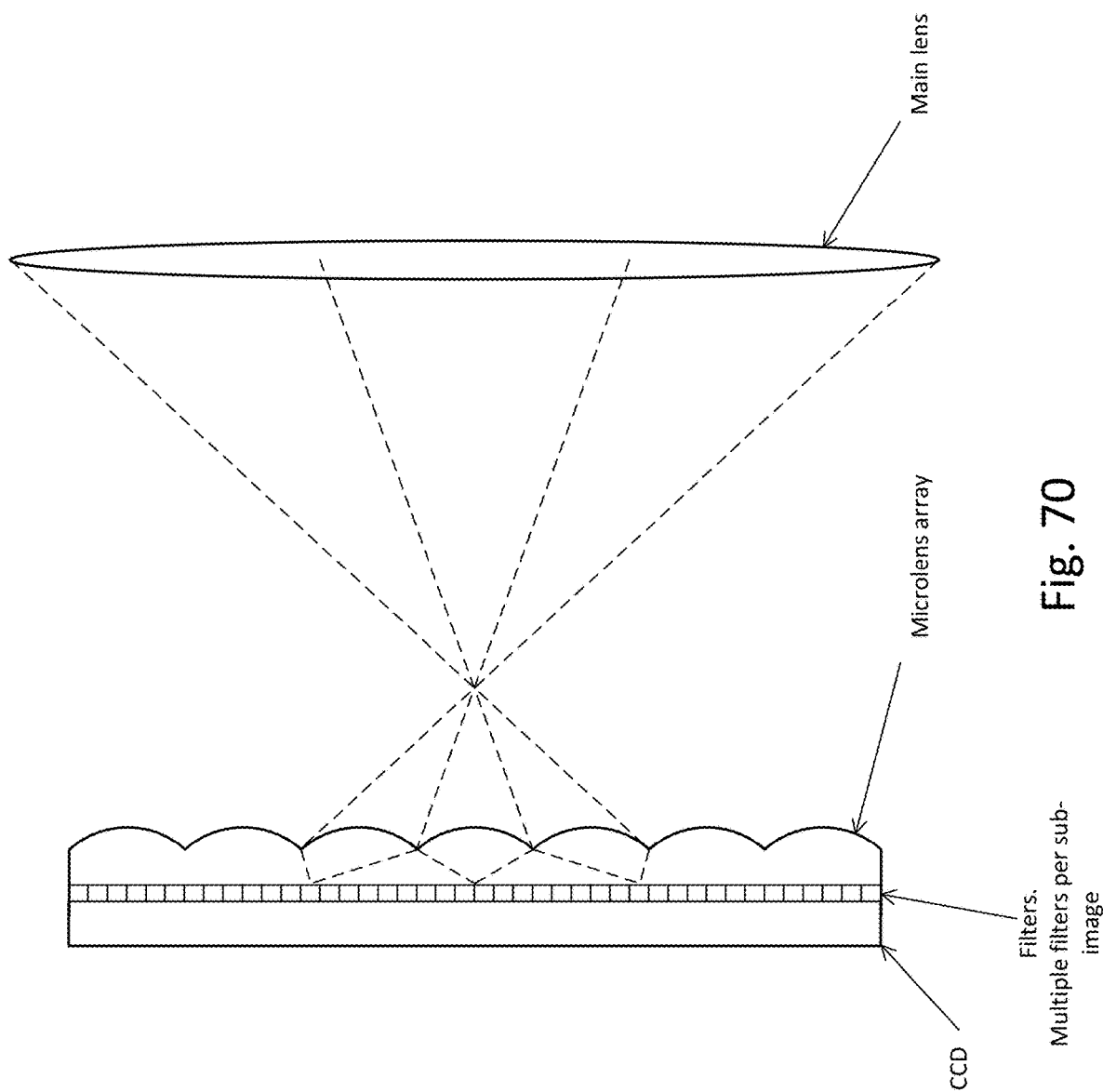
FIG. 70 is a diagram illustrating a side view of an image sensor like the one in FIG. 68, but with the alternative of having multiple optical band pass filters per sub-image.

FIG. 70 is a diagram illustrating a side view of an image sensor like the one in FIG. 68, but with the alternative of having multiple optical band pass filters per sub-image. This configuration provides the capability to capture multiple different spectral bands within each sub-image. Sub-images may be combined to provide multiple spectral bands per common pixel location within each sub-image.

Figure 71:
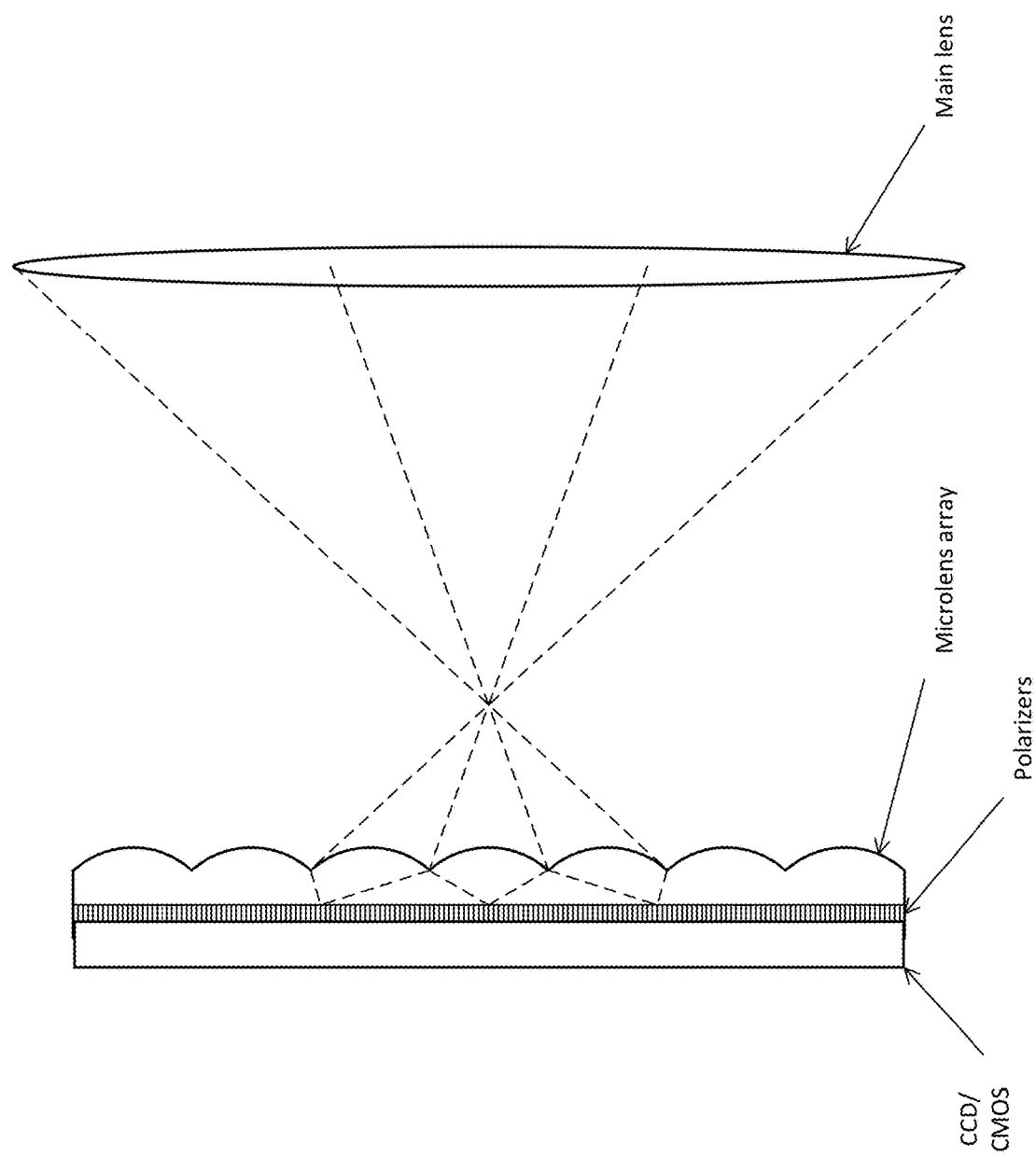
FIG. 71 is a diagram illustrating a side view of an image sensor like the one in FIG. 69, but without the optical band pass filters.

FIG. 71 is a diagram illustrating a side view of an image sensor like the one in FIG. 69, but without the optical band pass filters. The spectral capture may be achieved using technology other than the optical band pass filter technology mentioned, such as TFD or strobing of light sources at different spectral wavelengths.

These various imaging modalities may be implemented in variety of device types. These types include general purpose imaging devices, such as cameras and scanners, where multispectral capture modes are provided among dedicated camera options. These device types also include multifunction devices such as mobile devices and computers with integrated cameras and light sources (e.g., smartphones, tablets, personal computers, etc.). Another device type is a special purpose device, such as barcode scanning equipment, machine vision systems, medical imaging tools, etc.

Tailoring the Classification Methods to the Statistics of Classes

The Spectra identification approach can be used to classify observations of a plurality of classes. Preferred implementations of classification algorithms will in many cases depend upon characteristics of the classes to be identified, as different collections of classes will be more or less amenable to identification using different types of algorithms and techniques.

A main influence on the type of classification algorithms which are most useful is the statistics that surround the different classes to be identified. Here, statistical variation within all the objects of a class is of interest, as well as statistical variation between different observations that may be made of a single sample or individual to be identified. Of course, if the statistical variation is far wider between classes than within classes, the classification task is much easier. However, in many cases, the observed distributions between classes are not trivially separated. Additional statistical issues must then be confronted in the design of a classifier based on limited training data; the well-known tension between under-fitting and over-fitting is at base a statistical problem.

It is useful to construct a simple "taxonomy" of the statistical variation that can be seen within classes. Specific observation and classification algorithms can then be brought to bear on the classification problem based upon the statistics in the classes of interest.

1. Impulsive sources. Some spectral sources are especially well-defined, such as the emission spectrum of sodium. In terms of spectricity, these sources can be best represented as single points within the multidimensional spectricity space. In the case of sodium, there are clear physical explanations that can be identified to explain the specific spectrum.

2. Near-Impulsive sources. Pantone™ ink spot colors are sources that can best be represented as single spectricity "impulses", even though there may be some (relatively limited) variation among samples. Variation among different samples of the same color can be ascribed variously to differences in base ink mixing proportions, age, and fading due to sunlight, etc. Classifier designs can take into account the relative magnitudes of variation about an ideal impulsive characteristic that are due to variation among different individual examples of members of the class versus variation within a single sample being classified.

Classifiers for impulsive and near impulsive sources can be relatively simple, compared with classifiers for the following types of sources.

3. Distributed sources. For some sources, there is significant variation either between different individuals within a class, or within a single representative of the class, or both. An example of this type of source would be apple varietals. Each type of apple (Pink Lady, Pinata, Ambrosia, etc.) can exhibit a range of different colors and, therefore, spectricities. In contrast to the impulsive sources, a distributed source can be represented with a non-impulsive marginal probability distribution in the N-dimensional spectricity space.

Specific classification strategies can be used to deal with difficulties of distributed sources.

4. Sources with memory. Some distributed sources have additional statistical complexity that cannot be captured through a marginal probability representation. This is true for the previous example, that of varieties of apples. In other words, looking at the probability distribution of N-dimensional spectricities of a single pixel of an image of a Pinata apple does not capture the full picture. Put another way, the distribution of the spectricity of one pixel in the image of a Pinata apple is not independent of the spectricities of nearby pixels.

A random process with memory always has less entropy than a memoryless source; a corollary of sorts is that memory should be an exploitable characteristic that can provide identical or improved classification performance over classifiers that do not exploit source memory.

Strategies for Dealing with Distributed Sources.

1. Visualization.

Being able to visualize N-dimensional spectricity distributions of the classes to be identified is invaluable. Of importance here are dimensionality reduction techniques that can preserve enough of the N-dimensional structure in a two or three dimensional representation.

One method that has been found useful is t-Distributed Stochastic Neighbor Embedding (t-SNE).

t-SNE Based Methods t-SNE methods provide an effective tool for visualizing multi-dimensional data sets, such as our N-D vectors in lower dimensions, such as 2D or 3D representations that humans can analyze. For example, such a tool enables us to visualize the extent to which spectral N-D vectors of image patches of different objects (e.g., produce items) map to distinct clusters in a dimension we can visualize (2D or 3D space). This assists in the design of classifiers, for example. The next paragraphs provide an overview, and then we describe further applications of this tool with our technology.

See, L. J. P. van der Maaten and G. E. Hinton. Visualizing Data using t-SNE. Journal of Machine Learning Research 9 (November):2579-2605, 2008). T-SNE represents each object by a point in a two-dimensional scatter plot, and arranges the points in such a way that similar objects are modeled by nearby points and dissimilar objects are modeled by distant points. When t-SNE software constructs a map using t-SNE, it typically provides better results than a map constructed using something like principal components analysis or classical multidimensional scaling, because:

(1) t-SNE mainly focuses on appropriately modeling small pairwise distances, i.e. local structure, in the map, and (2) because t-SNE has a way to correct for the enormous difference in volume of a high-dimensional feature space and a two-dimensional map. As a result of these two characteristics, t-SNE generally produces maps that provide clearer insight into the underlying (cluster) structure of the data than alternative techniques.

In one embodiment, we used t-SNE to map 45 dimensional spectricity vectors into a 3D space for visualization. The approach is:

i. Compute 10 principal components of a spectricity data set for an object ii. Set up the data for the t-SNE software to map the spectricity data into a 3D representation by setting constraints at each end of the principal component axes. For this embodiment, we set these constraints to correspond to an opposing pair of vertices of a dodecahedron in 3D space. There are a total of 20 'sphere constraints' which are artificially placed well outside the data blob zone but exactly on the first 10 principal component axes of the data itself, one each at the two poles of each principal component. The 3D projections of these constraints are initially set to the 20 vertices of the dodecahedron, but then the t-SNE software is free to move them about using its algorithms.

iii. Execute the t-SNE software to map the spectricity data to the 3D space with these constraints. We observed that this approach causes the principal components and associated data samples to move about in the 3D space, yet still provide a 3D visualization of the spectricity vectors.

This technique allows us to visualize 45 dimensional spectricity vectors for different classes of objects to see how the vectors differ for different classes. This provides clues for classifier design, as well as a means for users to visualize and discriminate objects based on the shape of the mapped data of an object.

One application of this technology is to use it in the derivation of bins that can be used in recognition methodologies such as vector quantization as well as Bag of Features, in which feature vectors for spectral data input are mapped to bins. These approaches are described elsewhere in this document, including in the section on vector quantization and in sections relating to Bag of Feature approaches.

Another application is the design of UIs for applications, like smart phone mobile applications that are configured to compare objects and illustrate how similar they are in multi-dimensional space through a 2D or 3D depiction on the display of the mobile device.

2. Classification.

As an example of methods for dealing with classification of distributed spectricity sources a simple example of classification of apple varieties is described.

Samples of 20 apples each of three different varieties of apples (Pink Lady, Pinata, Ambrosia) were used. A database was constructed with each apple represented by four images of different areas of the apple. Images were taken at a fixed distance, with each apple placed on a board with a 1.5 inch circular hole, and the camera imaging the apple from below through the hole. Each image consisted of 16 exposures, including 15 different LED exposures and a reference ambient exposure. Each image was segmented to remove non-apple areas of the images. A color camera was used, and spectricity values were calculated for each pixel in the apple-segmented image.

Experiments were run by randomly assigning 10 apples from each class to a training set, and using the remaining apples as a test set. This process was repeated many times to arrive at average expected performance results.

a. Vector Quantization Based Methods.

This section immediately addresses the task of using spectral measurements from a small number of image bands (typically between 5 and 15) to classify (identify) produce items. It is more generally applicable to a wider array of problems, including different 2D image recognition and 3D object recognition applications. A smaller or much larger number of spectral bands are easily accommodated. The techniques can also be adapted to a variety of other continuous or many-valued characteristics of produce that may be measured. Finally, these ideas may be used to classify items outside of the field of produce.

Vector Quantization

Because we are dealing with multi-dimensional spectral measurements, the vector quantization approach will be used. Vector quantization is a well-studied technique for lossy data compression, and it has also been proposed for use in classification applications.

See, for example:

Pamela C. Cosman, Robert M. Gray, Richard A. Olshen, Vector quantization: clustering and classification trees, Journal of Applied Statistics, Vol. 21, Iss. 1-2, 1994

Supervised learning systems, based on vector quantization systems, are sometimes referred to as Learning Vector Quantization (LVQ) systems, and one can learn more about such systems by reviewing literature on LVQ.

Another example of a VQ based learning system is referred to as Classified Vector Quantization, and such an approach is described in Bailing Zhang, Classified Vector Quantisation and population decoding for pattern recognition, International Journal of Artificial Intelligence and Soft Computing, Volume 1 Issue 2/3/4, July 2009, Pages 238-258.

The above are but a few examples of background and supporting literature on the design of VQ based systems that one may refer to in implementing our methods or variants of them.

An n-dimensional vector quantizer (VQ) maps n-dimensional sample vectors to quantized codebook vectors. A VQ consists of a codebook $C=(c_1, c_2, \ldots cM)$ of M n-dimensional vectors, and a partition P on the n-dimensional space so that each codebook vector has a corresponding cell of P. A source vector v is encoded by representing it with the index of the cell of P which contains v. If a VQ codebook contains $2^{\wedge}m$ codebook vectors, then it can quantize a source of n-dimensional vectors at a rate of m/n bits per sample. A VQ is designed (trained) using a training set of n-dimensional vectors taken from a distribution which approximates the source.

Usually, the squared error metric is used, so that the codebook vector chosen to represent a source vector is the codebook vector with smallest Euclidean distance to the source vector. For classification purposes, squared error may be appropriate, or certain other measures may be used. There are alternatives for an appropriate measure of distance or similarity for training and classification. Techniques have been developed which adapt a parameterized distance measure in the course of training the system, see e.g., P. Schneider, B. Hammer, and M. Biehl. Adaptive Relevance Matrices in Learning Vector Quantization, Neural Computation 21: 3532-3561, 2009, which is hereby incorporated by reference herein. For further information, also see the references cited therein.

Design and encoding complexity of general VQs increase quickly with increasing dimension and/or quantization rate. The limiting performance of a set of VQs with increasing dimension satisfies the rate/distortion bound of a given source.

Tree-Structured Vector Quantizers (TSVQ)

TSVQs are a simplified class of VQs that provide suboptimal performance, but have a lower complexity of training and encoding. A TSVQ consists of a set of simple VQs of the same dimension which satisfy a tree structure. In the simplest case, that of a binary TSVQ, each of the component VQs has a codebook with two code vectors. The corresponding tree structure is a binary tree, with each component VQ occupying a single node of the binary tree. Source vectors are quantized by first quantizing them with the root component VQ. Then, based on which code vector best represents the source vector, the source is quantized using the corresponding first level descendent VQ. This process is repeated until the source is quantized using a leaf node VQ. For a balanced binary tree of m levels, the quantized version of a source vector is given by the binary vector specifying the path from the root of the tree to the final quantized codebook value. The resulting compression rate is m/n bits pre sample.

Training such a TSVQ is a recursive process. First, the root node VQ is trained. The result is a VQ that partitions the training set of vectors into two training subsets, one for each codebook value. Each of these training subsets is then used to train the corresponding component VQ in the tree structure. At the end of this process, there are four training subsets. This process is repeated, for a balanced tree TSVQ, until the desired number of levels in the tree have been constructed.

Classification Using TSVQs

If the spectricity values in the training set are quantized using a vector quantizer, each class of items (e.g., apples in our example) will impose a corresponding probability distribution (probability mass function (pmf)) across the voronoi regions of the quantizer, with a probability mass associated with each voronoi region. This distribution can be characterized and used to help classify the test samples, based upon the quantized values of the pixel spectricities in the test samples. The VQ pmf is used, rather than the raw N-dimensional spectricity pmf of the training set because each component of a spectricity vector was represented with 16 bits of precision, and the training pmfs of each apple type would severely overfit the true spectricity pmf of each class.

VQs in general can be used for classification by associating a class with each codebook vector. As long as the members of classes tend to be close to one another for some convenient distance measure, these members will tend quantize to the same codebook vectors. The simplicity advantages of TSVQ can be used to improve the simplicity of the classification task, as well as possibly providing some additional flexibility; the techniques to be described will also apply to other forms of VQs.

Training a TSVQ for classification is an exercise in unsupervised learning. We can augment the normal TSVQ training process by associating a class tag with each training vector in the training set. So, for example, we could have training data for 20 varieties of produce (jalapeno, cucumber, banana, etc). For each variety we obtain a quantity of 10 items. Then, for each of the 200 items, we take ten multi-spectral images, each with 8 spectral bands. For each multispectral image, we apply a simple averaging filter and then randomly select 10 8-dimensional pixel vectors. In total there are 20 varieties×10 items×10 images×10 vectors=20000 vectors, each with a tag identifying the corresponding produce variety.

The TSVQ is trained in the normal way, keeping the tag class associations in the construction of each training subset. In addition, we associate a probability distribution, called the estimated distribution, with each codebook vector of each component VQ (at all levels of the tree). This distribution represents the distribution of class tags within the sub-training set of training vectors that are quantized to that codebook vector. The TSVQ is designed in an unbalanced tree such that, at the leaf code vectors, each corresponding training subset has no more than a given number of training vectors.

In the simplest case, we take a single pixel from a single multispectral image of an unknown produce item. This vector is quantized, one bit at a time, by stepping through each level of the TSVQ. At each level, the corresponding estimated distribution is used to estimate the probability of our item being a radish. Hopefully, with each succeeding level, this estimated distribution will sharpen, so that we can gain certainty. Note that if the TSVQ is designed exhaustively so that each leaf vector is associated with exactly one training vector, the estimated distribution will trivially identify the class of the nearest training vector. The "validity" of the estimated distribution hinges somewhat on the number of training vectors it is based on. A powerful TSVQ classifier will tend to separate distributions several levels above the leaf nodes. FIGS. 61-62 illustrate this with a hypothetical case of just two varieties, apples and bananas, and just two spectral dimensions. The example shown in FIG. 61 shows a strong classifier that separates the classes early in the tree, and FIG. 62 shows a weak classifier.

To classify a single vector, the vector can be quantized to some desired number of levels within the tree, and the resulting estimated distribution used to determine the class estimate. A simple method is to choose the class with the highest probability (equivalently, choose the class that had the most training vectors that quantized to the same code vector). If the training set distribution is a good representation of the "true" class distributions, this method is akin to maximum likelihood estimation of the class.

Multi-Vector Classification

Of course, it is desirable to have more certainty than can be obtained from classifying a single vector (pixel) from a multispectral image of an unknown item. In general, multiple multispectral vectors can be used to classify a single item. The simplest method might be to classify 5 image pixels of the unknown item, and choose the mode as the classification of the item. However, it may be useful to have the class estimate be a function of several estimated distributions, one for each quantized vector. Such an approach would be to treat the five estimated distributions as marginal from an independent joint probability distribution. Combined with knowledge that each pixel observation is from the same (unknown) class, the resulting joint estimated distribution is the product of the five marginal estimated distributions, and choosing the maximum from among these is a reasonable classification choice.

Distributional Approach

As more and more observations are made of an unknown item, we can begin to approximate the distribution of the item's spectricity. Now it makes sense to ask which of the classes has a typical distribution that is closest to the observed distribution of our unknown item. "Typical distribution," here is used in an asymptotic equipartition property sense. One possible approach is to use the Kullback-leibler divergence as a distance measure between the observed distribution and the distributions of the training vectors for each of the classes of produce. If the training set sizes for each class are equal, using the Kullback-Leibler divergence is equivalent to choosing the class with the maximum sum of the logarithms of the estimated distributions.

Example implementations are provided in matlab source code file appendices named ClassifierTSVQ_appendix.txt, basicClassify_appendix.txt, and VQ_appendix.txt. ClassifierTSVQ_appendix.txt includes code methods for training and classifying a classifier. VQ_appendix.txt provides code for building a node of a tree of the VQ based classifier, and it is repeatedly invoked for each node in the tree. basicClassify_appendix.txt includes code for combining output of the classifier using multiplicative probability or Kullback-Leibler approaches. This enables the classifier output for distinct inputs to be combined in a manner that increases the discriminating power of the system. For example, the classifier uses this to combine the classifier output for several N-D spectricity pixel inputs taken from a suspect produce item that we wish to classify. Likewise, each input of the classifier may be a vector combining several vectors into a single input vector. In this case, the classifier output for each such vector, itself a combination of vectors, may be combined using these techniques (multiplicative probability or Kullback-Leibler approaches).

b. Support Vector Machines (SVMs). SVMs are a well-known machine learning technique. For background see: T. Fletcher, Support Vector Machines Explained, University College London, Mar. 1, 2009; C. Burges, A Tutorial on Support Vector Machines for Pattern Recognition, Data Mining and Knowledge Discovery Volume 2 Issue 2, June 1998, Pages 121-167, Kluwer Academic Publishers, which are incorporated by reference herein; and Support Vector Machine (and Statistical Learning Theory) Tutorial by Jason Weston of NEC Labs America. As noted in the latter, SVM software is available from various sources, e.g., LibSVM in C++, SVMLight, as well as machine learning toolboxes that include SVMs: Torch (C++), Spider (MatLab), and Weka (Java), available at www.kernel-machines.org.

SVM is fundamentally a binary classifier. The simplest case of an SVM applied to the apple dataset will handle single 45-dimensional spectricity pixels. Classification among many classes proceeds through a separate "one vs. rest" classifier for each of the classes to be identified, with the class producing the highest output being chosen.

In the simplest case of a linear "kernel", each spectricity vector in the training set constitutes a single point in the training space. The training process is a quadratic optimization problem that chooses the optimum N-dimensional hyperplane to partition the classification choice. Typically at least two design parameters are manually optimized in the process as well. These parameters balance the degree of over/under fitting, and also the relative cost for misclassification vs. hyperplane classification margin distance.

The classification process takes an input spectricity value and determines on which side of the chosen hyperplane the input lies.

For some problems, a linear hyperplane might not do a good job of separating the raw spectricity values by class. In these cases, a nonlinear kernel function can be chosen to see if the results can be improved. The radial basis function (RBF), or Gaussian kernel is one of the most popular choices. When most kernel functions are used, the usual approach is to increase the number of features (45 in this case for the linear kernel) to be equal to the size of the training set. This results in a much slower training process for cases with large training sets.

One possible improvement to lower the complexity of nonlinear kernel SVMs would be to limit the expansion of the number of features to the number of voronoi cells in a VQ trained for the training set distribution. Then the feature corresponding to a certain cell can be calculated as the sum of the features that would be calculated for each training set member that is quantized to that voronoi cell.

A standard means of judging the degree of over/under fitting is to use n-fold cross validation to design classifiers using different training sets. The results can then be analyzed help determine the adequacy of the result.

There are two simple ways to accumulate classification results over multiple spectricity pixels. The simplest is to sum up the "votes" for the class of each pixel over all the pixels in a given unknown object, and choose the winning class. Another option is to use some weighted function of the directed distances of each spectricity pixel from the decision hyperplane.

c. Neural Networks and Associated Learning Methods (e.g., RNN, Refractory neural nets and vision) may also be applied to design an object classifier for spectral vectors and spectral vectors combined with other features, 2D spatial or 3D spatial information associated with spectricity vectors.

For more information on learning methods and classification in spectral imaging, see, e.g., G. Camps-Valls, D. Tuia, L. Bruzzone, and J. A. Benediktsson, Advances in Hyperspectral Image Classification, IEEE Signal Processing Magazine, Volume 31, Number 1, January 2014, pages 45-54, which is hereby incorporated by reference. This article lists the following approaches in the field of hyperspectral image classification, along with citations to publications corresponding to each one: kernel methods and SVMs, sparse multinomial logistic regression, neural networks, Bayesian approaches like relevance vector machines, and Gaussian processes classification. It also lists spatial-spectral approaches, and citations to publications corresponding to them.

Strategies for Dealing with Distributed Sources with Memory.

There are a variety of methods to exploit the inter-pixel dependence to improve classification results. All of these methods are highly sensitive to scale, in the sense that the joint distribution of two pixels in a spectricity image will naturally be a function of the distance between those points on the object of interest.

Spectricity Texture

We experimented, and derived empirically, spectral image based classifiers using a combination of spatial and spectral information. One category of approaches exploits the texture of groups of spectricity pixels as a spatial metric of pixels leveraged in combination with spectral vectors for each pixel sampled from an object. Texture provides information about the spatial arrangement of these N-D spectricity vectors in an image or selected region of an image. Texture may be assessed using a variety of methods that make a quantitative measure of the arrangement of the spectral values of pixels in a region. Examples include edge based measures, e.g., based on edge magnitude and/or direction of edges detected in a region. Related measures include use of a gradient based edge detector to detect edge metrics in a region of pixels, such as gradient magnitude and direction, and then deriving a texture description by combining the edge metrics for the region. One such approach is a histogram of the gradient magnitudes and orientations of the region.

Co-occurrence matrices for the spectricity vectors of pixels in the region are another example of texture measures for a region.

Texture masks convolved with a region are another way to measure various spatial structures.

The use of spatial FFTs to derive spatial frequency characteristics of the N-D spectricity vector is yet another way to measure spatial relationships among spectricity pixels.

Various spatial filtering techniques may be uses as well. Examples include filters that compare each pixel with one or more neighboring pixels, or collectively, an average or other combination of spectral vectors of neighboring pixels. The spatial structure used for determining location or locations of pixels in a region for comparison may be empirically derived to detect particular structures for classifying an object. For example, using matlab code, we derive a texture descriptor model in matlab code that parameterizes the relationship between a pixel of interest and its neighbor or group of neighbors in terms of relative location/spacing, direction, and function for comparison of the pixel and its neighbors (e.g., weighting applied to the comparison as a function of pixel location to implement a filter function of a desired shape). The matlab code is a general filter model with adjustable parameters, where particular parameters create instances of the filter that we can evaluate for effectiveness in our classifier for a particular classification task. We then run experiments, plugging in a range of different variables for use in our classifier to discover the variables that yield the most reliable classifier for the test data set of the application.

One of skill will recognize that the various techniques, though different in name, are seeking to exploit similar spatial structure or spatial relationships within a region of spectricity pixels.

Derivatives.

Continuing with this theme, we now describe a particular example where we leveraged spatial relationships between spectral values of pixels in a region to improve classification. In one embodiment, spectricity derivatives are input to the classifier, for training and for classification. We experimented with various approaches in which the input for training and testing the classifier comprised a summation of spectricity vectors for pixels and spatial derivatives, generally of the form:

S+ΣS'+ΣS"+ . . . , where S is a spectricity vector at a pixel location, and S' is a first derivative, S" is a second derivative. For our implementation, our matlab software code computes the derivative as differences between the N-D spectricity value at the pixel location and a corresponding pixel location. We used a parameterized model as summarized above to test different relationships, varying the spacing, direction, and function for combining or not pixel values at two or more locations prior to computing the difference between the combined value and the value at the pixel of interest.

For the case of distinguishing apple varietals with our VQ classifier, we found that the spectricity difference values, computed at pixel spacing that corresponds to about 1-2 mm on the surface of the apple, provided improved discrimination accuracy over using spectricity values without any spatial information as input to the VQ classifier. In particular, the matlab code computed pair wise spectricity differences of a spectricity value of a brighter pixel minus the spectricity value of a dimmer pixel approximately 4 pixels away, which in our spectral image capture configuration corresponded to about 1-2 mm spacing on the surface of the fruit. Of course, the parameters of the filter used to compute a texture descriptor from spectricity vectors of pixels in a region may vary by application, and can be derived using the empirical method described or like methods. They may also be derived using machine learning methods to ascertain values for parameters of the spectral based texture descriptor that improves discrimination performance between classes. Other variations that may enhance performance include, but are not limited to:

Summation of derivatives over spatial scales (e.g., sub-millimeter, millimeter, centimeter spacing on the object being imaged);

Including integrated brightness to the input data vector (less as a discriminant, but more as way to determine and compensate for measurement error)

Including spectricity or not in addition to the spectricity difference as input to the classifier.

We sometimes refer to the spatial transform function of pixels prior to inputting to the classifier as a freckle transform, as it assists in characterizing spatial structure/texture on the surface of the object. In particular, we observed that the spatial differencing was effective in discriminating apple varietals with different surface texture corresponding to freckle patterns.

The freckle transform may start out as a generalized spatial transform with parameters that can be tuned to optimize the extraction of a vector that provides desired discrimination performance in the classifier. Indeed, the parameters of the transform can be tuned through machine learning on a training set or sets of objects to be classified or recognized.

Another observation is that the performance of the classifier can be enhanced by ascertaining variation in brightness across the N-D spectral measurements and compensating for that variation. This compensation is then applied to input vectors prior to inputting them into the classifier.

One particular method of classifying fruits and vegetables is as follows:
  sensing multispectral information from spaced-apart locations imaged from a vegetable or fruit;
  determining multispectral differences between pairs of such locations; and
  employing said multispectral differences, in conjunction with reference data, in identifying the vegetable or fruit by cultivar.

Returning to the general topic of leveraging spatial relationships among pixels, we emphasize that additional complementary forms of spatial structure of a group of neighboring N-D spectricity pixels may be used as well. Examples include multiresolution and rotation invariant measures of a texture feature of a neighborhood of spectricity pixels, such as texture derived from multiresolution analysis used in image classification. See for example, US Patent Publication 20030147558. Multiresolution analysis methods include wavelet and Gabor transform based methods. Rotation invariant texture may also be used, such as rotation invariant methods employing Radon transforms.

Classifying Vectors of Spectricity Pixels.

By classifying multiple spectricity pixels in a single feature vector, the joint probability distribution over the multiple pixels is used for the classifier design, and so the conditional distributions on one pixel given other pixels can be taken advantage of. Classifying vectors of pixels together is fundamentally similar to the common practice in image and video compression of quantizing groups of pixels to take advantage of the memory in the source.

All else being equal, the classification task for groups of pixels will require a larger training set to adequately fit the joint distribution, and will, unsurprisingly, be more complex.

To capture the largest amount of memory for a given size vector, it is reasonable to choose pixels close together (under the assumption that nearby locations are more correlated than farther apart locations); a common choice would be to choose a vector of n×n spectricity image pixels.

Both VQ based approaches and SVM can be used to classify vectors of pixels.

In the case of a VQ based system, the estimated pmfs would be over a k-dimensional product space of the VQ cell indexes, where k is the number of pixels in each vector to be quantized. This would likely be impractical for all but the smallest sized vectors. One approach to mitigate the complexity would be to use a VQ with a smaller number of cells.

For SVM, complexity will also increase with vector dimension, but probably not as quickly as with the VQ approach. Also, there is a specific kernel, called histogram intersection, which has been successfully used for images, and which can be efficiently calculated.

Multiscale Classification

Resampling the image (such as by using an averaging filter) at different scales, might produce different spectricity distributions for different scales. These differences can be another method for differentiating between classes. This method is attractive because it would not greatly increase complexity (probably nearly linear in the number of scales). Both VQ based methods and SVM methods could be used.

Crowd Sourcing to Compile Reference Data of Spectral Images and Object Labels

One practical challenge in building and maintaining classifiers is the collection, enrollment and accurate labeling of reference feature vectors sets captured for particular classes of objects. The techniques described in this document facilitate crowd based sourcing of spectral images. One way they facilitate it is by providing a means to characterize the light source and camera configuration of user's devices, such as by calibrating based on a device's coupling matrix. This simplifies the user contribution, as they can simply identify a camera device or smartphone used to capture uploaded image data, and the cloud service, in turn, applies the corresponding calibration by looking up the coupling matrix for the device and applying it to the uploaded image content. This calibration process can be automated through a handshake process between the user's mobile device and cloud service: upon establishing a communication with the spectral image enrollment server in the cloud, the user's device shares its camera device parameters. The enrollment server, in response, retrieves a coupling matrix corresponding to the camera device parameters (e.g., which identifies make, model of smartphone and/or its version of light source and camera sensor pairing.) The spectral data uploaded is then transformed according to the coupling matrix to calibrate it with other reference spectral vectors enrolled in the reference database of spectral vector images.

Surface Morphology

We noticed in spectral images obtained for a collection of green vegetables and peppers in the camera's field of view that spectricity signature values seem to have very distinct ridging and contouring around the various subject matter, with the Zucchini and Cucumbers being particularly striking in this regard. Part of this effect may be due to slight non-linear residual properties of the camera, where surfaces having different slant-angles relative to the camera will move through luminance space and ever so lightly change the ratios of LED/pixel digital values (hence, slightly change the ~8-12D vector values). So this 'problem' with a slightly non-linear camera (which almost all cameras are not perfectly linear) now provides a way to measure surface normal, and recover an estimate of 3D shape, as disclosed herein.

Back Projecting Approaches to RGB Cameras

Several of the approaches discovered in our experiments have utility in the 2D chromaticity space. In particular, while using multiple LEDs provides advantages, in some cases, our inventive methods and configurations can be implemented using Bayer color cameras and signal processing of the chromaticity images captured from them. Our methodology for deriving these methods is as follows: develop a signal processing method using a higher dimensional space (e.g., 6D-15D spectricity ratios), and then seek to approach similar results in the 2D chromaticity space (e.g., 2 chromaticity ratios). One example is the above mentioned process of determining shape from chromaticity gradients.

Spectral Imaging Integrated with Other Recognition Technologies

Object Recognition Combining Spectral Image Based Recognition with Other Feature Vectors As described above, the above techniques for capturing and deriving spectral based feature vectors can be combined with 2D and 3D recognition methods to improve object discrimination and identification. The following sections, and material incorporated by reference, provide additional explanation of such recognition methods, as adapted to leverage spectral image information for identification.

In one embodiment, object recognition is enhanced by performing locally adaptive combination of spectral images (e.g., 15D spectricity vectors) to extract black/white images that are then input to 2D image recognition methods. Many image recognition techniques predominantly rely on spatial features and structures derived from luminance images (black and white images), neglecting color and spectral information for object discrimination and recognition. These spatial features include size and shape of structures in an image, often characterized by contours, edges or corners.

Machine learning techniques can be employed to derive a mapping of N-D spectral vectors to images that provide more reliable discrimination of images, and objects depicted within the images. Once derived, the mapping is applied to generate 2D images that are fed to the 2D or 3D recognition services for identification.

One such example is the use of a mapping of the N-D spectral vectors to a spectral feature set to provide a substitute for color based feature vectors in a Bag of Features image or object recognition approach. Various techniques described in this document or the references incorporated herein may be used to derive the mapping of N-D spectral vector images to a spectral feature vector for such applications.

One example employing vector quantization and Bag of Features is as follows. In a Bag of features approach for object recognition based on image input, the input image data undergoes:

1. Feature Extraction in which the input images are converted to sets of descriptors of various types, which may include SIFT, dense, color-based, shape based, and N-D spectral based descriptors;

2. Quantization: for each set of feature descriptors, quantize the set into quantization bins. There are a variety of strategies for assigning descriptors to bins, as noted in connection with vector quantization. Such strategies include K-means, soft assignment, e.g., Gaussian mixture, etc. The process of assigning descriptors to bins results in a histogram, which provides a frequency of mapping descriptors into bins for a particular descriptor type. The histograms provide a representation of an unknown input that can then be matched against a database of reference histograms for identification (e.g., looking up the closest match, and determining the unknown item to have the identity or classification of that matching reference item).

3. The above methodology provides a basis for automated classifier design, or machine learning. For example, a neural net methodology has inputs for the bins of the histograms. It can be trained by submitting labeled items, e.g., objects.

N-D spectral vectors provide a powerful discriminator and identifier in this type of frame work. It may be employed for object recognition, image recognition and related classification applications. Below, we provide additional background on methods in which the spectral information may be employed as a feature descriptor.

Background for Image Recognition

Fingerprint-based content identification techniques are well known. SIFT, SURF, ORB and CONGAS are some of the most popular algorithms. (SIFT, SURF and ORB are each implemented in the popular OpenCV software library, e.g., version 2.3.1. CONGAS is used by Google Goggles for that product's image recognition service, and is detailed, e.g., in Neven et al, "Image Recognition with an Adiabatic Quantum Computer I. Mapping to Quadratic Unconstrained Binary Optimization," Arxiv preprint arXiv:0804.4457, 2008.)

Still other fingerprinting techniques are detailed in patent publications 20090282025, 20060104598, WO2012004626 and WO2012156774 (all by LTU Technologies of France).

Yet other fingerprinting techniques are variously known as Bag of Features, or Bag of Words, methods. Such methods extract local features from patches of an image (e.g., SIFT points), and automatically cluster the features into N groups (e.g., 168 groups)—each corresponding to a prototypical local feature. A vector of occurrence counts of each of the groups (i.e., a histogram) is then determined, and serves as a reference signature for the image. To determine if a query image matches the reference image, local features are again extracted from patches of the image, and assigned to one of the earlier-defined N-groups (e.g., based on a distance measure from the corresponding prototypical local features). A vector occurrence count is again made, and checked for correlation with the reference signature. Further information is detailed, e.g., in Nowak, et al, Sampling strategies for bag-of-features image classification, Computer Vision-ECCV 2006, Springer Berlin Heidelberg, pp. 490-503; and Fei-Fei et al, A Bayesian Hierarchical Model for Learning Natural Scene Categories, IEEE Conference on Computer Vision and Pattern Recognition, 2005; and references cited in such papers.

Background on 3D Object Recognition

In our related work, we describe methods for 3D object recognition based on capture of 2D images. See our related application 61/838,165, entitled ID of Things, which is hereby incorporated by reference.

In addition to this work, several papers outline methods for 3D object recognition, and are incorporated by reference herein. The object recognition techniques in the following can be adapted by using spectral image data as input and additionally employing spectral signatures for object discrimination:

Fei-Fei et al, A Bayesian Hierarchical Model for Learning Natural Scene Categories, IEEE Conference on Computer Vision and Pattern Recognition, 2005;

Ohbuchi, et al, Distance Metric Learning and Feature Combination for Shape-Based 3D Model Retrieval, Poster Presentation, Proc. of the ACM workshop on 3D Object Retrieval, 2010.

Lian, et al, Visual similarity based 3D shape retrieval using bag-of-features, IEEE Shape Modeling International Conference 2010; and Ohbuchi, et al, Accelerating bag-of-features SIFT algorithm for 3d model retrieval, Proc. SAMT 2008 Workshop on Semantic 3D Media; which are all hereby incorporated by reference.

These techniques are made more powerful by utilizing a mapping of N-D spectral vectors into spectral signatures as a means to further discriminate objects. In addition, the N-D spectral vectors are mapped into color or black and white images that are used for feature extraction as a substitute for the feature extraction from image input used previously in these methods.

Imaging devices with 3D sensing capability, such as plenoptic cameras and Kinect sensors provide the capability of shape of 3D objects to be ascertained and added as a discriminating or identifying feature input to a classifier or recognition system. These varying types of 3D information, including 3D information to obtain 3D surface texture and 3D information to determine object shape and boundaries can also be leveraged with the other technologies described in this document to classify and recognize objects.

Produce (e.g., Fruit and Vegetables)

In commonly assigned provisional application 61/724, 854, we disclose a method of gathering spectral signature for incoming batches of fruit as it arrives at a grocery store, and using this batch-derived signature info (rather than a worldwide "Standard" for fruit signature data) for fruit identification. 61/724,854, and US Patent Application Publication 20130223673, both entitled METHODS AND ARRANGEMENTS FOR IDENTIFYING OBJECTS, which are hereby incorporated by reference.

As noted above, others have posited that spectral information can be used for produce identification at check-out. See Henty's U.S. Pat. Nos. 6,363,366 and 7,319,990, which are hereby incorporated by reference.

In this section, we describe a produce classifier based on the above spectral imaging technology. A first embodiment utilizes 7 narrow-band LEDs and a color video camera capture. Another embodiment is the same, but uses a black and white video camera.

The LED lighting and the camera view are co-centered on a point on a conveyor belt. The LED lighting is cycled, (1 to 2 full cycles per second) such that there are individual full frames inside the video stream which uniquely correspond to only one LED source being on during that full frame's exposure. Compiled Matlab code ingests the video, picks out these uniquely lit frames, and quickly generates an N-D (N is empirically derived) spectricity signature vector for every point in the camera's field of view. The code also has access to a library of fruit/vegetable N-D signature families—essentially average N-D signatures for unique kinds of fruits/vegetables. Software code then compares acquired N-D scene signature vectors with this stored library, and when the acquired signature is within a threshold of proximity to a library signature, an output value for that pixel will be generated corresponding to the matched fruit/vegetable. Such output values, ranging across several types of fruits/vegetables, can then be 'mixed' with the ingest video to then produce a graphic ID-overlay video stream.

As additional background for the use of spectral information for produce identification and ripeness, see: A. Solovchenko, O. Chivkunova, A. Gitelson, and M. Merzlyak, Non-Destructive Estimation of Pigment Content, Ripening, Quality and Damage in Apple Fruit with Spectral Reflectance in the Visible Range, in Fresh Produce 4 (Special Issue 1), 91-102 © 2010 Global Science Books, which is hereby incorporated by reference. On page 4, second column mid-way down, this article refers to signature analysis of fruit spectra' and refers to three key wavelengths as the ratio generators. This provides background as to the use of spectral information to discriminate fruit/produce and relative ripeness. Our technology enhances identification and discrimination using readily available light source and camera components, configured as described, to generate spectral images. Selection of the LED spectra is guided by which chemical species are involved in the subject matter, mainly chlorophyll, carotenoid, etc.

Ripeness

Figure 58:
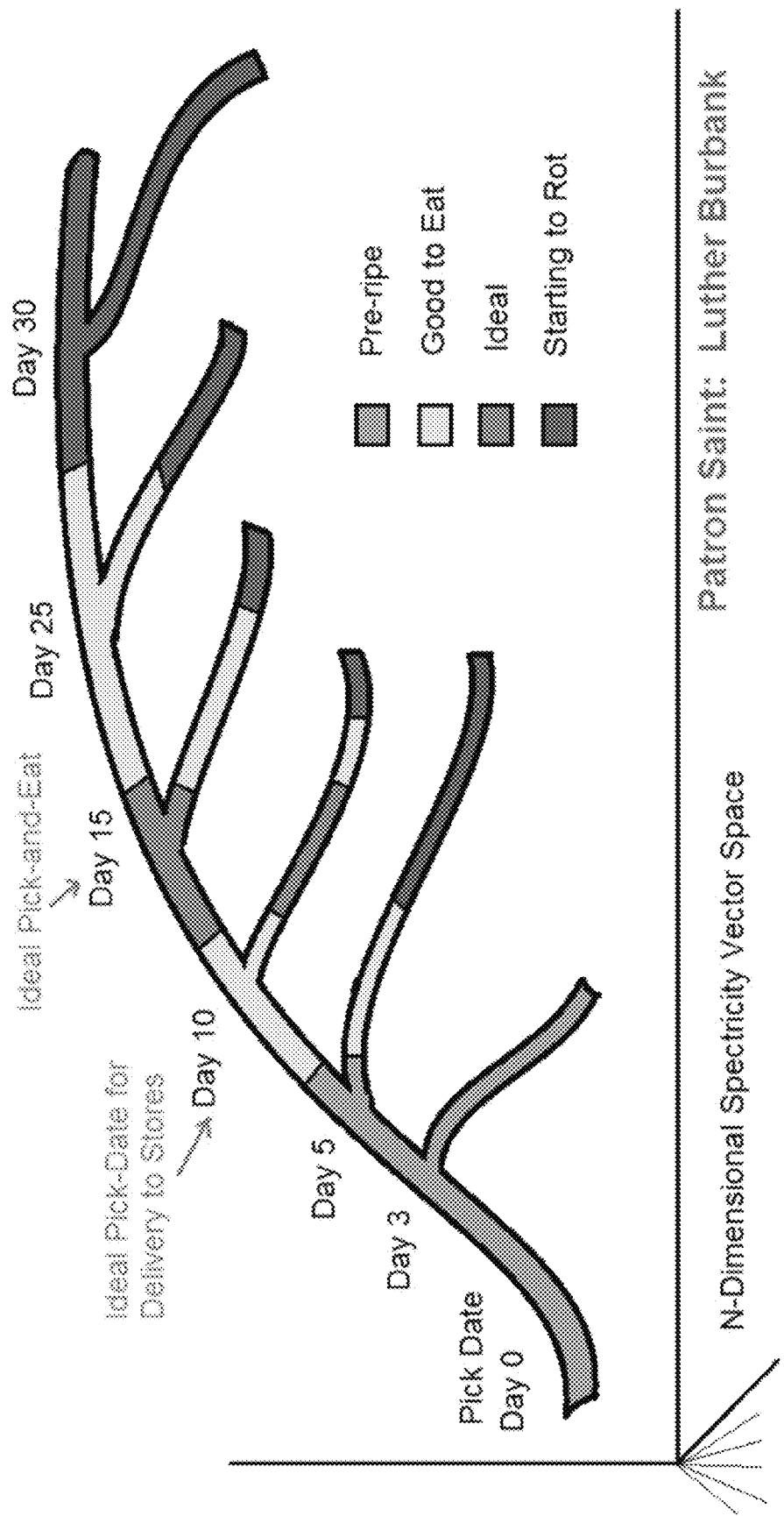
FIGS. 58-60 illustrate an application of N-D spectral vectors to identify ripeness of produce.
Figure 59:
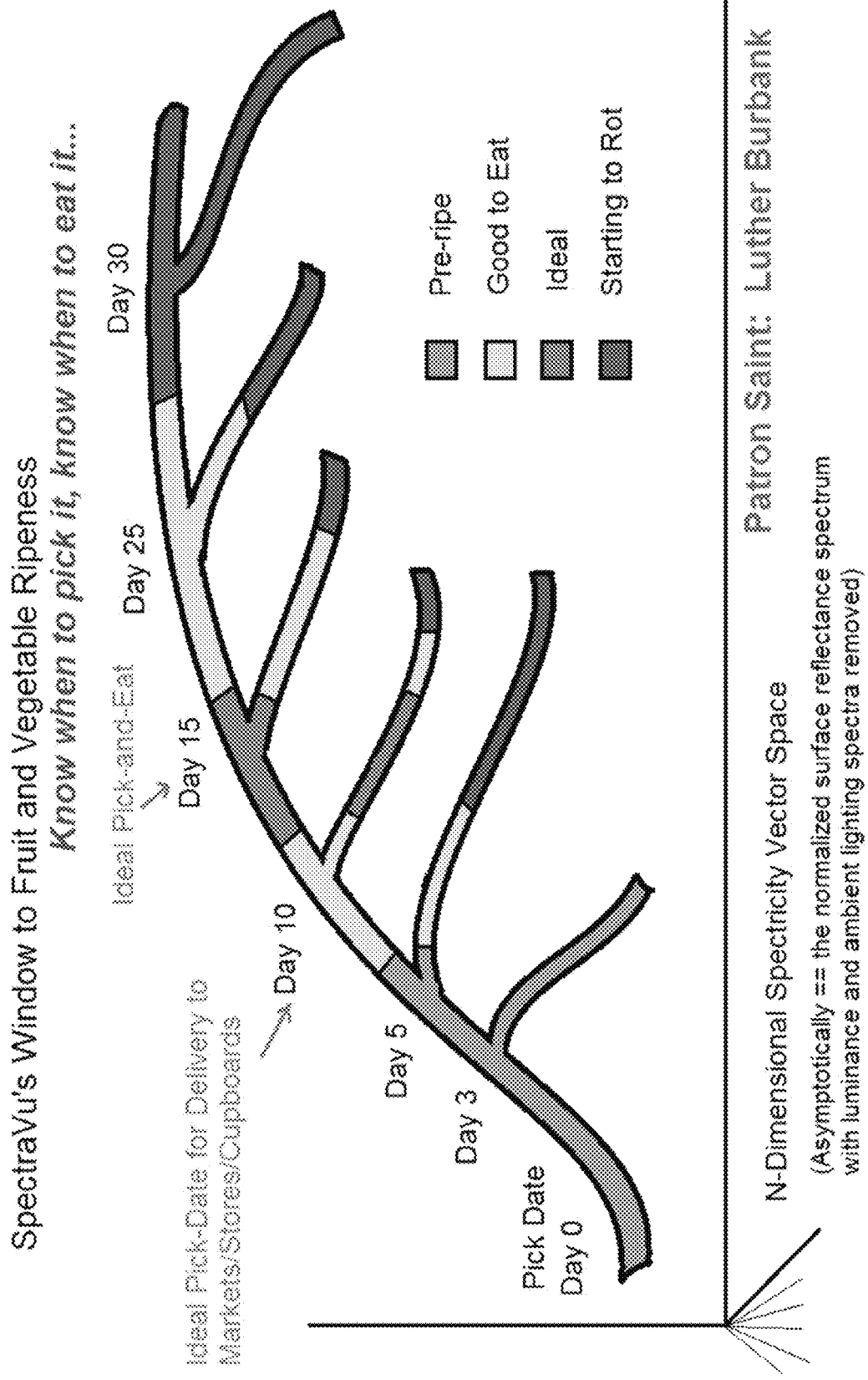
Figure 60:
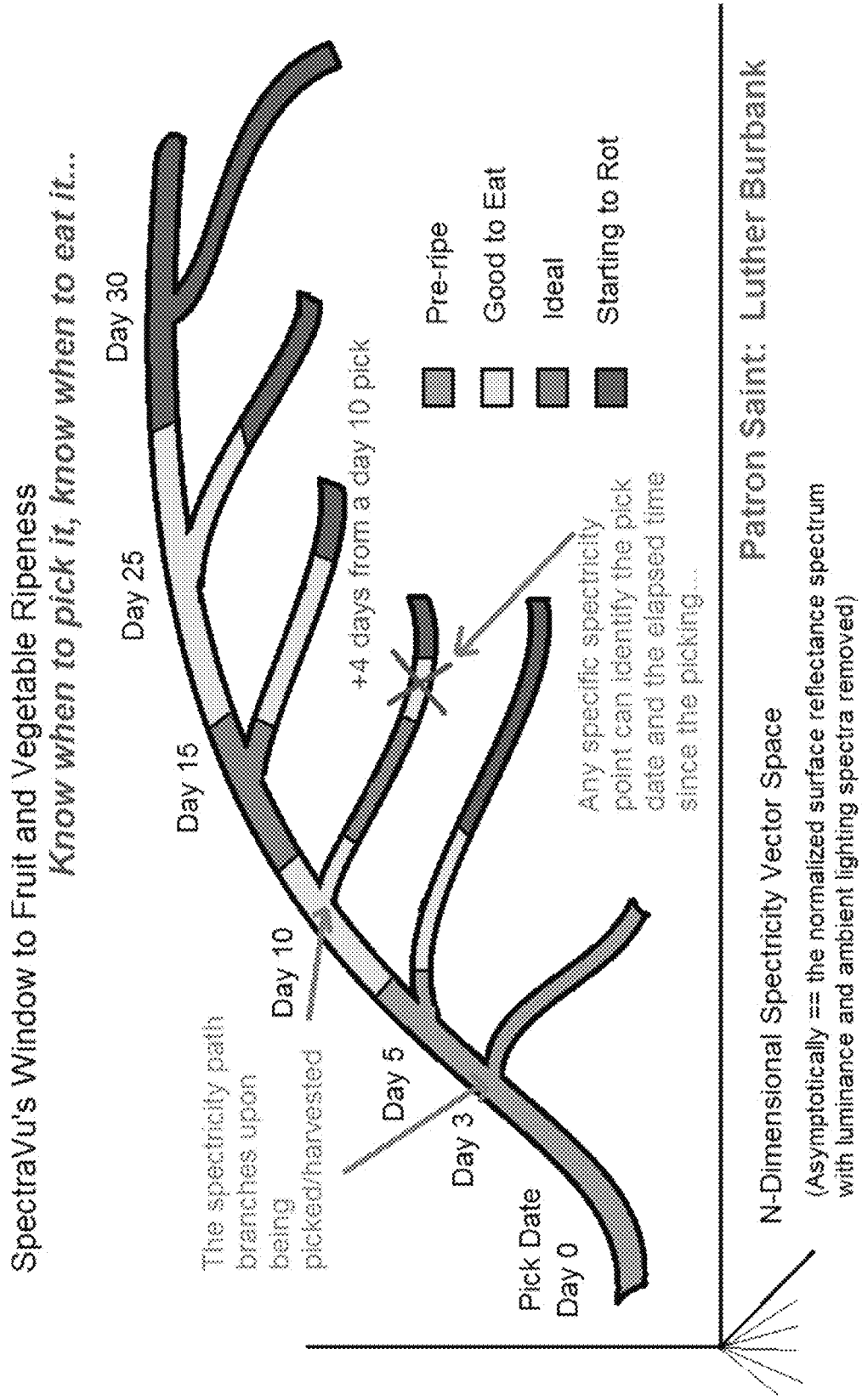

Building on this background, FIGS. 58-60 illustrate an application of N-D spectral vectors to identify ripeness of produce. In this application, the spectral characteristics of a produce item are characterized in N-D spectral space. As illustrated, a produce item follows a path or curvature through N-D space that is correlated to its stage of ripeness, and also accounts for pick date and time elapsed since the pick date. Unique models defining these regions for various produce items are derived through a training process on sets of spectral images collected for the produce items.

To determine ripeness, the produce item is imaged using spectral image capture techniques described above and spectral vectors are derived and mapped into the N-D space. The mapped data is correlated with the model to determine where it is located along the ripeness path. This ripeness determination is then output. One form of output, for example, is an AR type UI as explained above, in which the user's mobile device displays a graphic overlay on the video feed of a produce item depicting its stage of ripeness.

As noted above, 2D, 3D spatial information combined with spectral and polarimetric information at or below the surface of a produce time provide additional discrimination of produce type and ripeness. We combine the above described imaging devices for capturing polarimetric and spectral information at or below an object's surface with machine learning based design of a classifier to discern produce type and ripeness. Our design of such systems draws on work in fields of spectral imaging, stereochemistry, and ellipsometry. The fields of phytochemistry and biochemistry also provides useful teaching regarding the relationship of optical properties and produce classification and ripeness, as noted above, and in the cited work by Solovchenko et al. See also, K. Gross; C. Sams, Changes in Cell Wall Neutral Sugar Composition During Fruit Ripening: a species survey, Phytochemistry, Volume 23, Issue 11, 1984, Pages 2457-2461, which is hereby incorporated by reference. This work analyzing changes in sugar molecule composition during ripening indicates that measurements of the composition by optical means provides an indicator of ripeness stage. Thus, the above described spectral image capture and measurement of polarimetric information corresponding to sugar composition at or just below the surface of produce provides an indicator of ripeness. The above techniques for designing classifiers for such features, therefore, provide guidance for building ripeness classifiers for produce items. Specifically, in one configuration, spectricity vectors, possibly in combination with spatial and polarimetric information, are input into a classifier to discern produce type. Then in another classifier stage, optical measures of ripeness are input to a classifier to ascertain ripeness stage for that produce type. Various configurations are possible. In some applications, the user may simply select the produce type, and then use the classifier to compute the ripeness stage from optical information captured from the produce item.

Recapping the above themes on produce classification and ripeness stage detection, the task of distinguishing one fruit/vegetable from another, followed by identification of the 'ripeness stage' that a given produce item is in, has many underlying physical bases to draw from, not just the pigment molecule presents itself on the surface of a particular produce item. The processes going on underneath the top expressed surface layers are important to the ripeness-stage expressions of the surface in the surface's full three dimensionality. This underlying cell-structure development also gives rise to characteristic spatial-scale patterning of those structures, some at the sub-millimeter dominant scale and others a sub-centimeter scales and larger, fitting in well to sampling of spatial information at a range of spatial scales and depths.

The above techniques can be applied similarly to many applications spaces, including color matching for cosmetics (matching make-up to skin tones), color matching for paints and inks, automated printer color calibration, and spectral analysis of blood for various health analytic applications. These are just a few examples. The wider array of applications based on spectroscopic technology are applications where this technology may be applied to provide advances in terms of cost, effectives, and wider deployment. As the above technology relies on light source and camera sensor pairs that are readily available in many form factors, including for mobile and wearable computers and sensors, the technology can extend spectral imaging applications across a wider array of devices and form factors.

Personal Health and Nutrition

One growing trend is the development of wearable health monitoring devices, such as bracelets, with sensors to track motion, etc. The above technology may be integrated into this wearable form factor to capture spectral image data of blood flowing beneath the skin where the device is worn by a user. As the user's body breaks down food, the LED-camera based sensor detects the amount of light that passes through the blood based on green, red and infrared patterns.

Unique Identification of Printed Objects

The identification power of N-D spectral vectors may be leveraged by selecting combinations of inks or ink additives that uniquely identify or discriminate classes of printed objects. Patches of such unique ink formulations may be printed on product packaging for example, to identify it. The use of ink variations, as well as the spatial dimension to vary formulations over different patches, provides additional degrees of freedom to identify a printed item (as a function of spectral composition and location to provide a 2D or higher dimensional spectral code as function of location and N-D spectral vector composition). This application of spectral codes may also be applied in layers applied by 3D printers.

These objects are identified by computing spectral N-D vector images from images captured of the printed object, mapping them to a feature descriptor space, and matching them with reference data in a reference database (using above referenced classification technologies, for example). Alternatively, or in combination, the spectral descriptors may be used to encode data symbols, which are detected using a classifier, then converted to a data symbol and further processed (e.g., using error correction and detection) to provide a robust, variable data signal that can encode an identifier and any other desired metadata.

The standard Pantone spot color set consists of 1114 different spot colors, each mixed from some combination of 13 base inks, plus black. Of these, somewhat over 50% of them can be matched by screening a combination of the standard CMYK process inks. Pantone has a 6 color process, called Hexachrome, which allows screened reproduction of almost 90% of the spot colors. So, one can get around 8 or 9 bits per screened CMYK color "patch", and slightly more for a Hexachrome "patch". The selection of inks may be designed in conjunction with the selection of the LED sensor pairing of a reader device to obtain the desired address space of unique symbols that may be encoded in a particular printed patch.

As another variation, optical nanodot solutions can be added to ink formulations to introduce spectrally distinguishable characteristics. For example, differing ratios of nanodot injected material produces a modulation of the spectral vector of a printed patch, which can be used to encode a data symbol or graphical element of a detectable geometric pattern.

Relatedly, digital watermarks may be encoded in spectral information as disclosed in our related application 61/832,752, which is incorporated by reference. See also teaching of additional signal encoding techniques in 61/832,752, which is also incorporated by reference. The teachings of 61/832,752 and 61/832,752, can be combined with the technologies in this disclosure to provide a means to identify printed objects using various data encoding techniques, identifying patterns, image recognition in spectral domains, including spectral ratio or spectral differences, as disclosed in these references and this document.

This technology can then be applied in various other industries where such spectral information may be conveyed in colorants, dyes, inks etc., such as food dyes, clothing dyes, colorants for cosmetics, pharmaceuticals, medical diagnostic materials for imaging within the human body, etc.

Regarding medical imaging applications, our techniques of using spectral information, alone or in combination polarimetric information and 2D and 3D spatial, depth (e.g., spectral and polarimetric measurements for pixels at and below skin surface), and can be used to augment approaches such as described in U.S. Pat. Nos. 6,996,549 and 8,543,519, which are hereby incorporated by reference.

Other Form Factors

Point of Sale Form Factors

Another important form factor is object scanning equipment at the Point of Sale (POS). Barcode scanning equipment increasingly employs digital cameras to capture images of objects as they are waved passed a scanner. This equipment is a suitable environment in which light source-camera sensor pairs may be employed as disclosed above. It affords the advantage of positioning light sources and cameras to measure spectral information, as well as derive surface structure information as described.

Additional Applications

The following table provides additional application fields, use cases and example spectral imaging configurations employing technology described in this document. The additional product details are examples only and any of the device types noted in the document may be employed, as appropriate for the application.

| APPLICATION | Explanation | Additional Product Details |
|---|---|---|
| Digital watermarking | A natural fit, see above | Smartphone, POS scanner, special purpose imager |
| Quality Control | excellent fit- use N++ band (UV/IR) | In machine vision equipment in manufacturing setting; and post shipping, in smartphone embodiments |
| Dermatology | Identify skin problems with UV, IR | standalone camera |
| Dental | Use your camera phone to check for plaque | Integrated in smartphone |
| Security Camera | IR LED, big market | Integrated in security camera |
| CPG - checkout | Improved barcode, digital watermark on packaging improved using spectral channel | Integrated in POS imager |
| Part Inspection | Identify specific appearance aspects | In machine vision equipment in manufacturing setting |

| APPLICATION | Explanation | Additional Product Details |
|---|---|---|
| Fruit/Vegetable | UV, IR and 'yellow' - beats human eye | Integrated in POS imager or in-store produce scale, or machine vision system of produce supply chain |
| Social interaction | like pheromones but with color | mood analyzer in smartphone application |
| Art Photography/ Graphics | Special effects like IR images | better color, pseudocolor, with specialty flash and software/firmware, FPGA, and/or ASIC in camera |
| Professional Photography | Enhanced color rendition | same |
| Consumer photography | Always a good picture with improved ambient sensing of lighting on subject and adapt flash | same |
| Archival photography | Enhanced color rendition | |
| Counterfeit detection | Great application, good fit | Spectral information provides greater discrimination of counterfeits |
| Medical | Many applications | |
| Stress Test | Blood flow in forehead? IR | |
| Breathalyzer | UV/IR can 'see' chemistry in vapor | |
| Spelunking/Mining | High value niche | |
| Optometry | Inspect white of eye | |
| Motion Picture | | Cinematography; DDX |
| Endoscopy | | |
| Agriculture | fluoresence - UV especially and possibly IR | looking at cultures/ nurseries/Healthy? Flowering? |
| Forensics | Crime scene, lit by UV to see DNA | every department needs one/DDX + special camera |
| BioTech | fluoresence - UV especially | Microscope, DDX |
| Traffic Cam | IR of course | |
| Shoe Sales | | |
| Paint store | Need high accuracy | Use spectrometer |
| Fabric store | Need high accuracy | |
| Tailor's shop | | |
| Hair Salon | Possibly easy, good size market | |
| Science teaching | Easy | philanthropy |
| Sports Photography | (training facility) | high frame rate flash (pro vs everyone else?) |
| Surveillance | IR in the dark of course, but N++? | what's the benefit |
| Crime Prevention | | tracking? Lighting of large area? |
| Facial Recognition | | |
| Underwater Photography | | |
| Chemical composition | | |
| Blood donor | | |
| Passport photography | Watermark reading and document authentication | |
| Airline check-in | Watermark reading and document authentication | |
| Ticket gate | Watermark reading and document authentication | |
| Crowd counter | | |
| War games | | |
| Minerals evaluation | | |
| Oil and gas exploration | | |
| License plate capture | All the lightbulbs in the factory are White/White - time alternated colorations generated from pulsing different spectral LEDs, for example. | |
| Consumer-use Inspection of fruit, merchandise, fabric | | |

CONCLUDING REMARKS

Applicant's other work concerning imaging systems is detailed, e.g., in patent publications 20110212717, 20110161076, 20120284012, 20120218444, 20120046071, and in pending application Ser. No. 13/750,752, filed Jan. 25, 2013 (Now issued as U.S. Pat. No. 9,367,770), and 61/759,996, filed Feb. 1, 2013.

Chrominance-based digital watermarking is detailed, e.g., in the just-cited application Ser. No. 13/750,752, and in U.S. patent documents 20100150434, U.S. Pat. Nos. 6,590,996 and 8,401,224.

While reference has been made to smart phones, it will be recognized that this technology finds utility with all manner of devices—both portable and fixed. Tablets, laptop computers, digital cameras, wrist- and head-mounted systems and other wearable devices, etc., can all make use of the principles detailed herein. (The term "smart phone" should be construed herein to encompass all such devices, even those that are not telephones.)

Particularly contemplated smart phones include the Apple iPhone 5; smart phones following Google's Android specification (e.g., the Galaxy S III phone, manufactured by Samsung, the Motorola Droid Razr HD Maxx phone, and the Nokia N900), and Windows 8 mobile phones (e.g., the Nokia Lumia 920).

Among the Android options, the Nokia N900 is usable with the open source FCam software for programmatic computer camera control. This is advantageous because the FCam technology can be called to cause a camera take certain actions that might be useful in a particular analysis.

Details of the Apple iPhone, including its touch interface, are provided in Apple's published patent application 20080174570.

The design of smart phones and other computers referenced in this disclosure is familiar to the artisan. In general terms, each includes one or more processors, one or more memories (e.g. RAM), storage (e.g., a disk or flash memory), a user interface (which may include, e.g., a keypad, a TFT LCD or OLED display screen, touch or other gesture sensors, a camera or other optical sensor, a compass sensor, a 3D magnetometer, a 3-axis accelerometer, a 3-axis gyroscope, one or more microphones, etc., together with software instructions for providing a graphical user interface), interconnections between these elements (e.g., buses), and an interface for communicating with other devices (which may be wireless, such as GSM, 3G, 4G, CDMA, WiFi, WiMax, Zigbee or Bluetooth, and/or wired, such as through an Ethernet local area network, a T-1 internet connection, etc.).

The processes and system components detailed in this specification may be implemented as instructions for computing devices, including general purpose processor instructions for a variety of programmable processors, including microprocessors (e.g., the Intel Atom, ARM A5, and nVidia Tegra 4; the latter includes a CPU, a GPU, and nVidia's Chimera computational photography architecture), graphics processing units (GPUs, such as the nVidia Tegra APX 2600), and digital signal processors (e.g., the Texas Instruments TMS320 and OMAP series devices), etc. These instructions may be implemented as software, firmware, etc. These instructions can also be implemented in various forms of processor circuitry, including programmable logic devices, field programmable gate arrays (e.g., the Xilinx Virtex series devices), field programmable object arrays, and application specific circuits—including digital, analog and mixed analog/digital circuitry. Execution of the instructions can be distributed among processors and/or made parallel across processors within a device or across a network of devices. Processing of data may also be distributed among different processor and memory devices. As noted, cloud computing resources can be used as well. References to "processors," "modules" or "components" should be understood to refer to functionality, rather than requiring a particular form of implementation.

Software instructions for implementing the detailed functionality can be authored by artisans without undue experimentation from the descriptions provided herein, e.g., written in C, C++, Visual Basic, Java, Python, Tcl, Perl, Scheme, Ruby, etc. Smartphones and other devices according to certain implementations of the present technology can include software modules for performing the different functions and acts.

Known browser software, communications software, imaging software, and media processing software can be adapted for use in implementing the present technology.

Software and hardware configuration data/instructions are commonly stored as instructions in one or more data structures conveyed by tangible media, such as magnetic or optical discs, memory cards, ROM, etc., which may be accessed across a network. Some embodiments may be implemented as embedded systems—special purpose computer systems in which operating system software and application software are indistinguishable to the user (e.g., as is commonly the case in basic cell phones). The functionality detailed in this specification can be implemented in operating system software, application software and/or as embedded system software.

Different of the functionality can be implemented on different devices. Thus, it should be understood that description of an operation as being performed by a particular device (e.g., a smart phone) is not limiting but exemplary; performance of the operation by another device (e.g., a remote server), or shared between devices, is also expressly contemplated.

(In like fashion, description of data being stored on a particular device is also exemplary; data can be stored anywhere: local device, remote device, in the cloud, distributed, etc.)

This specification has discussed several different embodiments. It should be understood that the methods, elements and concepts detailed in connection with one embodiment can be combined with the methods, elements and concepts detailed in connection with other embodiments. While some such arrangements have been particularly described, many have not—due to the large number of permutations and combinations. However, implementation of all such combinations is straightforward to the artisan from the provided teachings.

Elements and teachings within the different embodiments disclosed in the present specification are also meant to be exchanged and combined.

While this disclosure has detailed particular ordering of acts and particular combinations of elements, it will be recognized that other contemplated methods may re-order acts (possibly omitting some and adding others), and other contemplated combinations may omit some elements and add others, etc.

Although disclosed as complete systems, sub-combinations of the detailed arrangements are also separately contemplated (e.g., omitting various of the features of a complete system).

While certain aspects of the technology have been described by reference to illustrative methods, it will be recognized that apparatuses configured to perform the acts of such methods are also contemplated as part of applicant's inventive work. Likewise, other aspects have been described by reference to illustrative apparatus, and the methodology performed by such apparatus is likewise within the scope of the present technology. Still further, tangible computer readable media containing instructions for configuring a processor or other programmable system to perform such methods is also expressly contemplated.

The present specification should be read in the context of the cited references. (The reader is presumed to be familiar with such prior work.) Those references disclose technologies and teachings that the inventors intend be incorporated into embodiments of the present technology, and into which the technologies and teachings detailed herein be incorporated.

To provide a comprehensive disclosure, while complying with the statutory requirement of conciseness, applicant incorporates-by-reference each of the documents referenced herein. (Such materials are incorporated in their entireties, even if cited above in connection with specific of their teachings.)

In view of the wide variety of embodiments to which the principles and features discussed above can be applied, it should be apparent that the detailed embodiments are illustrative only, and should not be taken as limiting the scope of the invention. Rather, we claim as our invention all such modifications as may come within the scope and spirit of the following claims and equivalents thereof.

The invention claimed is:

1. An apparatus for spectral imaging comprising:
   an image sensor operable to obtain images, the images comprising pixel values corresponding to locations in a field of view of the image sensor;
   an illumination source comprising at least three LEDs, each a different color;
   a drive circuit that selectively strobes on the LEDs synchronized with capture of frames of the images by the image sensor;
   means for obtaining multi-spectral channel values per pixel corresponding to the LEDs;
   means for computing a spatial relationship function of pixels sampled from different locations of the field of view; and
   means for classifying an object depicted in the images as being one of plural different classes based on the multi-spectral channels per pixel and spatial relationship function.

2. The apparatus of claim 1 wherein the object comprises a produce item, and the means for classifying identifies a type of produce.

3. The apparatus of claim 1 wherein the spatial relationship function comprises a function of multi-spectral values of pixels at 2 or more spatial dimensions.

4. The apparatus of claim 3 wherein the spatial relationship function comprises a function of multi-spectral values of pixels at 3 or more spatial dimensions.

5. The apparatus of claim 1 wherein the image sensor comprises a polarizer, and the apparatus comprises a processor configured with instructions to detect pixels in the images that are impacted by specular reflection based on polarization obtained from the polarizer.

6. The apparatus of claim 1 wherein the image sensor comprises a monochrome sensor.

7. The apparatus of claim 6 wherein the illumination source comprises at least four different LEDs, each a different color, and each of the frames is captured to isolate a different state of LED illumination corresponding to the selective strobing of a color of one of the LEDs.

8. The apparatus of claim 1 wherein the means for classifying comprises a processor configured with instructions to execute a vector quantizer on the multi-spectral channel values per pixel.

9. The apparatus of claim 8 wherein the means for classifying comprises a processor configured with instructions to execute a tree structured vector classifier.

10. The apparatus of claim 1 wherein the means for classifying comprises a processor configured with instructions to execute a Support Vector Machine classifier on the multi-spectral channel values per pixel.

11. The apparatus of claim 10 wherein the means for classifying further comprises a processor configured to execute a vector quantizer on the multi-spectral channel values per pixel.

12. The apparatus of claim 1 wherein the means for classifying comprises a processor configured with instructions to execute a neural network classifier on the multi-spectral channel values per pixel.

13. The apparatus of claim 12 wherein the means for classifying comprises a processor configured with instructions to execute the neural network classifier on the multi-spectral channel values per pixel, wherein the spatial relationship function comprises 2D spatial information associated with the multi-spectral channel values per pixel.

14. The apparatus of claim 1 wherein the means for computing a spatial relationship function comprises a processor configured with instructions to determine a texture measure for a region of pixels in an image of the object.

15. The apparatus of claim 14 wherein the texture measure comprises pixel differences in the region.

16. The apparatus of claim 14 wherein the texture measure comprises a histogram of gradients.

17. The apparatus of claim 14 wherein the means for computing a spatial relationship function comprises a filter that compares pixel values of pixels in the region.

18. The apparatus of claim 14 wherein the means for computing a spatial relationship function comprises a processor configured with instructions to compute pixel differences of pixel values at pixel locations within the region, the pixel locations being at predetermined spacing and direction within the region.

19. The apparatus of claim 1 wherein the means for computing a spatial relationship function comprises a processor configured with instructions to determine a texture measure for a region of pixels in an image of the object; and
the means for classifying comprises a processor configured with instructions to execute a vector quantizer on the multi-spectral channel values per pixel.

20. The apparatus of claim 19 wherein the means for classifying further comprises the processor configured with instructions to execute a Support Vector Machine classifier.

\* \* \* \* \*